(12) United States Patent
Fagan et al.

(10) Patent No.: US 7,803,383 B2
(45) Date of Patent: Sep. 28, 2010

(54) METHOD OF TREATMENT COMPRISING ADMINISTRATION OF A CYTOKINE ANTAGONIST MOLECULE

(75) Inventors: Richard Joseph Fagan, London (GB); Andrew Robert Davids, London (GB); Christopher Benjamin Phelps, London (GB); Christine Power, Thoiry (FR); Ursula Boschert, Troinex (CH); Yolande Chvatchko, Vaumarcus (CH)

(73) Assignee: Ares Trading S.A., Aubonne (CH)

( * ) Notice: Subject to any disclaimer, the term of this patent is extended or adjusted under 35 U.S.C. 154(b) by 793 days.

(21) Appl. No.: 10/579,113

(22) PCT Filed: Nov. 12, 2004

(86) PCT No.: PCT/GB2004/004772

§ 371 (c)(1),
(2), (4) Date: Apr. 6, 2007

(87) PCT Pub. No.: WO2005/046714

PCT Pub. Date: May 26, 2005

(65) Prior Publication Data

US 2008/0025951 A1    Jan. 31, 2008

(30) Foreign Application Priority Data

Nov. 12, 2003 (GB) .................................. 0326393.6

(51) Int. Cl.
A61K 39/00 (2006.01)
A61K 39/395 (2006.01)
C07K 14/00 (2006.01)

(52) U.S. Cl. .................. 424/192.1; 424/158.1; 514/12; 530/387.1; 530/350

(58) Field of Classification Search ........................ None
See application file for complete search history.

(56) References Cited

U.S. PATENT DOCUMENTS

| 6,420,526 | B1 | 7/2002 | Ruben et al. | |
| 6,783,961 | B1 | 8/2004 | Edwards et al. | |
| 7,622,555 | B2 | 11/2009 | Davids et al. | |
| 2004/0043424 | A1 * | 3/2004 | Baughn et al. | 435/7.1 |
| 2004/0204352 | A1 | 10/2004 | Davids et al. | |

FOREIGN PATENT DOCUMENTS

| EP | 1127883 | 8/2001 |
| WO | WO 99/45910 | 9/1999 |
| WO | WO 02/40671 | 5/2002 |
| WO | WO 03/077832 | 9/2003 |
| WO | WO 03/093316 | 11/2003 |
| WO | WO 2004/007672 | 1/2004 |
| WO | WO 2004/080148 | 9/2004 |

OTHER PUBLICATIONS

Feldmann 2008. J Clin Invest 118:3533-3536).*
Steinman 2008. J. Clin Invest 118:3557-3563.*
Barnes 2008. J. Clin Invest 118:3546-3556.*
Yamagata et al 2006. European J of Pharm 533:289-301.*
Dinarello 2000. Chest. 503-508.*
Andreakos. 2003. Expert Opin Biol Ther. 3:435-447.*
Nathan et al 2006. J Gastroent. and Hepat. 21:1366-1371.*
Tilg 2001. Can J. Gastroenterol. 15:661-668).*
Trefzer et al 2003. Expert Opin Biol Ther. 3:733-743.*
International Search Report in International Application No. PCT/GB2003/001851, Oct. 28, 2003, pp. 1-6.
Sugano, et al. "NEDO human cDNA Sequencing project" Database Accession No. AK098396, pp. 1-2, Sep. 14, 2006, XP-002259341.
Batey, R. G. et al. "Molecular Pathogenesis of T Lymphocyte-Induced Liver Injury in Alcoholic Hepatitis" *Frontiers in Bioscience*, Jul. 1, 2002, pp. 1662-1675, vol. 7.
Nordmann, Y. et al. "Human hereditary hepatic porphyrias" *Clinica Chimica Acta*, 2002, pp. 17-37, vol. 325.
Vilcek, J. "The Cytokines: an overview" *The Cytokine Handbook*, Chapter 1, 2003, pp. 1-18.
Ngo, J. T. et al. "Computational Complexity, Protein Structure Prediction, and the Levinthal Paradox" *The Protein Folding Problem and Tertiary Structure Prediction*, 1994, pp. 491-495.
Wells, J. A. "Additivity of Mutational Effects in Proteins" *Biochemistry*, Sep. 18, 1990, pp. 8509-8517, vol. 29, No. 37.
Bowie, J. U. et al. "Deciphering the Message in Protein Sequences: Tolerance to Amino Acid Substitutions" *Science*, 1990, pp. 1306-1310, vol. 247.
Edwards, J. B. D. M. et al. "Sequence tag and encoded human protein" Database Accession No. BD511416, Aug. 27, 2002, p. 1, XP-002259339.
Marks, D. et al. "A review on the diagnosis, natural history, and treatment of familial hypercholesterolaemia" *Atherosclerosis*, 2003, pp. 1-14, vol. 168.
Ju, G. et al. "Conversion of the interleukin 1 receptor antagonist into an agonist by site-specific mutagenesis" *Proc. Natl. Acad. Sci. USA*, Apr. 1991, pp. 2658-2662, vol. 88.

(Continued)

*Primary Examiner*—Gary B. Nickol
*Assistant Examiner*—Shulamith H Shafer
(74) *Attorney, Agent, or Firm*—Saliwanchik, Lloyd & Saliwanchik

(57) ABSTRACT

This invention relates to novel uses of a protein sequence (INSP052EC), herein identified as an immunoglobulin domain-containing cell surface recognition, in the diagnosis, prevention and treatment of diseases, in particular those related to the excessive expression and/or secretion of cytokines.

8 Claims, 13 Drawing Sheets

OTHER PUBLICATIONS

Tang, Y. T. et al. "Isolated polypeptides for treatment of diseases, diagnostics, raising antibodies and research use" Database Accession No. AAM24238, Oct. 12, 2001, p. 1, XP-002259341.

Office Action dated Dec. 9, 2004 in U.S. Appl. No. 10/706,691, filed Nov. 12, 2003.

Office Action dated Sep. 23, 2005 in U.S. Appl. No. 10/706,691, filed Nov. 12, 2003.

Office Action dated Dec. 27, 2006 in U.S. Appl. No. 10/706,691, filed Nov. 12, 2003.

Office Action dated Jun. 6, 2007 in U.S. Appl. No. 10/706,691, filed Nov. 12, 2003.

Office Action dated Mar. 14, 2008 in U.S. Appl. No. 10/706,691, filed Nov. 12, 2003.

Office Action dated Dec. 23, 2008 in U.S. Appl. No. 10/706,691, filed Nov. 12, 2003.

* cited by examiner

FIG. 1(A)

```
              1         .         .         .         .         .        60
INSP052       MKRERGALSRASRALRLAPFVYLLLIQTDPLEGVNITSPVRLIHGTVGKSALLSVQYSST
INSP052EC     ----------------------------------VNITSPVRLIHGTVGKSALLSVQYSST
SEQIDNO880    MKRERGALSRASRALRLAPFVYLLLIQTDPLEGVNITSPVRLIHGTVGKSALLSVQYSST
SEQIDNO434    MKRERGALSRASRALRLAPFVYLLLIQTDPLEGVNITSPVRLIHGTVGKSALLSVQYSST
                                                ****************************

61        .         .         .         .         .       120
INSP052       SSDRPVVKWQLKRDKPVTVVQSIGTEVIGTLRPDYRDRIRLFENGSLLLSDLQLADEGTY
INSP052EC     SSDRPVVKWQLKRDKPVTVVQSIGTEVIGTLRPDYRDRIRLFENGSLLLSDLQLADEGTY
SEQIDNO880    SSDRPVVKWQLKRDKPVTVVQSIGTEVIGTLRPDYRDRIRLFENGSLLLSDLQLADEGTY
SEQIDNO434    SSDRPVVKWQLKRDKPVTVVQSIGTEVIGTLRPDYRDRIRLFENGSLLLSDLQLADEGTY
              ************************************************************

121       .         .         .         .         .       180
INSP052       EVEISITDDTFTGEKTINLTVDVPISRPQVLVASTTVLELSEAFTLNCSHENGTKPSYTW
INSP052EC     EVEISITDDTFTGEKTINLTVDVPISRPQVLVASTTVLELSEAFTLNCSHENGTKPSYTW
SEQIDNO880    EVEISITDDTFTGEKTINLTVDVPISRPQVLGASTTVLELSEAFTLNCSHENGTKPSYTW
SEQIDNO434    EVEISITDDTFTGEKTINLTVDVPISRPQVLVASTTVLELSEAFTLNCSHENGTKPSYTW
              ******************************* ****************************

181       .         .         .         .         .       240
INSP052       LKDGKPLLNDSRMLLSPDQKVLTITRVLMEDDDLYSCMVENPISQGRSLPVKITVYRRSS
INSP052EC     LKDGKPLLNDSRMLLSPDQKVLTITRVLMEDDDLYSCMVENPISQGRSLPVKITVYRRSS
SEQIDNO880    LKDGKPLLNDSRMLLSPDQKVLTITRVLMEDDDLYSCVVENPINQGRTLPCKITEYRKSS
SEQIDNO434    LKDGKPLLNDSRMLLSPDQKVLTITRVLMEDDDLDSCVVENPINQGRTLPCKITVYKKSS
              *********************************  **:***** ***:** *** *:;**

241       .         .         .         .         .       300
INSP052       LYIILSTGGIFLLVTLVTVCACW KPSKRKQKKLEKQNSLEYMDQNDDRLKPEADTLPRSG
SEQIDNO880    LSSIWLQEAFSSLGPW
SEQIDNO434    FYIICLKEASSSFGPW

301       .         .         .         .         .       360
INSP052       EQERKNPMALYILKDKDSPETEENPAPEPRSATEPGPPGYSVSPAVPGRSPGLPIRSARR

361       .         .         .         .         .       416
INSP052       YPRSPARSPATGRTHSSPPRAPSSPGRSRSASRTLRTAGVHIIREQDEAGPVEISA
```

FIG. 1(B)

```
INSP052EC       VNITSPVRLIHGTVGKSALLSVQYSSTSSDRPVVKWQLKRDKPVTVVQSIGTEVIGTLRP
INSP052Ig2        VRLIHGTVGKSALLSVQYSSTSSDRPVVKWQLKRDKPVTVVQSIGTEVIGTLRP
INSP052EC-6His  VNITSPVRLIHGTVGKSALLSVQYSSTSSDRPVVKWQLKRDKPVTVVQSIGTEVIGTLRP
INSP052EC-Fc    VNITSPVRLIHGTVGKSALLSVQYSSTSSDRPVVKWQLKRDKPVTVVQSIGTEVIGTLRP
                     ********************************************************

INSP052EC       DYRDRIRLFENGSLLLSDLQLADEGTYEVEISITDDTFTGEKTINLTVDVPISRPQVLVA
INSP052Ig2      DYRDRIRLFENGSLLLSDLQLADEGTYEVEISITDDTFTGEKTINLTVDVPISRPQVLVA
INSP052EC-6His  DYRDRIRLFENGSLLLSDLQLADEGTYEVEISITDDTFTGEKTINLTVDVPISRPQVLVA
INSP052EC-Fc    DYRDRIRLFENGSLLLSDLQLADEGTYEVEISITDDTFTGEKTINLTVDVPISRPQVLVA
                ************************************************************

INSP052EC       STTVLELSEAFTLNCSHENGTKPSYTWLKDGKPLLNDSRMLLSPDQKVLTITRVLMEDDD
INSP052Ig2      STTVLELSEAFTLNCSHENGTKPSYTWLKDGKPLLNDSRMLLSPDQKVLTITRVLMEDDD
INSP052EC-6His  STTVLELSEAFTLNCSHENGTKPSYTWLKDGKPLLNDSRMLLSPDQKVLTITRVLMEDDD
INSP052EC-Fc    STTVLELSEAFTLNCSHENGTKPSYTWLKDGKPLLNDSRMLLSPDQKVLTITRVLMEDDD
                ************************************************************

INSP052EC       LYSCMVENPISQGRSLPVKITVYRRSS
INSP052Ig2      LYSCMVENPISQ
INSP052EC-6His  LYSCMVENPISQGRSLPVKITVYRRSSHHHHHH
INSP052EC-Fc    LYSCMVENPISQGRSLPVKITVYRRSSEPKSCDKTHTCPPCPAPELLGGPSVFLFPPKPK
                ************

INSP052EC-Fc    DTLMISRTPEVTCVVVDVSHEDPEVKFNWYVDGVEVHNAKTKPREEQYNSTYRVVSVLTV
INSP052EC-Fc    LHQDWLNGKEYKCKVSNKALPAPIEKTISKAKGQPREPQVYTLPPSREEMTKNQVSLTCL
INSP052EC-Fc    VKGFYPSDIAVEWESNGQPENNYKTTPPVLDSDGSFFLYSKLTVDKSRWQQGNVFSCSVM
INSP052EC-Fc    HEALHNHYTQKSLSLSPGK
```

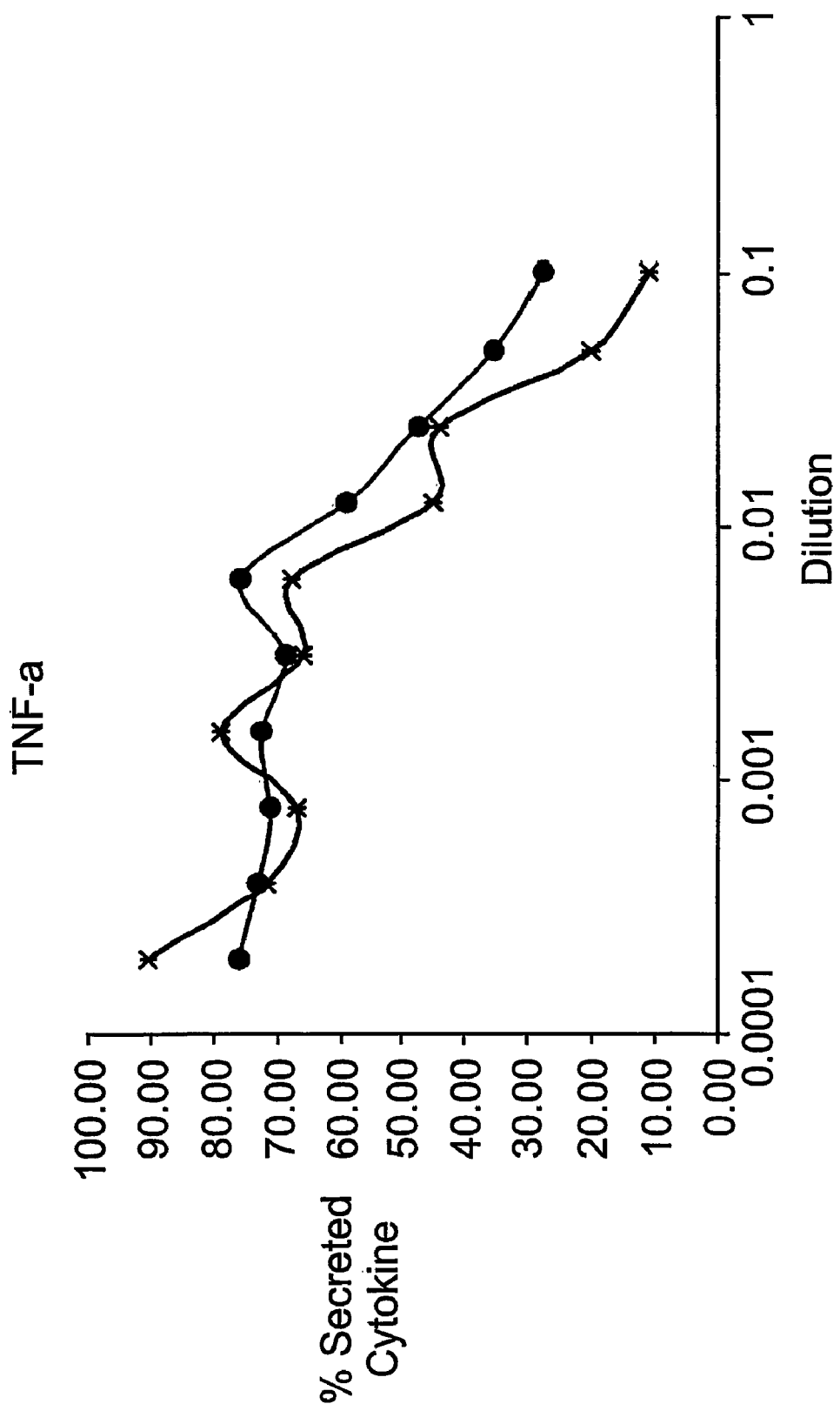

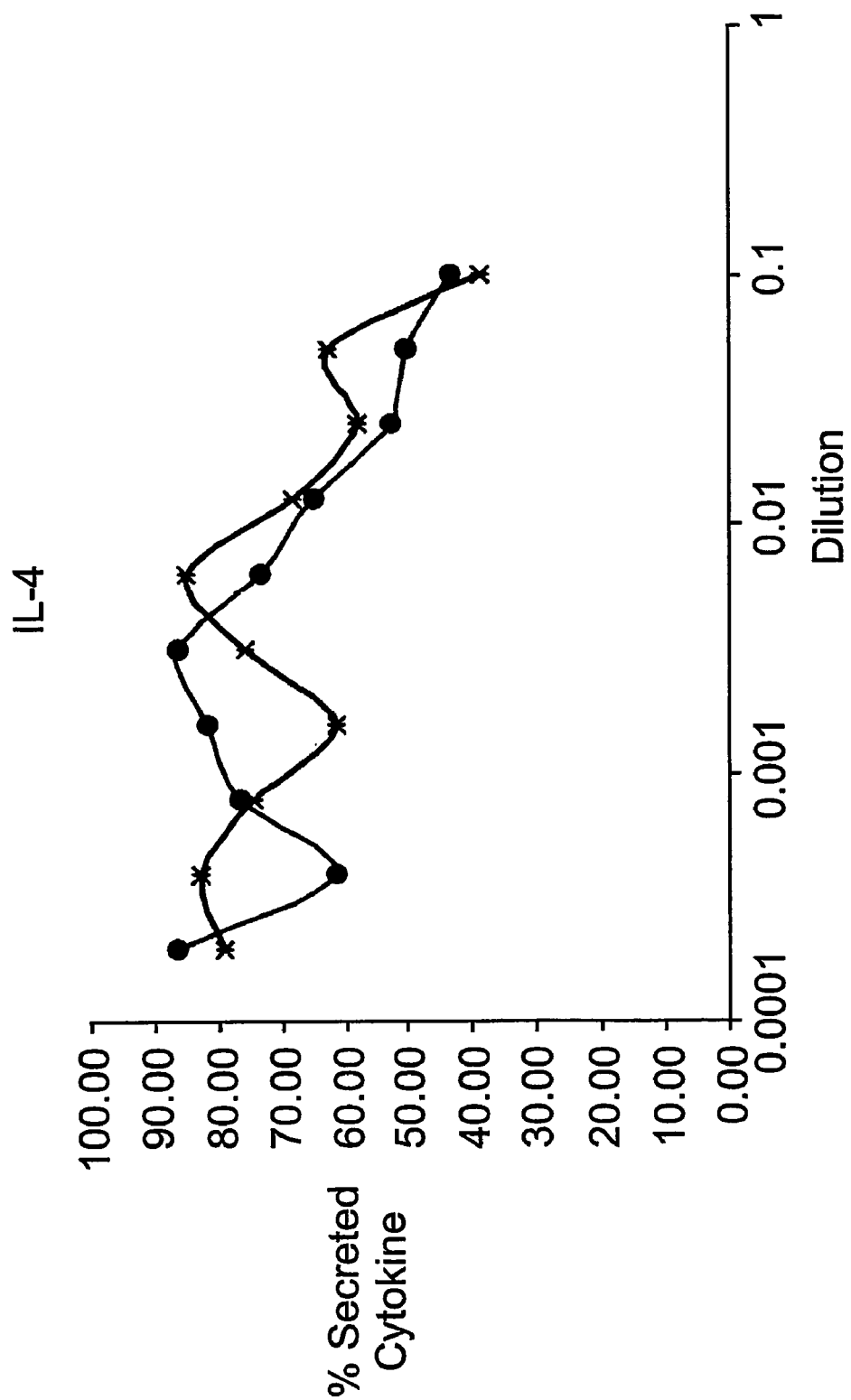

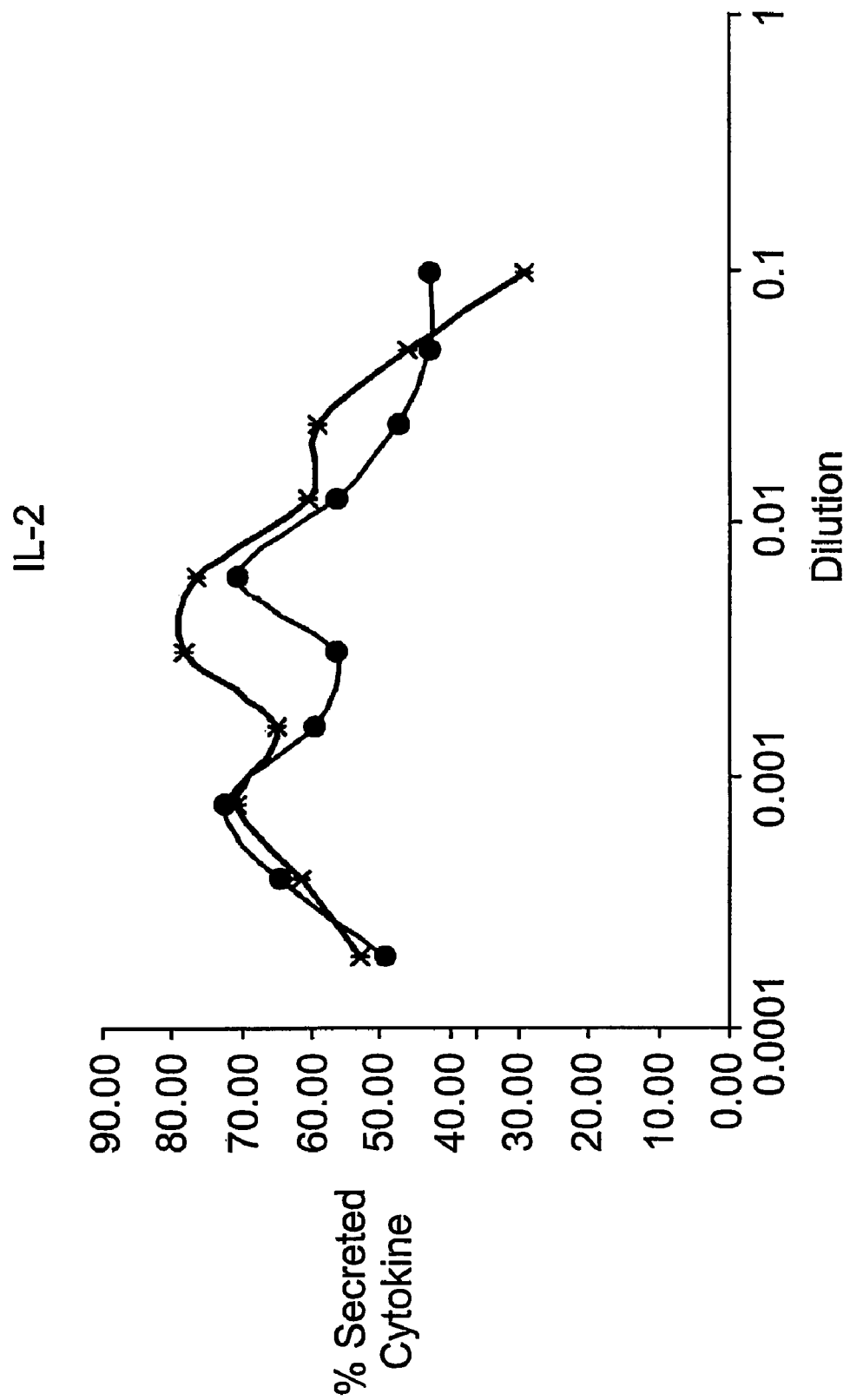

ALAT

ASAT

METHOD OF TREATMENT COMPRISING ADMINISTRATION OF A CYTOKINE ANTAGONIST MOLECULE

CROSS-REFERENCE TO RELATED APPLICATION

This application is the National Stage of International Application Number PCT/GB2004/004772, filed Nov. 12, 2004, which is hereby incorporated by reference herein in its entirety, including any figures, tables, nucleic acid sequences, amino acid sequences, or drawings.

This invention relates to novel proteins (termed INSP052 and INSP055), herein identified as immunoglobulin domain-containing cell surface recognition molecules and to the use of these proteins and nucleic acid sequences from the encoding genes in the diagnosis, prevention and treatment of disease, for instance in the diagnosis, prevention and treatment of inflammatory diseases, auto-immune diseases, skin diseases, liver disease or liver failure.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

Recently, a remarkable tool for the evaluation of sequences of unknown function has been developed by the Applicant for the present invention. This tool is a database system, termed the Biopendium search database, that is the subject of WO01/69507. This database system consists of an integrated data resource created using proprietary technology and containing information generated from an all-by-all comparison of all available protein or nucleic acid sequences.

The aim behind the integration of these sequence data from separate data resources is to combine as much data as possible, relating both to the sequences themselves and to information relevant to each sequence, into one integrated resource. All the available data relating to each sequence, including data on the three-dimensional structure of the encoded protein, if this is available, are integrated together to make best use of the information that is known about each sequence and thus to allow the most educated predictions to be made from comparisons of these sequences. The annotation that is generated in the database and which accompanies each sequence entry imparts a biologically relevant context to the sequence information.

This data resource has made possible the accurate prediction of protein function from sequence alone. Using conventional technology, this is only possible for proteins that exhibit a high degree of sequence identity (above about 20%-30% identity) to other proteins in the same functional family. Accurate predictions are not possible for proteins that exhibit a very low degree of sequence homology to other related proteins of known function.

Signal Peptide-Containing Proteins

The ability of cells to make and secrete extracellular proteins is central to many biological processes. Enzymes, growth factors, extracellular matrix proteins and signaling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of signal peptide containing proteins that play a central role in the functioning of a cell are cytokines, hormones, extracellular matrix proteins, adhesion molecules, receptors, proteases, and growth and differentiation factors.

Immunoglobulin Domain-Containing Cell Surface Recognition Molecules

Immunoglobulin domain-containing cell surface recognition molecules have been shown to play a role in diverse physiological functions, many of which can play a role in disease processes. Alteration of their activity is a means to alter the disease phenotype and as such identification of novel immunoglobulin domain-containing cell surface recognition molecules is highly relevant as they may play a role in many diseases, particularly inflammatory disease, oncology, and cardiovascular disease. Immunoglobulin domain-containing cell surface recognition molecules are involved in a range of biological processes, including: embryogenesis (Martin-Bermudo, M.D. et al, Development. 2000 127(12):2607-15; Chen, L. M., et al., J Neurosci. 2000 20(10):3776-84; Zweegman, S., et al, Exp Hematol. 2000 28(4):401-10; Darribere, T., et al., Biol Cell. 2000 92(1):5-25), maintenance of tissue integrity (Eckes, B., et al., J Cell Sci. 2000 113(Pt 13):2455-2462; Buckwalter, J. A., et al., Instr Course Lect. 2000 49:481-9; Frenette, P. S., et al.,. J Exp Med. 2000 191(8): 1413-22; Delmas, V., et al, Dev Biol. 1999 216(2):491-506; Humphries, M. J., et al., Trends Pharmacol Sci. 2000 21(1): 29-32; Miosge, N., et al, Lab Invest. 1999 79(12):1591-9; Nagaoka T, et al. Am J Pathol 2000 July 157:1 237-47; Nwariaku F E, et al. J Trauma 1995 39(2): 285-8; Zhu X, et al. Zhonghua Zheng Xing Shao Shang Wai Ke Za Zhi 1999 15(1): 53-5), leukocyte extravasation/inflammation (Lim, L. H., et al. Am J Respir Cell Mol Biol. 2000 22(6):693-701; Johnston, B., et al., Microcirculation. 2000 7(2):109-18; Mertens, A. V., et al., Clin Exp Allergy. 1993 23(10):868-73; Chcialowski, A., et al., Pol Merkuriusz Lek. 2000 7(43):13-7; Rojas, A. I., et al, Crit Rev Oral Biol Med. 1999 10(3):337-58; Marinova-Mutafchieva, L., et al., Arthritis Rheum. 2000 43(3):638-44; Vijayan, K. V., et al, J Clin Invest. 2000 105 (6):793-802; Currie, A. J., et al., J Immunol. 2000 164(7): 3878-86; Rowin, M. E., et al., Inflammation. 2000 24(2):157-73; Johnston, B., et al., J Immunol. 2000 164(6):3337-44; Gerst, J. L., et al., J Neurosci Res. 2000 59(5):680-4; Kagawa, T. F., et al., Proc Natl Acad Sci USA. 2000 97(5):2235-40;

Hillan, K. J., et al., Liver. 1999 19(6): 509-18; Panes, J., 1999 22(10):514-24; Arao, T., et al., J Clin Endocrinol Metab. 2000 85(1): 382-9; Souza, H. S., et al., Gut. 1999 45(6): 856-63; Grunstein, M. M., et al., Am J Physiol Lung Cell Mol Physiol. 2000 278(6):L1154-63; Mertens, A. V., et al., Clin Exp Allergy. 1993 23(10):868-73; Berends, C., et al., Clin Exp Allergy. 1993 23(11):926-33; Fernvik, E., et al., Inflammation. 2000 24(1):73-87; Bocchino, V., et al., J Allergy Clin Immunol. 2000 105(1 Pt 1):65-70; Jones S C, et al, Gut 1995 36(5):724-30; Liu C M, et al, Ann Allergy Asthma Immunol 1998 81(2):176-80; McMurray R W Sernin Artbritis Rheum 1996 25(4):215-33; Takahashi H, et al Eur J Immunol 1992 22(11): 2879-85; Carlos T, et al J Heart Lung Transplant 1992 11(6): 1103-8; Fabrega E, et al, Transplantation 2000 69(4): 569-73; Zohrens G, et al, Hepatology 1993 18(4): 798-802; Montefort S, et al. Am J Respir Crit Care Med 1994 149(5): 1149-52), oncogenesis (Orr, F. W., et al., Cancer. 2000 88(S12):2912-2918; Zeller, W., et al., J Hematother Stem Cell Res. 1999 8(5):539-46; Okada, T., et al., Clin Exp Metastasis. 1999 17(7):623-9; Mateo, V., et al., Nat Med. 1999 5(11):1277-84; Yamaguchi, K., et al., J Exp Clin Cancer Res. 2000 19(1):113-20; Maeshima, Y., et al, J Biol Chem. 2000 275(28):21340-8; Van Waes, C., et al., Int J Oncol. 2000 16(6):1189-95; Damiano, J. S., et al., Leuk Lymphoma. 2000 38(1-2):71-81; Seftor, R. E., et al., Cancer Metastasis Rev. 1999 18(3):359-75; Shaw, L. M., J Mammary Gland Biol Neoplasia. 1999 4(4): 367-76; Weyant, M. J., et al., Clin Cancer Res. 2000 6(3):949-56), angiogenesis (Koch A E, et al Nature 1995 376 (6540): 517-9; Wagener C & Ergun S. Exp Cell Res 2000 261(1): 19-24; Ergun S, et al. Mol Cell 2000 5(2): 311-20), bone resorption (Hartman G D, & Duggan M E. Expert Opin Investig Drugs 2000 9(6): 1281-91; Tanaka Y, et al. J Bone Miner Res 1995 10(10): 1462-9; Lark M W, et al. J Pharmacol Exp Ther 1999 291(2): 612-7; Raynal C, et al. Endocrinology 1996 137(6):2347-54; Ilvesaro J M, et al. Exp Cell Res 1998 242(1): 75-83), neurological dysfunction (Ossege L M, et al. Int Immunopharmacol 2001 1:1085-100; Bitsch A, et al, Stroke 1998 29:2129-35; Iadecola C & Alexander M. Curr Opin Neurol 2001 14:89-94; Becker K, et al Stroke 2001 32(1): 206-11; Relton J K, et al Stroke 2001 32(1): 199-205; Hamada Y, et al J Neurochem 1996 66:1525-31), thrombogenesis (Wang, Y. G., et al., J Physiol (Lond). 2000 526(Pt 1):57-68, Matsuno, H., et al., Nippon Yakurigaku Zasshi. 2000 115(3):143-50; Eliceiri, B. P., et al., Cancer J Sci Am. 2000 6(Suppl 3):S245-9; von Beckerath, N., et al., Blood. 2000 95(11):3297-301; Topol, E. J., et al., Am Heart J. 2000 139(6):927-33; Kroll, H., et al., Thromb Haemost. 2000 83(3):392-6), and invasion/adherence of bacterial pathogens to the host cell (Dersch P, et al. EMBO J 1999 18(5): 1199-1213).

The detailed characterisation of the structure and function of several immunoglobulin-domain containing cell surface recognition molecule families has led to active programs by a number of pharmaceutical companies to develop modulators for use in the treatment of diseases involving inflammation, oncology, neurology, immunology and cardiovascular function. Immunoglobulin domain containing cell surface recognition molecules are involved in virtually every aspect of biology from embryogenesis to apoptosis. They are essential to the structural integrity and homeostatic functioning of most tissues. It is therefore not surprising that defects in immunoglobulin domain containing cell surface recognition molecules cause disease and that many diseases involve modulation of immunoglobulin domain containing cell surface recognition molecule function. The members of this family are described below in Table 1.

The Immunoglobulin domain containing cell surface recognition molecule family in fact contains several distinct families. Of these families, some are of particular pharmaceutical interest due to small molecule tractability. They include:

1. The immunoglobulin adhesion molecules represent the counter receptors for the integrins and includes the intracellular adhesion molecules (ICAMs) and vascular cell adhesion molecules (VCAMs). Members are composed of variable numbers of globular, immunoglobulin-like, extracellular domains. Some members of the family, for example, PECAM-1 (CD31) and NCAM, mediate homotypic adhesion. Some members of the family, for example ICAM-1 and VCAM-1, mediate adhesion via interactions with integrins.

2. Cell surface growth factor receptors. Growth factors are extracellular and in order to exert a biological effect they interact with specific, high affinity receptors located on the plasma membranes of target cells. The molecular characterisation of a variety of different growth factor receptors revealed that they fall into defined families; the tyrosine kinase receptors, G-protein associated seven transmembrane receptors, and the serine/threonine kinase receptors. The tyrosine kinase receptors are characterised by an extracellular domain, a transmembrane domain, and an intracellular domain which possess tyrosine kinase activity. VEGFR, PDGFR, FGFR, CSF-1R and c-KIT are examples of tyrosine kinase growth factor receptors which also contain immunoglobulin domains in the extracellular portion. Dys-regulation of growth factor function results in many different disease phenotypes, including, but not exclusive to oncology (Bartucci M et al, (2001) Cancer Res. Sep 15;61(18):6747-54, Dias S et al., (2001) Proc Natl Acad Sci USA. Sep 11; 98(19):10857-62, Djavan B et al., (2001) World J Urol. 19(4):225-33), inflammation (Fiocchi C. (2001) J Clin Invest. Aug; 108(4):523-6, Hodge S et al., (2001) Respirology. Sep; 6(3):205-211, Fenwick S A et al., (2001) J Anat. Sep; 199(Pt 3):231-40), neurological (Cooper J D et al., (2001) Proc Natl Acad Sci USA 98(18): 10439-44, Fahnestock M et al, (2001) Mol Cell Neurosci 18(2):210-20), and metabolism (Vickers M H et al., (2001) Endocrinology. 142(9):3964-73).

TABLE 1

Immunoglubulin domain-containing cell surface recognition molecules

| Receptor | Ligand | Distribution |
| --- | --- | --- |
| ICAM-1 5 Ig domains | LFA-1 (CD11a/CD18) Mac-1 (CD11b/CD18), CD43 | Widespread, endothelial cells, fibroblasts, epithelium, monocytes, lymphocytes, dendritic cells, chondrocytes. |
| ICAM-2 2 Ig domains | LFA-1 (CD11b) | endothelial cells (high): lymphocytes, monocytes, basophils, platelets (low). |
| ICAM-3 5 Ig domains | LFA-1 (αd/CD18) | Lymphocytes, monocytes, neutrophils, eosinophils, basophils. |

TABLE 1-continued

Immunoglubulin domain-containing cell surface recognition molecules

| Receptor | Ligand | Distribution |
| --- | --- | --- |
| VCAM-1 6 or 7 Ig domains | α4β1, α4β7 | Endothelial cells, monocytes, fibroblasts, dendritic cells, bone marrow stromal cells, myoblasts. |
| LFA-3 6 Ig domains | CD2 | Endothelial cells, leukocytes, epithelial cells |
| PECAM-1 (CD31) | CD31, heparin | Endothelial cells (at EC-EC junctions), T cell subsets, platelets, neutrophils, eosinophils, monocytes, smooth muscle cells, bone marrow stem cells. |
| NCAM | NCAM, heparin $SO_4$ | Neural cells, muscle |
| MAdCAM-1 4 Ig domains | α4β7, L-selectin | Peyer's patch, mesenteric lymph nodes, mucosal endothelial cells, spleen. |
| CD2 | CD58, CD59, CD48 | T lymphocytes |
| VEGFR | VEGF | Widespread, retina, umbilical vein, adrenal, NT2 neuronal precursor cells |
| FGFR | FGF | Widespread, brain, colon, ovary |
| KIT | Stem Cell Factor, MGF | Widespread, foetus, melanocytes, gall bladder, cerebellum, gastric epithelium (low) |
| PDGFR | PDGF | Widespread, breast, placenta, fibroblast, lung, ovary, skin, heart |
| CSF-1R | CSF | Widespread, placenta, liver, multiple sclerosis lesions, spleen, lung, breast. |

Immunoglobulin domain-containing cell surface recognition molecules have thus been shown to play a role in diverse physiological functions, many of which can play a role in disease processes. Alteration of their activity is a means to alter the disease phenotype and as such identification of novel Immunoglobulin domain-containing cell surface recognition molecules is highly relevant as they may play a role in many diseases, particularly immunology, inflammatory disease, oncology, cardiovascular disease, central nervous system disorders and infection.

The Invention

The invention is based on the discovery that the INSP052 and INSP055 proteins function as immunoglobulin domain-containing cell surface recognition molecules, and more particularly, as cytokine antagonists. Examples of immunoglobulin domain-containing cell surface recognition molecules are listed in Table 1.

In one embodiment of the first aspect of the invention, there is provided a polypeptide which:
(i) comprises or consists of the amino acid sequence as recited in SEQ ID NO:2, SEQ ID NO:4, SEQ ID NO: 6, SEQ ID NO:8, SEQ ID NO:10, SEQ ID NO:12, SEQ ID NO:14, SEQ ID NO:16, SEQ ID NO:20, SEQ ID NO:22, SEQ ID NO:24, or SEQ ID NO:26;
(ii) is a fragment thereof having the activity of a polypeptide according to (i), or having an antigenic determinant in common with a polypeptide according to (i); or
(iii) is a finctional equivalent of (i) or (ii).

By "the activity of a polypeptide according to (i)", we refer to immunoglobulin domain-containing cell surface recognition molecule activity. By immunoglobulin domain-containing cell surface recognition molecule activity we refer to polypeptides that comprise amino acid sequence or structural features that can be identified as conserved features within the immunoglobulin domain-containing cell surface recognition molecule family.

Included within this definition is activity as a cytokine antagonist. By "cytokine antagonist" is meant that the polypeptide, fragment or functional equivalent inhibits the activity of at least one cytokine. Preferably, the cytokine antagonists of the invention may inhibit cytokine activity by inhibiting cytokine expression and/or secretion. Cytokine antagonists that inhibit cytokine expression by other mechanisms, for example by binding to a cytokine or to a cytokine receptor, are also included in the invention. Preferably, the cytokine antagonists of the invention are able to inhibit the activity of more than one cytokine.

Preferably, the cytokine antagonists of the invention have immunomodulatory activity. By "immunomodulatory activity" is meant any activity detected in vitro or in vivo that affects the immune response. Examples of immunomodulatory activities includes immunosuppressive activities, anti-inflammatory activities, pro-apoptotic activities, anti-apoptotic activities and anti-tumoral activities.

Cytokines which may be inhibited by the cytokine antagonists of the invention include: TGF-alpha; EGF; members of the four alpha-helical bundle family of cytokine (such as IL-2, IL-3, IL-4, IL-5, IL-6, IL-7, IL-9, IL-13, G-CSF, GM-CSF, CNTF, OSM, EPO, IL-10, IFN-alpha, IFN-beta, IFN-gamma and M-CSF); members of the cysteine knot family of cytokines (such as NGF, TGF-beta, PDGF and VEGF); chemokines (such as IL-8, MIP-1-alpha, MIP-1-beta, MIP-2, PF-4, PBP, I-309/TCA-3, MCP-1, MCP-2, MCP3 and IP-10), members of the TNF family of cytokines (such as TNF-alpha, TNF-beta and LT-beta); and members of the beta-trefoil family of cytokines including FGF-alpha, FGF-beta IL-1-alpha, IL-1-beta and IL-Ira). Preferred cytokine antagonists of the invention inhibit the activity of TNF-alpha, IL-4 and/or IL-2.

Cytokines form an heterogeneous family of secreted polypeptides, of relatively low molecular weight, acting as regulators of cellular reactions to various kind of stimuli, in particular those related to inflammatory and immune reactions but also those related to cell proliferation, repair, cell-cell interactions, and differentiation.

Cytokines are mainly represented by non-enzymatic glycoproteins that have been historically classified into several groups based on criteria such as sequence homology, structural elements, expressing cells, and/or binding activity. Examples of such families of sequences are Interleukins, Lymphokines, Monokines, Inteferons, but many other sequences have been characterized as having cytokine activities in the recent years (such as some growth factors or chemokines) making difficult to provide an exhaustive classification (Haddad J J, 2002, Biochem Biophys Res Commun, 297:700-13).

Cytokines are mostly produced by monocytes, macrophages and lymphocytes, but also by other cell types (such as leukocytes, osteoblasts, smooth muscle cells, epithelial cells, neuronal cells, endothelial cells, or fibroblasts), but they are not normally produced in a constitutive manner. Cytokines are generally secreted by immune cells in response to an offending agent (e.g. bacteria, virus, or other pathogens) that can stimulate their de novo expression and secretion from cells with the consequence of altering either their own functions (autocrine/intracrine effects) or those of adjacent cells and the local microenvironment (paracrine/juxtacrine effects).

Cytolines act on the target cell via receptors that trigger various cell signaling pathways. (Ishihara K and Hirano T, 2002, Biochim Biophys Acta, 1592: 281-296). Typically, the actions of cytokines are often pleiotropic (one cytokine may elicit several physiological effects), redundant (different cytokines may be responsible for a similar physiological effect), and may affect diverse and overlapping target cell populations.

The observed physiological effects of cytokines are due to fact that, in association to an inflammatory response leading to the mobilization and aggregation of cells, cytokines can induce (or suppress) the production of many proteins in a coordinate manner, including that of other cytokines and/or of cytokine receptors. Thus, many physiological responses (both under physiological and pathological conditions) are the result of inter-connected, redundant network of synergistic or antagonistic interactions amongst cytoldnes.

The cloning and biological analyses of cytokines and of their receptors have led to a general understanding of molecular basis behind their pleiotropism and redundancy. This property can be often ascribed to the composition of cytokine receptor complexes that include a signal-transducing receptor subunit that is used by all members of a cytokine family and a binding subunit that is specific for each cytokine. Thus, the cytokine-induced signalling cascade represents a mechanism having a final outcome for a particular cell or tissue that is determined by a number of different messages received concurrently at the cell surface.

The details of the functioning of the cytokine network are not yet fully understood, but it is clear that cytokines are important mediators and are implicated in the pathogenesis of numerous diseases, directly or indirectly related to both innate and adaptive immune responses. In particular, main patho-physiological effects of cytokines result from their excessive or inappropriately localized production, inducing an inflammatory state negatively affecting the state of a patient. Therefore, it is a generally acknowledged that any mechanism effectively inhibiting one or more cytokines, in particular proinflammatory cytokines, may have a positive effect in the treatment of human diseases by controlling the adverse cascade of cellular events associated to inappropriate or prolonged production of particular cytokines.

At this time, a wide range of strategies and compounds has been disclosed in the literature regarding technologies for generating and/or administering antagonists of cytokines blocking their proinflammatory activities. A non-exhaustive list of these technologies includes soluble variants of the human cytokine receptors, cytokine-specific antibodies, viral proteins binding cytokines, small molecules inhibiting cytokine production. These immunomodulating molecules can target inefficient or misdirected immune responses. However, there are relatively few cytokine antagonists available for the use in the treatment of human diseases. The potential of alternative compounds for pharmacological intervention in cytokine-mediated inflammatory processes by modulating extracellular or intracellular signaling pathways has not been thoroughly explored by drug discovery programs (Stevceva L, 2002, Curr Med Chem., 9: 2201-7; Inagaki-Ohara K et al., 2003, Curr Opin Pharmacol., 3: 435-42).

Evidence is presented in the Examples section below that the extracellular domain of INSP052 (also referred to herein as INSP052EC) downregulates TNF-alpha, IL-4 and IL-2 secretion in vitro in a Concanavalin A (ConA) stimulated human peripheral blood mononuclear cells (hPBMC) assay and in a similar assay using CD4+ T cells. In addition, delivery of INSP052EC cDNA in an in vivo model of fulminant hepatitis was found to decrease TNF-alpha and m-IL-6 levels in serum and had a significant effect on the reduction of transaminases measured in serum. This effect was confirmed by subcutaneous INSP052EC protein injections.

The decrease in aspartate aminotransferase (ASAT) and alanine aminotransferase (ALAT) levels noted might be due to both decreased TNF-alpha and IL-4 levels. TNF-alpha and IL-4 are important cytokines involved in liver damage induced after ConA injection. In this mouse model of liver hepatitis, TNF-alpha is mainly produced by hepatic macrophages, the so-called Kupfer cells, whereas IL-4 is produced by liver (natural killer T) NKT cells. Anti TNF-alpha antibodies have been shown to confer protection against disease (Seino et al. 2001, Annals of surgery 234, 681) and inhibition of IL-4 production by NKT cells was shown to be hepato-protective in T-cell mediated hepatitis in mouse (Ajuebor et al. 2003 J. Immunology 170, 5252-9).

Furthermore, in a model of LPS-induced cytokine release in mice, the potential of INSP052EC to down-regulate LPS-induced TNF alpha or IL-6 release was demonstrated.

Additionally, INSP052EC was tested on hapten-induced contact hypersensitivity (CHS), a murine model of inflammatory skin disease. We show that INSP052EC reduces ear swelling in a significant and dose-dependent manner, suggesting a decrease in leukocyte infiltration and of the consequent inflammation, so demonstrating that INSP052EC can be useful in treating T cell-mediated inflammation of the skin, such as in allergic contact dermatitis and psoriasis.

It is clearly shown herein that the isolated extracellular domain of INSP052 (INSP052EC) can be used (as such or as a variant or a fusion protein containing this protein sequence or the full length protein) for modulating cytokine activities, functioning in particular as an antagonist of cytokine secretion and/or expression, and may have a therapeutic role in diseases directly or indirectly related to both innate and adaptive immune responses. These results obtained with the extracellular domain of INSP052 allow us to infer that other variants of the INSP052 polypeptide, as well as the full length polypeptide sequence, are likely to share equivalent functions to those demonstrated. Accordingly, it is considered that INSP052, INSP052EC (SEQ ID NO.20 and SEQ ID NO.22) and related functionally equivalent proteins will be useful in treating auto-immune, viral or acute liver diseases as well as alcoholic liver failures. They are likely also to be effective in treating other inflammatory diseases.

The range of inhibiting activities shown by the tested INSP052EC-based molecule in different cell-based assays and animal models confirms that patho-physiological effects of cytokines resulting from their excessive or inappropriately localized production can be blocked by using this molecule. The control of cellular events associated with prolonged production of proinflammatory cytokines can be obtained by INSP052EC-based molecules, which therefore can be used for antagonizing abnormal inflammatory states associated, in particular, to autoimmune and inflammatory diseases affecting various tissues and organs (e.g. liver, skin, lungs, central nervous system), providing as well a new therapeutic opportunity for oncological, neurological, cardiovascular, and infectious disorders. Additional clinical applications for INSP052EC-based molecules can be identified by using cytokine assays showing the excessive expression and/or secretion of cytokines in samples obtained by patients affected by other diseases (Wong C K and Lam C W, Adv Clin Chem. 2003, 37:1-46; Whiteside T L, Biotechniques, 2002, Oct. Suppl:4-8, 10, 12-5), then justifying the therapeutic use of a cytokine antagonist as INSP052EC-based molecules.

The polypeptide having the sequence recited in SEQ ID NO:2 is referred to hereafter as "the INSP052 exon 1 polypeptide". The polypeptide having the sequence recited in SEQ ID NO:4 is referred to hereafter as "the INSP052 exon 2 polypeptide". The polypeptide having the sequence recited in SEQ ID NO:6 is referred to hereafter as "the INSP052 exon 3 polypeptide". The polypeptide having the sequence recited in SEQ ID NO:8 is referred to hereafter as "the INSP052 exon 4 polypeptide". The polypeptide having the sequence recited in SEQ ID NO:10 is referred to hereafter as "the INSP052 exon 5 polypeptide". The polypeptide having the sequence recited in SEQ ID NO:12 is referred to hereafter as "the INSP052 exon 6 polypeptide". The polypeptide having the sequence recited in SEQ ID NO:14 is referred to hereafter as "the INSP052 exon 7 polypeptide". Combining SEQ ID NO:2, SEQ ID NO:4, SEQ ID NO:6, SEQ ID NO:8, SEQ ID NO:10, SEQ ID NO:12 and SEQ ID NO:14 produces the sequence recited in SEQ ID NO:16. The polypeptide having the sequence recited in SEQ ID NO:16 is referred to hereafter as the INSP052 polypeptide. The polypeptide having the sequence recited in SEQ ID NO:20 is the extracellular domain of INSP052. The polypeptide having the sequence recited in SEQ ID NO:22 is referred to hereafter as the extracellular domain of the mature INSP052 polypeptide. The polypeptide having the sequence recited in SEQ ID NO:24 is referred to hereafter as the mature INSP052 exon 2 polypeptide. The polypeptide having the sequence recited in SEQ ID NO:26 is referred to hereafter as the mature INSP052 polypeptide. The polypeptide having the sequence recited in SEQ ID NO:29 is referred to hereafter as the histidine-tagged, extracellular domain of mature INSP052. The polypeptide having the sequence recited in SEQ ID NO:30 is referred to hereafter as the Fc fusion of the extracellular domain of mature INSP052. The polypeptide having the sequence recited in SEQ ID NO:31 is referred to hereafter as the Ig domain containing fragment of INSP052 (INSP052Ig2).

The term "INSP052 exon polypeptides" as used herein includes polypeptides comprising or consisting of the polypeptide sequences set forth herein, including the INSP052 exon 1 polypeptide, the INSP052 exon 2 polypeptide, the INSP052 exon 3 polypeptide, the INSP052 exon 4 polypeptide, the INSP052 exon 5 polypeptide, the INSP052 exon 6 polypeptide, the INSP052 exon 7 polypeptide, the INSP052 polypeptide, the extracellular domain of INSP052, the extracellular domain of mature INSP052, the INSP052 mature exon 2 polypeptide, the mature INSP052 polypeptide, the histidine-tagged, extracellular domain of mature INSP052, the Fc fusion of the extracellular domain of mature INSP052 and the Ig domain containing fragment of INSP052.

In one embodiment, the polypeptide according to this embodiment consists of the amino acid sequence recited in SEQ ID NO:16 (the INSP052 polypeptide) or is a fragment of or functional equivalent thereof. In another embodiment, the polypeptide consists of the amino acid sequence recited in any one of SEQ ID NO:2, SEQ ID NO:4, SEQ ID NO:6, SEQ ID NO:8, SEQ ID NO:10, SEQ ID NO:12, or SEQ ID NO:14, or is a variant thereof.

In a further embodiment of the first aspect of the invention there is provided a polypeptide which:
i) comprises or consists of the amino acid sequence as recited in SEQ ID NO:20 or SEQ ID NO:22;
ii) is a fragment thereof having the activity of a polypeptide according to (i), or having an antigenic determinant in common with a polypeptide according to (i); or
iii) is a functional equivalent of (i) or (ii).

The amino acid sequence recited in SEQ ID NO:20 represents the extracellular domain of INSP052 and corresponds to amino acids 1-240 of the full length protein (see the Examples section). SEQ ID NO:22 represents the extracellular domain of mature INSP052. See also FIG. 7 for the extracellular domain of INSP052.

It is considered highly likely that the extracellular domain will fold correctly and show biological activity if additional residues C terminal and/or N terminal of these boundaries in the polypeptide sequence are included in the polypeptide fragment. For example, an additional 5, 10, 20, 30, 40, 50 or even 100 amino acid residues from the INSP052 polypeptide sequence, or from a homologous sequence, may be included at either or both the C terminal and/or N terminal of the boundaries of the receptor binding domain, without prejudicing the ability of the polypeptide fragment to fold correctly and exhibit biological activity. Extensions as large as 100 or 200 residues may be necessary due to the presence of large loops between secondary structural elements.

For truncated variants of the INSP052 extracellular domain, one or a few amino acid residues (for example, 2, 3, 4, 5, 10, 15, 20, 25, 30 or more) may be deleted at either or both the C terminus or the N terminus of the domain without prejudicing biological activity.

A preferred truncated variant of the INSP052 extracellular domain is the Ig domain containing fragment of INSP052 (INSP052Ig2) having the sequence shown in SEQ ID NO:31. The invention provides a polypeptide which: (i) comprises or consists of the amino acid sequence as recited in SEQ ID NO:31; is a fragment thereof having the activity of a polypeptide according to (i), or having an antigenic determinant in common with a polypeptide according to (i); or is a functional equivalent of (i) or (ii).

As discussed below, the polypeptides of the invention may be provided in the form of a fusion protein or as "free-standing" protein. Accordingly, one embodiment of the invention provides a polypeptide which consists of the extracellular domain of INSP052. Another embodiment of the invention provides a polypeptide which consists of INSP052 (the full length protein or the extracellular domain thereof, including the mature version and truncated variants thereof) fused with at least one other polypeptide to form a fusion protein.

Accordingly, still further embodiments of the present invention include a polypeptide, which polypeptide comprises or consists of two sequences (a) and (b), wherein:
a) is an amino acid sequence at least 90% identical to:
   (i) the amino acid sequence as recited in SEQ ID NO:20, SEQ ID NO:22 or SEQID NO:31;
   (ii) is a fragment thereof having the activity of a polypeptide according to (i), or having an antigenic determinant in common with a polypeptide according to (i); or
   (iii) is a functional equivalent of (i) or (ii); and
b) is an heterologous amino acid sequence chosen from the group of: a signal sequence, purification tag, the extracellular domain of a membrane-bound protein, a secreted protein, a starting Methionine, a linker region containing a recognition site for an endopeptidase, or the Fc region from an immunoglobulin molecule.

Such fusion proteins can be obtained by cloning a polynucleotide encoding a polypeptide comprising a sequence having at least 90% homology with any one of the INSP052 polypeptides described above over the length of the polypeptide, preferably at least 95% at least 97% at least 98% or at least 99% homology, in frame with the coding sequences for a heterologous protein sequence.

The term "heterologous", when used herein, is intended to designate any polypeptide other than a human INSP052 polypeptide. Examples of heterologous sequences, that can be comprised in the fusion proteins either at the N- or C-terminus, include: extracellular domains of membrane-bound protein, immunoglobulin constant regions (Fc regions), multimerization domains, domains of extracellular proteins, signal sequences, export sequences, and sequences allowing purification by affinity chromatography.

Many of these heterologous sequences are commercially available in expression plasmids since these sequences are included in fusion proteins in order to provide additional properties without significantly impairing the specific biological activity of the protein fused to them (Terpe K, 2003, Appl Microbiol Biotechnol, 60:523-33).

Examples of such additional properties are a longer lasting half-life in body fluids, an easier purification procedure, an additional binding moiety, maturation by means of an endoproteolytic digestion, increased stability during recombinant production, or extracellular localization. This latter feature is of particular importance since it allows the, polypeptides to be localized in the space where the isolation and purification of these polypeptides is facilitated.

Design of the moieties, ligands, and linkers, as well methods and strategies for the construction, purification, detection, maturation, and use of fusion proteins are widely discussed in the literature (Nilsson J et al., Protein Expr Purif, 11: 1-16, 1997; "Applications of chimeric genes and hybrid proteins" Methods Enzymol. Vol. 326-328, Academic Press, 2000).

If needed, the heterologous sequence can be eliminated by a proteolytic cleavage after purification of the protein or in vivo. This can be achieved, for example, by inserting a proteolytic cleavage site between the protein and the heterologous sequence, and exposing the fusion protein to the appropriate endo-/exopeptidase. These features facilitate the production of fusion proteins and their use in the preparation of pharmaceutical compositions.

For example, the heterologous sequence can be linked to the protein by linker sequence containing a recognition site for an endopeptidase (such as a caspase) that can be used to detach the desired protein from the heterologous sequence either in vivo or in vitro.

Alternatively, if the protein to be expressed does not contain a start methionine (e.g. if it a mature sequence without the signal peptide), the heterologous sequence may be a start methionine to allow correct expression in the host cell. This additional amino acid may be eliminated subsequently by means of an exopeptidase, such as Methionine Aminopeptidase, according to methods disclosed in the literature (Van Valkenburgh H A and Kahn R A, Methods Enzymol, 344: 186-193, 2002; Ben-Bassat A, BioProccess Technol, 12:147-159, 1991).

The heterologous sequences to which the polypeptides of the invention may be fused may consist of sequences that facilitate the secretion of the protein, such as signal peptides and export signals (Rapoport T A et al., Annu Rev Biochem. 1996; 65:271-303).

Alternatively, the heterologous sequence in the fusion protein may enable easier purification of the protein. For example, the INSP052 polypeptide may be purified by means of a hexa-histidine peptide fused at the C-terminus of INSP052. An example of such a fusion polypeptides is presented in SEQ ID NO:29. This hexa-histidine peptide forms a so-called "histidine tag" which facilitates purification (Gentz et al. 1989, Proc Natl Acad Sci USA, 86:821-4). A "HA" tag, an epitope derived from the influenza hemagglutinin protein (Wilson et al. 1994, Cell, 37:767-78) or other affinigity purification tags such as GST, FLAG or MBP may be used in place of the histidine tag.

The heterologous sequence of the fusion protein may provide a further functional activity. For example, the extracellular domain of INSP052 which has cytokine antagonist activity may be fused with a heterologous sequence which also has anti-inflammatory or, in general, immunomodulatory activity such as further cytokine antagonists, collagen II-binding agents (such as those disclosed in WO01/37861) and cytokines themselves (such as those disclosed in WO03/095488, WO03/014359 and WO03/035105).

The heterologous sequence may provide better stability, prolonging the half-life of a polypeptide of the invention and thereby improving its therapeutic activity. For example, the polypeptides may be fused to human serum albumin, or to other sequences that bind to circulating human serum albumin (see Chuang V T et al., Pharm Res. 2002; 19: 569-577; Graslund T et al., Protein Expr Purif. 1997, 9: 125-32; WO 01/77137). Alternatively, the additional sequence may help the targeting to specific localization, such as in the brain (WO 03/32913).

The heterologous sequence may improve stability by allowing the formation of multimers of the protein. Examples of heterologous sequences promoting multimerisation include domains isolated from proteins such hCG (WO 97/30161), collagen X (WO 04/33486), C4BP (WO 04/20639), Erb proteins (WO 98/02540), or coiled coil peptides (WO 01/00814).

In a preferred embodiment, the polypeptide is fused to the constant region of an Ig molecule. An example of such a polypeptide is presented in SEQ ID NO:30. Preferably, the polypeptide is fused to a heavy chain region, like the CH2 and CH3 domains of human IgG1, for example. Other isoforms of Ig molecules are also suitable for the generation of fusion proteins according to the present invention, such as isoforms IgG2 or IgG4, or other Ig classes, like IgM or IgA, for example. The constant region promotes stability by promoting multimerisation. Fusion proteins may be monomeric or multimeric, hetero- or homomultimeric.

Examples of strategies for generating fusion proteins comprising a protein and an immunoglobulin fragment are disclosed in the literature (WO 91/08298; WO 96/08570; WO 93/22332; WO 04/085478; WO 01/03737, WO 02/66514).

For example, the nucleic acid sequence encoding the mature INSP052 extracellular domain can be cloned in an expression vector fused to a nucleic acid sequence encoding the original INSP052 signal sequence (or any other appropriate signal/export sequence) at its 5' end, and the nucleic acid sequence encoding the constant region of human immunoglobulin lambda heavy chain IgG1 (NCBI Acc. No. CAA75302; segment 246-477) at its 3' end. The resulting vector can be used to transform a CHO or HEK293 host cell line and the clones stably expressing and secreting the recombinant fusion protein having the INSP052 extracellular domain at the N-terminus and the IgG1 sequence at the C-terminus can be selected. This clone then can be used for scaling up the production and for purifying the recombinant fusion protein from the culture medium. Alternatively, the position of the nucleic acid encoding the constant region of human immunoglobulin lambda heavy chain IgG1 and INSP052 extracellular domain can be inversed, and the resulting protein can be expressed and secreted using still the original signal sequence of INSP052, or any other appropriate signal/export sequence.

It is also possible to generate heterodimers using this technology by coexpressing constructs encoding two different fusion proteins in the same cell (WO00/18932). For example, a cell may express a first fusion protein comprising the INSP052 extracellular domain fused to an Fc domain and a second fusion protein comprising a an Fc domain fused to a protein with different activity, such as a further cytokine antagonist, a collagen II-binding agent (such as those disclosed in WO01/37861) and or a cytokine (such as those disclosed in WO03/095488, WO03/014359 and WO03/035105).

When the fusion protein comprises an immunoglobulin region, the fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the sequence of the substances of the invention and the immunoglobulin sequence. The resulting fusion protein has improved properties, such as an extended residence time in body fluids (ie. an increased half-life), increased specifi,c activity, increased expression level, or the purification of the fusion protein is facilitated.

In a further preferred embodiment, at least one moiety is attached to one or more functional groups within the polypeptide of the invention which occur as one or more side chains on the amino acid residues. The moiety is preferably a stabilizing polymer that allows the formation of conjugates and complexes (Harris J M and Chess R B; Nat Rev Drug Discov, 2: 214-221, 2003; Greenwald R B et al., Adv Drug Deliv Rev, 55: 217-250, 2003; Pillai O and Panchagnula R, Cur Opin Chem Biol, 5: 447-451, 2001). The polymer may be produced following a site-directed modification of an appropriate residue, in an internal or terminal position. Amino acid residues within the polypeptide or fusion protein can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment.

For example, an additional cysteine allowing direct PEGylation can be added at the N- or C-terminus of the extracellular domain of INSP052. Alternatively, a cysteine may be included in the protein by the substitution of a residue, for example in correspondence of a glycosylation site. Moreover, the side chains of the genetically encoded amino acids can be chemically modified for polymer attachment, or unnatural amino acids with appropriate side chain functional groups can be employed. Polymers may also be attached to a carbohydrate or other moiety that is attached to the side chain of the amino acid at the target position.

Polymers suitable for these purposes are non-toxic to biological systems. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, polyorthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly(N-vinyl pyrrolidone), polyalkylenes, polyacrylamide, and copolymers thereof. Preferred polymers comprise as a sequential repeat unit ethylene oxide, such as polyethylene glycol (PEG). The preferred method of attachment employs a combination of peptide synthesis and chemical ligation. Advantageously, the attachment of a water-soluble polymer will be through a biodegradable linker, especially at the amino-terminal region of a protein. Such modification acts to provide the protein in a precursor (or "pro-drug") form, that, upon degradation of the linker releases the protein without polymer modification.

In a second aspect, the invention provides a purified nucleic acid molecule which encodes a polypeptide of the first aspect of the invention.

Preferably, the purified nucleic acid molecule comprises or consists of the nucleic acid sequence as recited in SEQ ID NO:1 (encoding the INSP052 exon 1 polypeptide), SEQ ID NO:3 (encoding the INSP052 exon 2 polypeptide), SEQ ID NO:5 (encoding the INSP052 exon 3 polypeptide), SEQ ID NO:7 (encoding the INSP052 exon 4 polypeptide), SEQ ID NO:9 (encoding the INSP052 exon 5 polypeptide), SEQ ID NO:11 (encoding the INSP052 exon 6 polypeptide), SEQ ID NO:13 (encoding the INSP052 exon 7 polypeptide), SEQ ID NO:15 (encoding the INSP052 polypeptide), SEQ ID NO:17 (encoding the INSP055 polypeptide), SEQ ID NO:20 (encoding the extracellular domain of the INSP052 polypeptide), SEQ ID NO:22 (encoding the extracellular domain of the INSP052 mature polypeptide), SEQ ID NO:24 (encoding the mature INSP052 exon 2 polypeptide), SEQ ID NO:26 (encoding the mature INSP052 polypeptide) or is a redundant equivalent or fragment of any one of these sequences.

Combining the sequences recited in SEQ ID NO:1, SEQ ID NO:3, SEQ ID NO:5, SEQ ID NO:7, SEQ ID NO:9, SEQ ID NO:11 and SEQ ID NO:13 produces the sequence recited in SEQ ID NO:15.

Combining the sequences recited in SEQ ID NO:23, SEQ ID NO:5, SEQ ID NO:7, SEQ ID NO:9, SEQ ID NO:11 and SEQ ID NO:13 produces the sequence recited in SEQ ID NO:25.

In one embodiment of the second aspect of the invention there is provided a nucleic acid molecule which encodes a polypeptide which comprises or consists of the extracellular domain of INSP052 (SEQ ID NO:20). Preferably, the nucleic acid molecule comprises or consists of the nucleic acid sequence set forth in SEQ ID NO:19. This is also set out in FIG. 7 of co-pending patent application WO03/093316, although these sequences include histidine residues added to the C terminal.

In one embodiment of the second aspect of the invention there is provided a nucleic acid molecule which encodes a polypeptide which comprises or consists of the extracellular domain of mature INSP052 (SEQ ID NO:22). Preferably, the nucleic acid molecule comprises or consists of the nucleic acid sequence set forth in SEQ ID NO:21. This is also set out in FIG. 7 of co-pending patent application WO03/093316, although these sequences include histidine residues added to the C terminal.

In one embodiment of the second aspect of the invention there is provided a nucleic acid molecule which encodes a polypeptide which comprises of consists of the variant of the extracellular domain of mature INSP052 which is the Ig-domain containing fragment of INSP052 (SEQ ID NO:31).

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to, and which preferably inhibits the activity of a polypeptide of the first aspect of the invention. The skilled person will understand that the term "ligand" encompasses any moiety that binds specifically to the polypeptide of the first aspect of the invention including, for example, antibodies and orphan receptors.

By "the activity of a polypeptide of the invention" and similar expressions, we refer to activity characteristic of immunoglobulin domain-containing cell surface recognition molecules. In particular, included within this definition is activity as a cytokine antagonist as defined above, particularly as an antagonist of cytokine expression and/or secretion, particularly with respect to TNF-alpha, IL4 and IL-2. Preferably, the cytokine antagonists of the invention have immunomodulatory activity. An example of a utility of the polypeptides of the invention in this respect is in the treatment of T cell-mediated inflammation of the skin, such as in allergic contact dermatitis and psoriasis.

Methods for identification of ligands according to the sixth aspect of the invention are described in detail below. In particular, the invention provides a method for the identification of a compound that is a ligand that binds specifically to the polypeptides of SEQ ID NO:20 or SEQ ID NO:22, comprising contacting a polypeptide according to the first aspect of the invention with one or more compounds suspected of possessing binding affinity for said polypeptide and selecting a compound that binds specifically to said polypeptide. Ligands of the polypeptides of the invention identified by such methods may be used to identify further cytokine antagonists. For example, screening methods may be contacted to identify compounds that bind to such ligands, such as antibodies, which may also act as cytoline antagonists.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide.

Importantly, the identification of the function of the INSP052 and INSP055 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

Evidence is presented in the Examples section below that the extracellular domain of INSP052 may be used to prevent or treat inflammatory diseases, auto-immune diseases, skin disease, liver disease and liver failure. Accordingly, the provision of a compound according to the seventh aspect of the invention which mimics extracellular domain of INSP052 conformationally, or is an agonist of the extracellular domain of INSP052 is particularly preferred since such a compound may find utility in the prevention or treatment of an inflammatory disease, an auto-immune disease, liver disease or liver failure as described above.

In an eighth aspect, the invention provides a polypeptide of the first aspect of the invention, or a nucleic acid molecule of the second or third aspect of the invention, or a vector of the fourth aspect of the invention, or a host cell of the fifth aspect, or a ligand of the sixth aspect of the invention, or a compound of the seventh aspect of the invention, for use in therapy or diagnosis, preferably in relation to inflammatory diseases, auto-immune diseases, skin disease, liver disease (including viral or acute liver disease) and liver failure (including alcoholic liver failure).

The moieties of the first, second, third, fourth, fifth and sixth aspects of the invention may also be used in the manufacture of a medicament for the prevention or treatment of diseases including, but not limited to, cell proliferative disorders, autoimmune/inflammatory disorders, cardiovascular disorders, neurological and psychiatric disorders, developmental disorders, genetic disorders, metabolic disorders, infections and other pathological conditions.

These diseases preferably include neoplasm, cancer, brain tumour, glioma, bone tumor, lung tumor, breast tumour, prostate tumour, colon tumour, hemangioma, myeloproliferative disorder, leukemia, hematological disease, neutropenia, thrombocytopenia, angiogenesis disorders, dermatological disease, ageing, wounds, burns, fibrosis, cardiovascular disease, restensosis, heart disease, peripheral vascular disease, coronary artery disease, oedema, thromboembolism, dysmenorrhea, endometriosis, pre-eclampsia, lung disease, COPD, asthma bone disease, renal disease, glomerulonephritis, liver disease, Crohn's disease, gastritis, ulcerative colitis, ulcer, immune disorder, autoimmune disease, arthritis, rheumatoid arthritis, psoriasis, epidermolysis bullosa, systemic lupus erythematosus, ankylosing spondylitis, Lyme disease, multiple sclerosis, neurodegeneration, stroke, brain/spinal cord injury, Alzheimer's disease, Parkinson's disease, motor neurone disease, neuromuscular disease, HIV, AIDS, cytomegalovirus infection, fimgal infection, ocular disorder, macular degeneration, glaucoma, diabetic retinopathy, ocular hypertension and other conditions in which immunoglobulin domain containing cell surface recognition molecules, particularly cytokine antagonists, are implicated.

It is particularly preferred that the moieties of the first, second, third, fourth, fifth and sixth aspects of the invention are used in the manufacture of a medicament for the treatment of inflammatory diseases, auto-immune diseases, skin disease, liver disease (including viral or acute liver disease) and liver failure (including alcoholic liver failure).

The moieties of the first, second, third, fourth, fifth and sixth aspects of the invention may be used in combination with other therapeutic agents to treat the diseases listed above. In particular, the polypeptides of the invention (including fusion proteins) which have cytokine antagonist activity may be used in combination with a further therapeutic agent.

The invention therefore provides the use of i) a moiety of the first, second, third, fourth, fifth and sixth aspects of the invention, in particular a polypeptide or a fusion protein comprising the extracellular domain of INSP052 and ii) a further therapeutic agent, in the manufacture of a medicament for treating diseases or conditions in which cytokines, preferably TNF, IL-2 and/or IL-4, are implicated. Preferably, the disease or condition is selected from inflammatory diseases, auto-immune diseases, skin disease, liver disease (including viral or acute liver disease) and liver failure (including alcoholic liver failure).

The further therapeutic agent may antagonise the same cytokine as the polypeptides of the invention or may antagonise another moiety in the physiological pathway causing the disease or alleviate symptoms caused by the disease.

Preferably, the therapeutic agent is a cytokine antagonist (preferably an antagonist of TNF, IL-2 and/or IL-4), or an anti-inflammatory agent.

Examples of cytokine antagonists which may be used as further therapeutic agents include TNF-alpha antagonists such as etanercept, infliximab TNF alpha converting enzyme inhibitor (TACE inhibitor), and leflunomide used in the treatment of rheumatoid arthritis; and IL-2 antagonists such as basilimab and daclizumab used in the prevention of graft rejection. The further therapeutic agent may also be an anti-inflammatory agent such as a steroid or non-steroidal anti-inflammatory or may be another agent already used in the treatment of auto-immune disease, skin disease, liver disease or liver failure.

The additional therapeutic agent may be administered to the patient at the same time as the moiety of the first, second, third, fourth, fifth and sixth aspects of the invention, i.e. as a mixture. Alternatively, the moiety of the first, second, third, fourth, fifth and sixth aspects of the invention may be administered to a patient who has already received the therapeutic agent or the therapeutic agent may be administered to a patient who has already received the moiety of the first, second, third, fourth, fifth and sixth aspects of the invention. The combination may thus be for simultaneous, sequential or separate administration.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro.

Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

Preferably, the disease diagnosed by a method of the ninth aspect of the invention is a disease in which immunoglobulin domain-containing cell surface recognition molecules are implicated, as described above.

A preferred disease diagnosed by a method of the ninth aspect of the invention is an inflammatory disease, auto-immune disease, skin disease, liver disease (including viral or acute liver disease) or liver failure (including alcoholic liver failure).

In a tenth aspect, the invention provides for the use of the polypeptides of the first aspect of the invention as immunoglobulin domain-containing cell surface recognition molecules. The importance of the Ig domain in cell surface receptors is described in Lokker N A et al., "Functional importance of platelet-derived growth factor (PDGF) receptor extracellular immunoglobulin-like domains. Identification of PDGF binding site and neutralizing monoclonal antibodies," *J Biol Chem* 1997 Dec. 26; 272(52):33037 -44.

The invention provides for the use of the polypeptides of the first aspect of the invention as cytokine antagonists, as described above, particularly antagonists of TNF-alpha, IL-4 and IL-2 secretion. In this respect, the polypeptides of the invention may act as antagonists of cytokines, by lowering levels of cytokine expression, levels of cytokine activity, levels of cytokine secretion and so on.

The invention also provides for the use of a nucleic acid molecule according to the second or third aspects of the invention to express a protein that possesses immunoglobulin domain-containing cell surface recognition molecule activity. The invention also provides a method for effecting immunoglobulin domain-containing cell surface recognition molecule activity, said method utilising a polypeptide of the first aspect of the invention.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

According to one embodiment of the eleventh aspect of the invention, the pharmaceutical composition of the invention may additionally comprise a further therapeutic agent. The further therapeutic agent may antagonise the same cytokine as the polypeptides of the invention or may antagonise another moiety in the physiological pathway causing the disease or alleviate symptoms caused by the disease.

Preferably, the therapeutic agent is a cytokine antagonist (preferably an antagonist of TNF, IL-2 and/or IL-4), or an anti-inflammatory agent.

Examples of cytokine antagonists which may be used as further therapeutic agents include TNF-alpha antagonists such as etanercept, infliximab TNF alpha converting enzyme inhibitor (TACE inhibitor), and leflunomide used in the treatment of rheumatoid arthritis; and IL-2 antagonists such as basilimab and daclizumab used in the prevention of graft rejection. The further therapeutic agent may also be an anti-inflammatory agent such as a steroid or non-steroidal anti-inflammatory or may be another agent already used in the treatment of auto-immune disease, skin disease, liver disease or liver failure.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis. These molecules may also be used in the manufacture of a medicament for the treatment of diseases including, but not limited to, cell proliferative disorders, autoimmune/inflammatory disorders, cardiovascular disorders, neurological and psychiatric disorders, developmental disorders, genetic disorders, metabolic disorders, infections and other pathological conditions. These diseases preferably include neoplasm, cancer, brain tumour, glioma, bone tumor, lung tumor, breast tumour, prostate tumour, colon tumour, hemangioma, myeloproliferative disorder, leukemia, hematological disease, neutropenia, thrombocytopenia, angiogenesis disorders, dermatological disease, ageing, wounds, burns, fibrosis, cardiovascular disease, restensosis, heart disease, peripheral vascular disease, coronary artery disease, oedema, thromboembolism, dysmenorrhea, endometriosis, pre-eclampsia, lung disease, COPD, asthma bone disease, renal disease, glomerulonephritis, skin disease, liver disease, Crohn's disease, gastritis, ulcerative colitis, ulcer, immune disorder, autoimmune disease, arthritis, rheumatoid arthritis, psoriasis, epidermolysis bullosa, systemic lupus erythematosus, ankylosing spondylitis, Lyme disease, multiple sclerosis, neurodegeneration, stroke, brain/spinal cord injury, Alzheimer's disease, Parkinson's disease, motor neurone disease, neuromuscular disease, HIV, AIDS, cytomegalovirus infection, fungal infection, ocular disorder, macular degeneration, glaucoma, diabetic retinopathy, ocular hypertension and other conditions in which immunoglobulin domain containing cell recognition molecules are implicated.

It is particularly preferred that the moieties of the first, second, third, fourth, fifth and sixth aspects of the invention are used in the manufacture of a medicament for the treatment of an inflammatory disease, an auto-immune disease, liver disease or liver failure.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

Preferably, the disease is a disease in which immunoglobulin domain-containing cell surface recognition molecules are implicated, as described above.

It is particularly preferred that the disease is an inflammatory disease, an auto-immune disease, liver disease or liver failure.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

Preferably, the disease is a disease in which immunoglobulin domain-containing cell surface recognition molecules are implicated, as described above.

It is particularly preferred that the disease is an inflammatory disease, an auto-immune disease, liver disease or liver failure.

It should be appreciated that the scope of protection sought for the polypeptides and nucleic acids of the present invention does not extend to nucleic acids or polypeptides present in their natural source. Rather, the polypeptides and nucleic acids claimed by the present invention may be regarded as being "isolated" or "purified". The terms "isolated" and "purified" as used herein refer to a nucleic acid or polypeptide separated from at least one other component (e. g., nucleic acid or polypeptide) present with the nucleic acid or polypeptide in its natural source. Thus, for example, a polypeptide contained in a tissue extract would constitute an "isolated" or "purified" polypeptide, as would a polypeptide synthetically or recombinantly produced. In one embodiment, the nucleic acid or polypeptide is found in the presence of (if anything) only a solvent, buffer, ion, or other component normally present in a solution of the same.

It should be noted that the terms "isolated" and "purified" do not denote the method by which the polypeptide or nucleic acid is obtained or the level of purity of the preparation. Thus, such isolated or purified species may be produced recombinantly, isolated directly from the cell or tissue of interest or produced synthetically based on the determined sequences.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D.M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Such fusion proteins can be obtained by cloning a polynucleotide encoding a polypeptide comprising a sequence having at least 85% homology with an INSP052 polypeptide in frame with the coding sequences for a heterologous protein sequence.

The term "heterologous", when used herein, is intended to designate any polypeptide other than a human INSP052 polypeptide. Examples of heterologous sequences, that can be comprised in the fusion proteins either at the N- or C-terminus, are described above and include: extracellular domains of membrane-bound protein, immunoglobulin constant regions (Fc regions), multimerization domains, domains of extracellular proteins, signal sequences, export sequences, and sequences allowing purification by affinity chromatography. If needed, the heterologous sequence can be eliminated by a proteolytic cleavage, as described above.

In a preferred embodiment, the protein is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms IgG2 or IgG4, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA).

These alterations are intended to provide the polypeptides of the invention with improved purification, potency and/or pharmacokinetics features. For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4 -dinitrophenyl may also be used to modify the polypeptides of the invention.

Many other modifications providing increased potency, prolonged activity, ease of purification, and/or increased half-life, and techniques for the synthesis and the development of peptide mimetics are known in the art (WO 02/10195; Villain M et al., Chem Biol, 8: 673-679, 2001; Hruby V J and Balse P M, Curr Med Chem, 7: 945 -970, 2000; Golebiowski A et al., Curr Opin Drug Discov Devel, 4: 428-34, 2001). Various methodologies for incorporating unnatural amino acids into proteins, using both in vitro and in vivo translation systems, to probe and/or improve protein structure and function are also disclosed in the literature (Dougherty D A, Curr Opin Chem Biol, 4: 645-52, 2000).

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP052 and INSP055 polypeptides, preferably the INSP052 extracellular domain (i.e. SEQ ID NO:20 or SEQ ID NO:22). Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP052 and INSP055 polypeptides, preferably of the INSP052 extracellular domain. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP052 and INSP055 polypeptides, or with active fragments thereof, of greater than 80%. More preferred polypeptides have degrees of identity of greater than 85%, 90%, 95%, 98% or 99%, respectively.

The functionally-equivalent polypeptides of the first aspect of the invention may also be polypeptides which have been identified using one or more techniques of structural alignment. For example, the Inpharmatica Genome Threader™ technology that forms one aspect of the search tools used to generate the Biopendium search database may be used (see co-pending International Patent Application No. PCT/GB01/01105, published as WO 01/69507) to identify polypeptides of presently-unknown function which, while having low sequence identity as compared to the INSP052 and INSP055 polypeptides, are predicted to be immunoglobulin domain-containing cell surface recognition molecules, said method utilising a polypeptide of the first aspect of the invention, by virtue of sharing significant structural homology with the INSP052 and INSP055 polypeptide sequences. By "significant structural homology" is meant that the Inpharmatica Genome Threader™ predicts two proteins to share structural homology with a certainty of at least 10% and more preferably, at least 20%, 30%, 40%, 50%, 60%, 70%, 80%, 90% and above.

The polypeptides of the first aspect of the invention also include fragments of the INSP052 and INSP055 polypeptides and fragments of the functional equivalents of the INSP052 and INSP055 polypeptides, provided that those fragments retain immunoglobulin domain-containing cell surface recognition molecule activity or have an antigenic determinant in common with the INSP052 and INSP055 polypeptides.

As used herein, the term "fragment" refers to a polypeptide having an amino acid sequence that is the same as part, but not all, of the amino acid sequence of the INSP052 and INSP055 polypeptides or one of its functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known immunoglobluin domain-containing cell surface recognition molecules.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for known immunoglobluin domain-containing cell surface recognition molecules.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988);. Kabat et al., J. Immunol., 147, 1709 (1991); Queen et al., Proc. Natl Acad. Sci. USA, 86, 10029 (1989); Gorman etal., Proc. Natl Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode the polypeptide sequences recited in SEQ ID NO:2, SEQ ID NO:4, SEQ ID NO:6, SEQ ID NO:8, SEQ ID NO:10, SEQ ID NO:12, SEQ ID NO:14 and/or SEQ ID NO:16, SEQ ID NO:18, the extracellular domain of INSP052 (SEQ ID NO:20 and SEQ ID NO:22), SEQ ID NO:24, or SEQ ID NO:26 and functionally equivalent polypeptides, e.g. variants of the INSP052 extracellular domain such as the Ig-domain containing fragment of INSP052 (SEQ ID NO:31), or fusion proteins consisting of the extracellular domain of INSP052 or variants thereof fused to one or more additional polypeptide sequences. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

These molecules also may have a different sequence which, as a result of the degeneracy of the genetic code, encode a polypeptide of SEQ ID NO:2, SEQ ID NO:4, SEQ ID NO:6, SEQ ID NO:8, SEQ ID NO:10, SEQ ID NO:12, SEQ ID NO:14 and/or SEQ ID NO:16, or SEQ ID NO:18, or the extracellular domain of INSP052 or variants thereof, SEQ ID NO:24 or SEQ ID NO:26 or SEQ ID NO:31. Such molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979);. Cooney et al., Science 241, 456 (1988); Dervan et al., Science 251, 1360 (1991).

The term "hybridization" as used herein refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP052 or INSP055 polypeptides (SEQ ID NO:1, SEQ ID NO:3, SEQ ID NO:5, SEQ ID NO:7, SEQ ID NO:9, SEQ ID NO:11, SEQID NO:13 and/or SEQ ID NO:15, or SEQ ID NO:17, or the nucleic acid sequence set forth in FIG. 7 or the coding portion of the nucleic acid sequence set forth in FIG. 7 (i.e. SEQ ID NO: 19 or SEQ ID NO: 21), SEQ ID NO: 23, or SEQ ID NO: 25) and nucleic acid molecules that are substantially complementary to such nucleic acid molecules. Preferably, a nucleic acid molecule according to this aspect of the invention comprises a region that is at least 80% identical over its entire length to the coding sequence for SEQ ID NO:2 given in SEQ ID NO:1, the coding sequence for SEQ ID NO:4 given in SEQ ID NO:3, the coding sequences for SEQ ID NO:6 given in SEQ ID NO:5, the coding sequence for SEQ ID NO:8 given in SEQ ID NO:7, the coding sequence for SEQ ID NO:10, given in SEQ ID NO:9, the coding sequence for SEQ ID NO:12 given in SEQ ID NO:11, the coding sequence for SEQ ID NO:14 given in SEQ ID NO:13, the coding sequence for SEQ ID NO:16 given in SEQ ID NO:15, the coding sequence for SEQ ID NO:18 given in SEQ ID NO:17, the coding sequence for SEQ ID NO:24 given in SEQ ID NO:23, the coding sequence for SEQ ID NO: 26 given in SEQ ID NO: 25, or is a nucleic acid molecule that is complementary thereto. Particularly preferred is a nucleic acid which comprises or consists of a region that is at least 80% identical over its entire length to the coding sequence for the extracellular domain of INSP052 (the extracellular domain of mature INSP052 or the extracellular domain of INSP052 comprising the signal peptide) as given in FIG. 7. In this regard, nucleic acid molecules at least 90%, preferably at least 95%, more preferably at least 98% or 99% identical over their entire length to the same are particularly preferred. Preferred embodiments in this respect are nucleic acid molecules that encode polypeptides which retain substantially the same biological function or activity as the INSP052 and INSP055 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP052 and INSP055 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP052 and INSP055 polypeptides is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25) are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., [supra]. Particularly suitable methods include calcium phosphate transfection, DEAE-dextran mediated transfection, transvection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSportI™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line which contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from,. inter alia, Invitrogen, San Diego Calif. (the "MaxBac" kit). These techniques are generally known to those skilled in the art and are described fully in Summers and Smith, Texas Agricultural Experiment Station Bulletin No 1555 (1987). Particularly suitable host cells for use in this system include insect cells such as Drosophila S2 and Spodoptera Sf9 cells.

There are many plant cell culture and whole plant genetic expression systems known in the art. Examples of suitable plant cellular genetic expression systems include those described in U.S. Pat. Nos. 5,693,506; 5,659,122; and 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include streptococci, staphylococci, *E. coli*, Streptomyces and Bacillus subtilis cells.

Examples of particularly suitable host cells for fungal expression include yeast cells (for example, *S. cerevisiae*) and Aspergillus cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk- or aprt±cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide.

Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to. use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2): Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:
(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and
(b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:
(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and
(b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide. The skilled person will understand that the term "ligand" encompasses any moiety that binds specifically to the polypeptide of the first aspect of the invention including, for example, antibodies and orphan receptors.

In another embodiment of the method for identifying agonist or antagonist of a polypeptide of the present invention comprises:
determining the inhibition of binding of a ligand to cells which have a polypeptide of the invention on the surface thereof, or to cell membranes containing such a polypeptide, in the presence of a candidate compound under conditions to permit binding to the polypeptide, and determiniing the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:
(a) incubating a labelled ligand with a whole cell expressing a polypeptide according to the invention on the cell surface, or a cell membrane containing a polypeptide of the invention,
(b) measuring the amount of labelled ligand bound to the whole cell or the cell membrane;
(c) adding a candidate compound to a mixture of labelled ligand and the whole cell or the cell membrane of step (a) and allowing the mixture to attain equilibrium;
(d) measuring the amount of labelled ligand bound to the whole cell or the cell membrane after step (c); and (e) comparing the difference in the labelled ligand bound in step (b) and (d), such that the compound which causes the reduction in binding in step (d) is considered to be an agonist or antagonist.

The polypeptides may be found to modulate a variety of physiological and pathological processes in a dose-dependent manner in the above-described assays. Thus, the "functional equivalents" of the polypeptides of the invention include polypeptides that exhibit any of the same modulatory activities in the above-described assays in a dose-dependent manner. Although the degree of dose-dependent activity need not be identical to that of the polypeptides of the invention, preferably the "functional equivalents" will exhibit substantially similar dose-dependence in a given activity assay compared to the polypeptides of the invention.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Persons skilled in the art will be able to devise assays for identifying modulators of a polypeptide of the invention. Of interest in this regard is Lokker N A et al J Biol Chem 1997 Dec. 26; 272(52):33037-44 which reports an example of an assay to identify antagonists (in this case neutralizing antibodies).

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art and this can be used to search for compounds that may inhibit or enhance the production of the polypeptide from suitably manipulated cells or tissues. The formation of binding complexes between the polypeptide and the compound being tested may then be measured.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signalling and metabolic pathways in which the particular genes/polypeptides are implicated, generate information regarding the identities of polypeptides with which the studied polypeptides interact and provide clues as to methods by which related genes and proteins are regulated.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise: effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (ie. to prevent infection) or therapeutic (ie. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial. toxoid, such as a toxoid from diphtheria, tetanus, cholera, H. pylori, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, See Worldwide Website: powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;

b) isolating a nucleic acid molecule according to the invention from said tissue sample; and c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Nati. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the inyention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease, including, but not limited to, diseases including, but not limited to, cell proliferative disorders, autoimmune/inflammatory disorders, cardiovascular disorders, neurological and psychiatric disorders, developmental disorders, genetic disorders, metabolic disorders, infections and other pathological conditions. These diseases preferably include neoplasm, cancer, brain tumour, glioma, bone tumor, lung tumor, breast tumour, prostate tumour, colon tumour, hemangioma, myeloproliferative disorder, leukemia, hematological disease, neutropenia, thrombocytopenia, angiogenesis disorders, dermatological disease, ageing, wounds, burns, fibrosis, cardiovascular disease, restensosis, heart disease, peripheral vascular disease, coronary artery disease, oedema, thromboembolism, dysmenorrhea, endometriosis, pre-eclampsia, lung disease, COPD, asthma bone disease, renal disease, glomerulonephritis, skin disease, liver disease, Crohn's disease, gastritis, ulcerative colitis, ulcer, immune disorder, autoimmune disease, arthritis, rheumatoid arthritis, psoriasis, epidermolysis bullosa, systemic lupus erythematosus, ankylosing spondylitis, Lyme disease, multiple sclerosis, neurodegeneration, stroke, brain/spinal cord injury, Alzheimer's disease, Parkinson's disease, motor neurone disease, neuromuscular disease, HIV, AIDS, cytomegalovirus infection, fungal infection, ocular disorder, macular degeneration, glaucoma, diabetic retinopathy, ocular hypertension and other conditions in which immunoglobulin domain containing cell recognition molecules are implicated.

Various aspects and embodiments of the present invention will now be described in more detail by way of example, with particular reference to the INSP052 and INSP055 polypeptides.

It will be appreciated that modification of detail may be made without departing from the scope of the invention.

BRIEF DESCRIPTION OF THE FIGURES

FIGS. 1A-1B: (A) Multiple alignment generated by CLUSTALW of the full-length INSP052 (SEQ ID NO:16) polypeptide sequence, the mature, isolated extracellular domain INSP052 (INSP052EC, SEQ ID NO:22), and the closest related sequence identified in WO04/009834 (SEQIDNO434, SEQ ID NO:28) and SEQIDNO880, SEQ ID NO:32). (B) Multiple alignment generated by CLUSTALW comparing INSP052EC (SEQ ID NO:22) with the corresponding histidine tagged (INSP052EC-6His, SEQ ID NO:29) and Fc fusion (INSP052EC-FC, SEQ ID NO:30) versions of this sequence and with the Ig-domain-containing fragment of INSP052 (SEQ ID NO:16) (INSP052Ig2, SEQ ID NO:31). The Fc sequence corresponds to amino acids 246-477 of the constant region of human immunoglobulin lambda heavy chain. IgG1; NCBI Acc. No. CAA75302. Underlined sequence denotes predicted signal peptide. Boxed sequence denotes predicted transmembrane domain. "*" indicates identical residues amongst the aligned sequences: ":" indicates homologous residues amongst the aligned sequences.

FIG. 2: % of secreted TNF-alpha (TNF-a) by ConA-stimulated hPBMC mixed with serially diluted preparations of INSP052EC-6His (expressed in dilution of the protein preparation; see Example 4). The two curves (interpolating either crosses or circles) represent the results obtained with two different lots of the protein.

FIG. 3: % secreted IL-4 (Interleukin 4) by ConA-stimulated hPBMC mixed with serially diluted preparations of INSP052EC-6His (expressed in dilution of the protein preparation; see Example 4). The two curves (interpolating either crosses or circles) represent the results obtained with two different lots of the protein.

FIG. 4: % secreted IL-2 (Interleukin 2) by ConA-stimulated HPBMC mixed with serially diluted preparations of INSP052EC-6His (expressed in dilution of the protein preparation; see Example 4). The two curves (interpolating either crosses or circles) represent the results obtained with two different lots of the protein.

EXAMPLES

Example 1

INSP052 and INSP055 Sequences

Figure 5A:
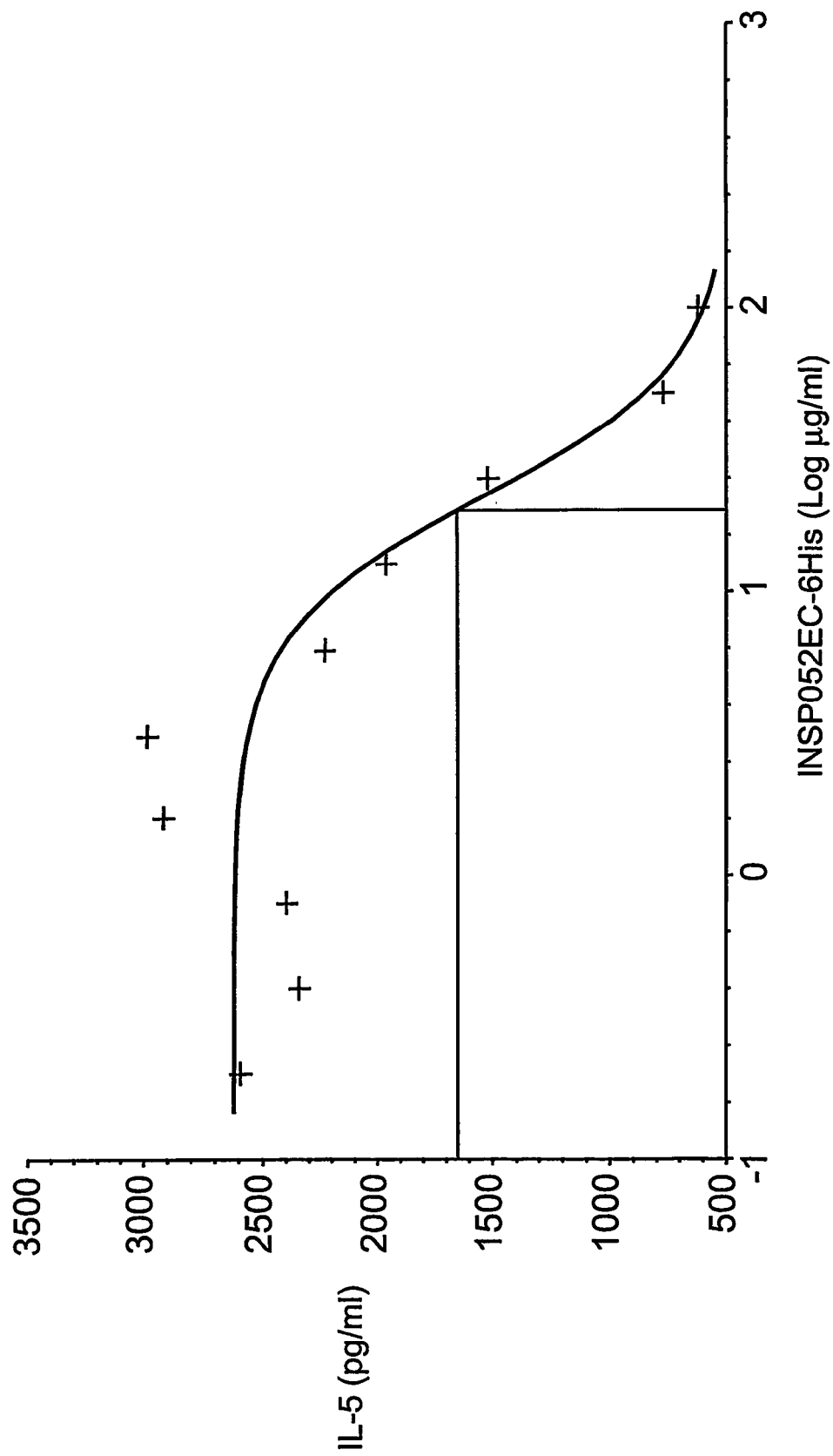
FIGS. 5A-5B: inhibition of IL-5 (Interleukin 5; A) and IL-2 (Interleukin 2; B) secretion ConA-stimulated hPBMC mixed with increasing amount of INSP052EC-6His (expressed in log of the concentration of the protein in The IC50 value is indicated by the line interpolating the curve and the X/Y axis.

The polypeptide sequence derived from combining SEQ ID NO:2, SEQ ID NO:4, SEQ ID NO:6, SEQ ID NO:8, SEQ ID NO:10, SEQ ID NO:12 and SEQ ID NO:14 and SEQ ID NO:16 which represents the translation of consecutive exons from INSP052 is derived from human genomic DNA sequence. The polynucleotide and polypeptide sequences SEQ ID NO: 17 and SEQ ID NO:18 representing INSP055 are polynucleotide and polypeptide sequences of the mouse orthologue of INSP052 respectively. INSP052 and INSP055 polypeptide sequences represented by SEQ ID NO16 and SEQ ID NO18, respectively, are predicted to contain signal peptide sequences and a transmembrane spanning domain. In particular, the full and mature sequence of the extracellular domain has been identified at the DNA and protein level (SEQ ID NO:19-22).

As indicated in WO 03/93316, the INSP052 full length prediction encodes a type I membrane protein of 416 amino acids, related to the VEGF/PDGF receptors, belonging to the immunoglobulin superfamily. The putative signal sequence consists of amino acids 1-33 of INSP052. The predicted transmembrane (TM) domain consists of amino acids 241-263 of INSP052. Thus the mature extracellular domain of INSP052 consists of amino acids 34-240 of INSP052. This latter sequence is similar to two sequences disclosed in the literature as SEQIDNO434 and SEQIDNO880 (WO 04/009834; SEQ ID NO:27 and 28).

Variants of INSP052EC (the extracellular domain of mature INSP052; SEQ ID NO:22) or of the corresponding full extracellular domain (SEQ ID NO:20) can be generated by fusing heterologous protein sequences at the N- and/or C-terminus of this protein sequence, with the purpose of facilitating protein production, purification, or stability when produced using recombinant DNA technologies. Design of the moieties, ligands, and linkers, as well methods and strategies for the construction, purification, detection, maturation, and use of fusion proteins are widely discussed in the literature (Nilsson J et al., Protein Expr Purif, 11: 1-16, 1997; "Applications of chimeric genes and hybrid proteins" Methods Enzymol. Vol. 326-328, Academic Press, 2000).

Other examples of such fusion proteins are the ones including signal sequence from another protein (such as the one human growth hormone or beta2-Microglobulin), a purification tag (such as a Histidine tag or a HA tag), the extracellular domain of a different membrane-bound protein, a secreted protein (such as a cytokine or a serum protein like albumin), a starting Methionine (in order allow the direct expression, for example, in $E.$ $coli$), a linker region containing a recognition site for an endopeptidase (facilitating the elimination of the heterologous protein sequence), or the Fc region from a human immunoglobulin (FIG. 1B).

The choice of one or more of these sequences to be fused to INSP052EC is functional to specific use and/or purification protocol of said protein as recombinant protein. For example, the activity of INSP052EC can be also test tested by means of a fusion protein including an albumin sequence or, as shown in the examples with INSP052EC-6HIS (SEQ ID NO:29), a histidine tag sequence facilitating both detection and purification.

Alternatively, fusion proteins comprising INSP052EC can be obtained by linking this sequence to an immunoglobulin domain constant region, a protein domain known to improve the stability and the efficacy of recombinant proteins in the circulation. The resulting fusion protein can be expressed directly by mammalian cells (such as CHO or HEK293 cells) using the appropriate expression vectors so that the fusion protein is secreted in the culture medium.

Different strategies for generating fusion protein comprising an immunoglobulin fragment are disclosed in the literature (WO 91/08298; WO 96/08570; WO 93/22332; WO 04/085478; WO 02/66514). For example, the nucleic acid sequence encoding the mature INSP052EC can be cloned in an expression vector fused to a nucleic acid sequence encoding the original INSP052EC signal sequence (or any other appropriate signal sequence) at its 5' end, and the nucleic acid sequence encoding the constant region of human immunoglobulin lambda heavy chain IgG1 (NCBI Acc. No. CAA75302) at its 3' end (SEQ ID NO: 30). The resulting vector can be used to transform a CHO or HEK293 cell line and the clones stably expressing and secreting the recombinant fusion protein having INSP052EC at the N-terminus and the IgG1 sequence at the C-terminus can be selected. This clone then can be used for scaling up the production and for purifying the recombinant fusion protein from the culture medium. Alternatively, the position of the nucleic acid encoding the constant region of human immunoglobulin lambda heavy chain IgGI and INSP052EC can be inversed, and the resulting protein can be expressed and secreted using still the original signal sequence of INSP052, or any other appropriate signal sequence.

Other protein sequences allowing the multimerization of INSP052EC are domains isolated from proteins such hCG (WO 97/30161), collagen X (WO 04/33486), C4BP (WO 04/20639), Erb proteins (WO 98/02540), or coiled coil peptides (WO 01/00814).

The additional sequence include in these fusion proteins may be eliminated at the end of its purification or in vivo, if needed, by means of an appropriate endo-/exopeptidase. For example, the linker sequence included in the recombinant protein may present a recognition site for an endopeptidase (such as a caspase) that can be used to detach enzymatically the desired protein from the heterologous sequence either in vivo or in vitro. Alternatively, if the protein sequence to be expressed does not contain a staring methionine (for example, if the sequence encodes for only the mature sequence of the protein, without the signal peptide), a protein of the Invention can be expressed correctly in a host cell with a starting Methionine. This additional amino acid may be then either maintained in the resulting recombinant protein, or eliminated by means of an exopeptidase, such as Methionine Aminopeptidase, according to methods disclosed in the literature (Van Valkenburgh H A and Kahn R A, Methods Enzymol., 344:186-193, 2002; Ben-Bassat A, Bioprocess Technol., 12:147-59, 1991).

Example 2

Cloning of the INSP052 Extracellular Domain

The DNA encoding the entire extracellular region of INSP052 (amino acids 1-240) was cloned by exon assembly from human genomic DNA as described in WO 03/093316. The protein was then expressed and purified as a Histidine tagged fusion protein (INSP052EC-6His; SEQ ID NO:29).

Example 3

Expression In Mammalian Cells of the His-tagged Version of INSP052 Extracellular Domain (INSP052EC-6His-V1 plasmid)

The construction of the expression vector for the His-tagged version of INSP052 extracellular domain (INSP052EC-6His-V1), the transfection of the construct for transfecting Human Embryonic Kidney 293 cells expressing the Epstein-Barr virus Nuclear Antigen (HEK293-EBNA, Invitrogen), and the purification of the recombinant protein INSP052EC-6His was performed as described in WO 03/93316. This protein was then used for a series of functional tests.

Example 4

Cytokine Expression Modulation Assays Using Human PBMCs 4.1: Introduction

The following in vitro cell-based assays measure the effects of INSP052EC (cloned extracellular domain of INSP052) that was expressed in a Histidine-tagged version to facilitate its purification (INSP052EC-6His; see Examples 2 and 3), on cytokine secretion induced by different stimuli on human peripheral blood mononuclear cells (hPBMC) cells. Cytokine bead array (CBA) assays were established for IL-2, IFN-γ, TNF-α, IL-5, IL-4 and IL-10. In particular, proteins were used initially at 3 different concentrations, and 3 different time points were considered for each concentration—(24, 48, and 72 hours after stimulation).

The best conditions are 100 000 cells/well in 96-well plates and 100 μl final in 2% glycerol (MERCK). The optimal concentration was 5 ng/ml for ConA. The optimal time for the assay is 48 hours. The optimal concentration of the inhibitor of cytokine secretion/expression (positive control), dexamethasone, is $10^{-6}$ M. The optimal concentration of the stimulator of cytokine secretion/expression (negative control), human Interleukin 18 (hIL-18), is 100 ng/ml.

4.2: Purification of Human PBMC From A Buffy Coat

The buffy coat was diluted 1 to 2 with DMEM (GIBCO). 25 ml of diluted blood was thereafter slowly added onto a 15 ml layer of Ficoll (PHARMACIA) in a 50 ml Falcon tube, and tubes were centrifuged (2000 rpm, 20 min, at RT without brake). The interphase (ring) was then collected and the cells were washed with 25 ml of DMEM followed by a centrifuge step (1200 rpm, 5 min). This procedure was repeated three times. A buffy coat gave approximately $600 \times 10^6$ total cells.

4.3: Screening

80 μl of $1.25 \times 10^6$ cells/ml were diluted in DMEM (GIBCO) +2.5% Human Serum (type AB SIGMA) +1% L-Glutamine (GIBCO) +1% Penicillin-Streptomycin (GIBCO) and thereafter added to a 96 well microtiter plate (NUNC, COSTAR).

10 μl were added per well (one condition per well): Proteins were diluted in PBS+20% Glycerol (the final dilution of the proteins is 1/10). The assay was conducted in replica and using serial dilution of the protein. 10 μl of the ConA 50 μg/ml (the final concentration of ConA is 5 μg/ml) were then added per well (one condition per well).

For further clarification the Table below shows the experimental design.

| | 1 | 2 | 3 | 4 | 5 | 6 | 7 | 8 | 9 | 10 | 11 | 12 |
|---|---|---|---|---|---|---|---|---|---|---|---|---|
| A | Medium | Prot + STIM | Prot + STIM | Prot + STIM | Prot + STIM | Prot + STIM | Prot + STIM | Prot + STIM | Prot + STIM | Prot + STIM | Prot + STIM | Medium |
| B | Medium | Prot + STIM | Prot + STIM | Prot + STIM | Prot + STIM | Prot + STIM | Prot + STIM | Prot + STIM | Prot + STIM | Prot + STIM | Prot + STIM | Medium |
| C | STIM | Prot + STIM | Prot + STIM | Prot + STIM | Prot + STIM | Prot + STIM | Prot + STIM | Prot + STIM | Prot + STIM | Prot + STIM | Prot + STIM | STIM |
| D | STIM | Prot + STIM | Prot + STIM | Prot + STIM | Prot + STIM | Prot + STIM | Prot + STIM | Prot + STIM | Prot + STIM | Prot + STIM | Prot + STIM | STIM |
| E | STIM | Prot + STIM | Prot + STIM | Prot + STIM | Prot + STIM | Prot + STIM | Prot + STIM | Prot + STIM | Prot + STIM | Prot + STIM | Prot + STIM | STIM |
| F | STIM + dexa 10-6M | Prot + STIM | Prot + STIM | Prot + STIM | Prot + STIM | Prot + STIM | Prot + STIM | Prot + STIM | Prot + STIM | Prot + STIM | Prot + STIM | STIM + IL-18 100 ng/ml |
| G | STIM + dexa 10-6M | Prot + STIM | Prot + STIM | Prot + STIM | Prot + STIM | Prot + STIM | Prot + STIM | Prot + STIM | Prot + STIM | Prot + STIM | Prot + STIM | STIM + IL-18 100 ng/ml |
| H | STIM + dexa 10-6M | Prot + STIM | Prot + STIM | Prot + STIM | Prot + STIM | Prot + STIM | Prot + STIM | Prot + STIM | Prot + STIM | Prot + STIM | Prot + STIM | STIM + IL-18 100 ng/ml |

STIM indicates ConA (5 μg/ml);
Prot indicates INSP052EC-6His;
Dexa is Dexamethasone;
IL-18 is human Interleukin 18.

4.4: CBA Analysis

After 48 hours, cell supernatants were collected and human cytokines were measured by Human Th1/Th2 Cytokine CBA Kit (Becton-Dickinson).

i) Preparation of mixed Human Th1/Th2 Capture Beads

The number of assay tubes that were required for the experiment was determined.

Each capture bead suspension was vigorously vortexed for a few seconds before mixing. For each assay to be analysed, 10 μl aliquot of each capture bead were added into a single tube labelled "mixed capture beads". The Bead mixture was thoroughly vortexed.

ii) Preparation of test samples

Supernatants were diluted (1:4) using the Assay Diluent (20 μl of supernatants+60 μl of Assay Diluent). The sample dilution was then mixed before transferring samples into a 96 wells microtiter plate conical bottom (Nunc).

iii) Human Th1/Th2 Cytokine CBA Assay Procedure

50 μl of the diluted supernatants were added into a 96 wells microtiter plate conical bottom (Nunc). 50 μl of the mixed capture beads were added followed by 50 μl addition of the Human Th1/Th2 PE Detection Reagent. The plate was then incubated for 3 hours at RT and protected from direct exposure to light followed by centrifugation at 1500 rpm for 5 minutes. The supernatant was then carefully discarded. In a subsequent step, 200 μl of wash buffer were twice added to each well, centrifuged at 1500 rpm for 5 minutes and supernatant carefully discarded. 130 μl of wash buffer were thereafter added to each well to resuspend the bead pellet. The samples were finally analysed on a flow cytometer (Becton-Dickinson). The data were analysed using the CBA Application Software, Activity Base and Microsoft Excel software.

4.5: Results

As shown in FIGS. 2, 3. and 4, INSP052EC-6His was able to down-regulate in a dose-dependent manner the secretion of cytokines (for example TNF-alpha, IL-4 and IL-2) from ConA-stimulated hPBMC using two different lots of the protein. These results confirm a potential therapeutic efficacy of INSP052EC in the treatment of anti-inflammatory and auto-immune diseases.

Figure 5B:
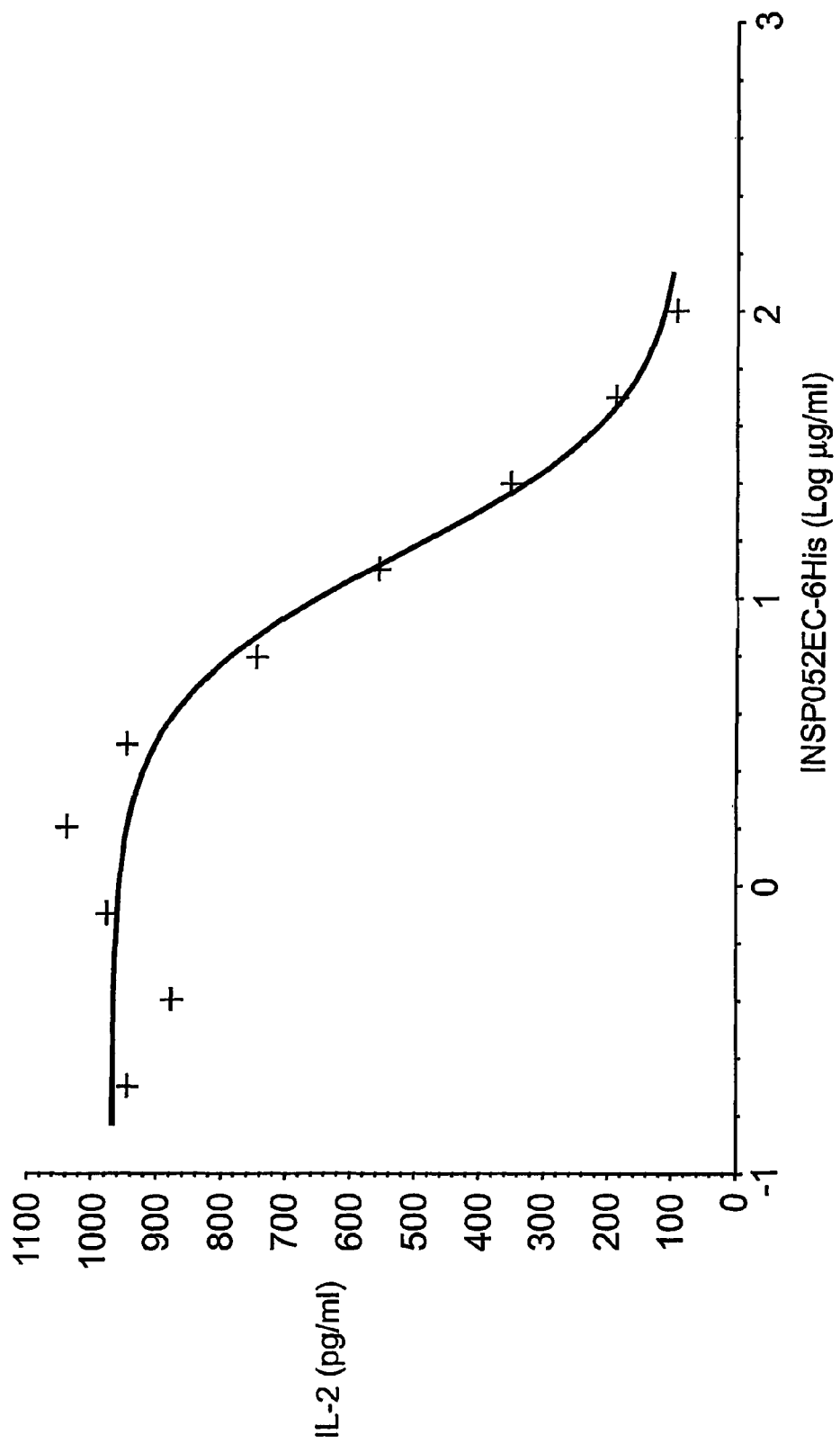

A more detailed analysis was performed by calculating the dose-response effect on cytokine secretion in terms of IC50, that is the concentration of INSP052EC-6His needed to reduce the secretion of the cytokine (calculated in pg/ml) down to 50% of the maximal value observed. The resulting curves of inhibition (as exemplified for IL-5 and IL-2 in FIG. 5), demonstrate that INSP052EC-6His is active as a cytokine antagonist, and in particular as inhibitor of cytokine secretion and/or expression, in a concentration range of μg/ml: TNF-alpha (IC50: 6-10 μg/ml), IFN-γ (IC50: 3-9 μg/ml), IL-2 (IC50:12-14 μg/ml), IL-4 (IC50: 14 μg/ml), IL-10 (IC50: 10-15 μg/ml) and IL-5 (IC50: 18 μg/ml).

Example 5

Cytokine Expression Modulation Assays Using Human T Cells 5.1: Materials & Methods:

Sub-populations of leukocytes were prepared using MACS cell isolation kit (Miltenyi Biotec) according to the manufacturer's instructions. hPBMC were isolated from buffy coats as described in Example 4. Care was taken to ensure a single-cell suspension. For preparation of CD4+ T cells the CD4+ T Cell Isolation Kit II was used (catalogue number 130-091-155). PBMC were counted, centrifuged for 10 minutes and re-suspended in cold PBS buffer (phosphate buffered saline pH 7.2, supplemented with 0.5% bovine serum albumin, BSA, and 2 mM EDTA) at a concentration of $2.5 \times 10^8$ cells per ml (40 μl of buffer per $10^7$ cells). 10 μl of Biotin-Antibody Cocktail (supplied with the kit) per $10^7$ total cells was added. The suspension was mixed well and incubated at 4-8° C. for 10 minutes. 30 μl of buffer was added per $10^7$ cells followed by 20 μl of Anti-Biotin MicroBeads per $10^7$ total cells. The suspension was mixed well and incubated for an additional 15 minutes at 4-8° C. The cells were washed with buffer by adding 10-20 fold the labeling volume and centrifuged at 300×g for 10 minutes. The supernatant was removed completely and the cells re-suspended up to $10^8$ cells in 500 ul of buffer. Magnetic separation was carried out with an autoMACS™ Separator. The autoMACS™ Separator was prepared and primed according to the manufacturer's instructions. The tube containing the magnetically labeled cells was placed in the autoMACS™ Separator and the program "deplete" was chosen. The negative fraction was collected (outlet port "neg1"). This fraction represents the enriched CD4+ T cells. Where required, the positive fraction was subsequently collected (outlet port "pos1"). This fraction represents the magnetically labeled non-CD4+ T cells.

The screening and the CBA assays were performed as described above for hPBMC.

5.2: Results

Figure 6A:
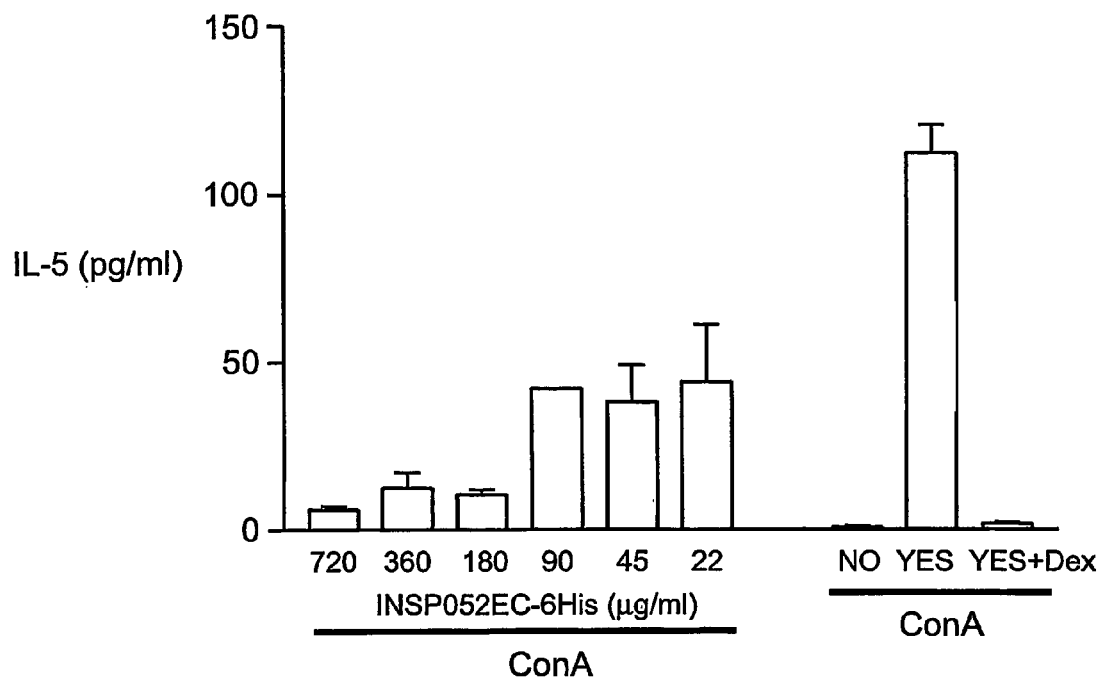
FIGS. 6A-6B: inhibition of IL-5 (Interleukin 5; A) and IL-2 (Interleukin 2; B) secretion by ConA-stimulated purified CD4+ T cells mixed with increasing amount of INSP052EC-6His (expressed in µg/ml). The effect can be compared to the values of cytokine secretion in presence or absence of ConA (YES, NO), and in presence of both ConA and Dexamethasone (Dex; 0.1 mg/kg).
Figure 6B:
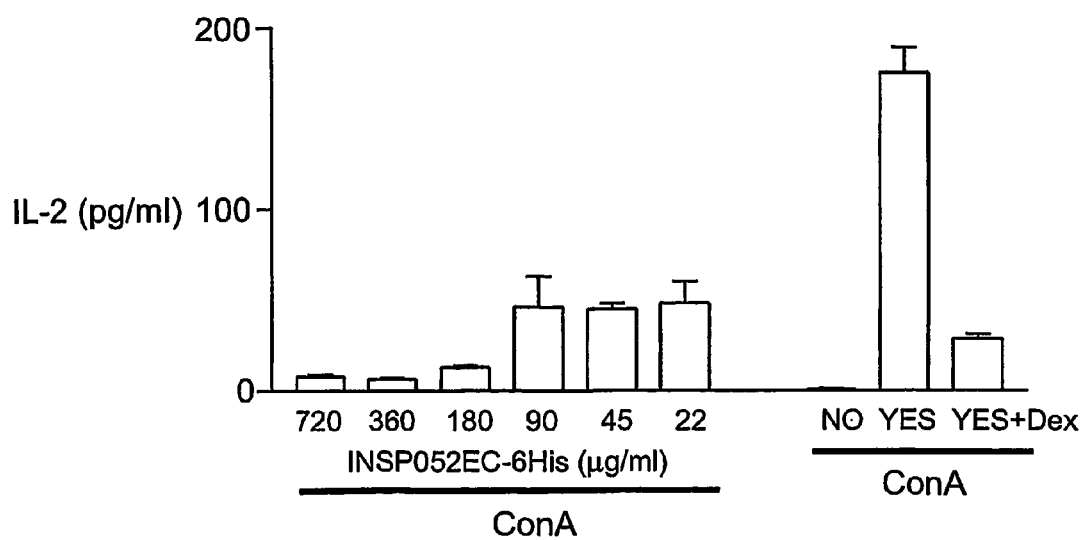

The decrease in cytokine secretion from hPBMC induced by INSP052EC-6His was also observed in purified CD4+ T cells following stimulation with ConA. The effects on the secretion of cytokines were consistent with the ones measured in hPBMC, proportional to the amount of protein added in the sample, and comparable with the reduction observed with a common anti inflammatory compound (FIG. 6).

Example 6

Mouse Model of Fulminant Liver Hepatitis 6.1: Introduction

Since INSP052EC protein (expressed in the recombinant form INSP052EC-6His) has been shown in vitro to inhibit secretion of various cytokines by ConA-stimulated human peripheral blood mononuclear cells (hPBMC; see Example 4), as well as in CD4+ T cells (Example 5), it has been decided to test the activity of INSP052EC in the in vivo ConA model by electrotransfer.

6.2: Background—Concanavalin A (ConA)-induced Liver Hepatitis

Toxic liver disease represents a worldwide health problem in humans for which pharmacological treatments have yet to be discovered. For instance active chronic hepatitis leading to liver cirrhosis is a disease state, in which liver parenchymal cells are progressively destroyed by activated T cells. ConA-induced liver toxicity is one of three experimental models of T-cell dependent apoptotic and necrotic liver injury described in mice. Gal N (D-Galactosamine) sensitized mice challenged with either activating anti-CD3 monoclonal AB or with superantigen SEB develop severe apoptotic and secondary necrotic liver injury (Kusters S, Gastroenterology. 1996 August; 111(2):462-71). Injection of the T-cell mitogenic plant lectin ConA to non sensitized mice results also in hepatic apoptosis that preceeds necrosis. ConA induces the release of systemic TNF-alpha and IFN-gamma and various other cytokines. Both TNF-alpha and IFN-gamma are critical mediators of liver injury. Transaminase release 8 hours after the insult indicates severe liver destruction.

Several cell types have been shown to be involved in liver damage, CD4 T cells, macrophages and natural killer cells (Kaneko J Exp Med 2000, 191, 105-114). Anti-CD4 antibodies block activation of T cells and consequently liver damage (Tiegs et al. 1992, J Clin Invest 90, 196-203). Pre-treatment of mice with monoclonal antibodies against CD8 failed to protect, whereas deletion of macrophages prevented the induction of hepatitis.

The present study was undertaken to investigate the role of INSP052EC, a TNF-alpha/IL-4 cytokines antagonist protein containing IgG-like domains, in ConA-induced liver hepatitis. Several cytokines have been shown either to be critical in inducing or in conferring protection from ConA-induced liver damage. TNF-alpha for example is one of the first cytokines produced after ConA injection and anti-TNF-alpha antibodies confer protection against disease (Seino et al. 2001, Annals of surgery 234, 681-688). IFN-gamma appears also to be a critical mediator of liver injury, since anti-IFN-gamma antiserum significantly protect mice, as measured by decreased levels of transaminases in the blood of ConA-treated animals (see Kusters et al., above). In liver injury, increased production of IFN-gamma was observed in patients with autoimmune or viral hepatitis. In addition transgenic mice expressing IFN-gamma in the liver develop liver injury resembling chronic active hepatitis (Toyonaga et al. 1994, PNAS 91, 614-618). IFN-gamma may also be cytotoxic to hepatocytes, since in vitro IFN-garnma induces cell death in mouse hepatocytes that was accelerated by TNF alpha (Morita et al. 1995, Hepatology 21, 1585-1593).

Other molecules have been described to be protective in the ConA model. A single administration of rhIL-6 (recombinant human Interleukin 6) completely inhibited the release of transaminases (Mizuhara et al. 1994, J. Exp. Med. 179, 1529-1537).

6.3: cDNA Electrotransfer Into Muscle Fibers In Order To Achieve Systemic Expression of A Protein of Interest (INSP052EC)

Among the non-viral techniques for gene transfer in vivo, the direct injection of plasmid DNA into the muscle and subsequent electroporation is simple, inexpensive and safe. The post-mitotic nature and longevity of myofibers permits stable expression of transfected genes, although the transfected DNA does not usually undergo chromosomal integration (Somiari et al. 2000, Molecular Therapy 2, 178-187). Several reports have demonstrated that secretion of muscle-produced proteins into the blood stream can be achieved after electroporation of corresponding cDNAs (Aihara H and Miyazaki J, 1998, Nature Biotech 16, 867-870). In addition in vivo efficacy of muscle expressed EPO and IL-18BP in disease models has been shown (Rizzuto et al., 2000, Human Gene Therapy 41, 1891-1900; Mallat Z et al., 2001, Circulation Research 89, E41-45).

6.4: Materials and Methods 6.4.1: Animals

In all the studies male C57/BL6 male (8 weeks of age) were used. In general, 7 animals per experimental group are used. Mice were maintained in standard conditions under a 12-hour light-dark cycle, provided irradiated food and water ad libitum.

6.4.2: Muscle Electrotransfer 6.4.2.1: Choice of Vector

StrepII-tagged human IL6 (hIL6-SII) and INSP052EC-6His genes were cloned in distinct Gateway compatible pDEST12.2 vectors, wherein the protein expression is under the control of the CMV promoter.

6.4.2.2: Electroporation Protocol

Mice were anesthetized with gas (isofluran Baxter, Ref: ZDG9623). Hindlimbs were shaved and an echographic gel was applied. Hyaluronidase was injected in the posterior tibialis mucle with (20U in 50 µl sterile NaCl 0.9%, Sigma Ref. H3631). After 10 minutes, 100 µg of plasmid (50 µg per leg in 25 µof sterile NaCl 0.9%) was injected in the same muscle. The DNA was prepared in the Buffer PBS-L-Glutamate (6 mg/ml; L-Glutamate Sigma P4761) before intramuscular injection. For electrotransfer, the electric field was applied for each leg with the ElectroSquarePorator BTX ref ECM830 at 75 Volts during 20 ms for each pulse, 10 pulses with an interval of 1 second in a unipolar way with 2 round electrodes (size 0.5 mm diameter).

6.4.3: The ConA Model 6.4.3.1: ConA i.v. Injection and Blood Sampling 8 weeks old Female Mice C57/B16 were purchased from IFFA CREDO. ConA (Sigma ref. C7275) was injected at 18 mg/kg i.v., and blood samples were taken at 1.30 and 8 hours post-injection. At the time of sacrifice, blood was taken from the heart.

6.4.3.2: Detection of Cytokines and Transaminases in Blood Samples

IL2, IL5, IL4, TNF-alpha and IFN-gamma cytokine levels were measured using the TH1/TH2 CBA assay. TNF-alpha, IL-6, MCP1, IFN-alpha, IL-10 and IL-12 were detected using the Inflammation CBA assay. Transaminase (ALAT and ASAT) blood parameters were determined using the COBAS instrument (Hitachi).

6.4.3.3: Electrotransfer of the Vectors Expressing Human INSP052EC-6His and hIL-6-SII At day 0 electrotransfer of pDEST12.2.-INSP052EC, pDEST12.2-hIL-6 as well as and the empty vector control (electrotransfer protocol see above) was performed. At day 5 after electrotransfer, ConA (18 mg/kg) was injected i.v. and blood sampled at 2 time points (1.30, 8 hours).

6.4.3.4: INSP052 and IL6 Protein Pretreatment in the ConA Model

CHO cell produced, recombinant hIL-6 or HEK293 cell produced, recombinant INSP052-6His was injected s.c. 30 minutes before ConA injection.

6.5: Results

We have shown previously (see Examples 4 and 5; FIGS. 2-6) that HEK 293 cell expressed INSP052EC-6His protein down-regulates TNF-alpha and IL-4 secretion (amongst other cytokines) in ConA stimulated hPBMC in vitro in a dose dependent way.

Since these two cytokines play a crucial role in T cell induced ConA induced liver hepatitis, we tested INSP052EC CDNA and protein in this model.

Figure 7A:
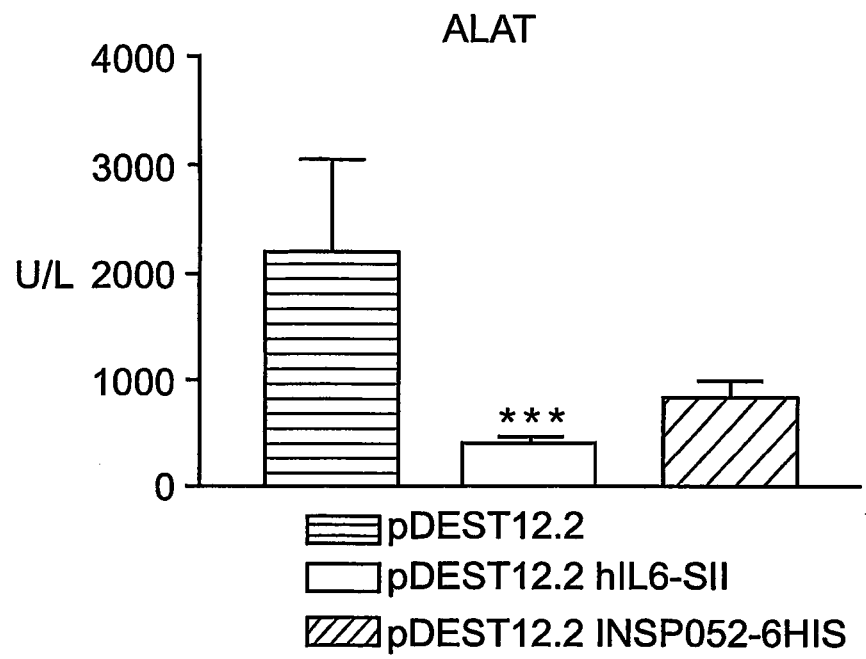
FIGS. 7A-7B: INSP052EC-electrotransferred animals (pDEST12.2 INSP052-6HIS) show a decrease of the blood levels of transaminases alanine aminotransferase (ALAT; A) and aspartate aminotransferase (ASAT; B) as compared to empty vector (pDEST12.2) control animals and human IL6-electrotransferred animals (pDEST12.2 hIL6-SII) 8 hours after the ConA challenge (see Example 6). The asterisks indicate the level of statistical significance of the decrease (the more asterisks, the more significant the decrease).
Figure 7B:
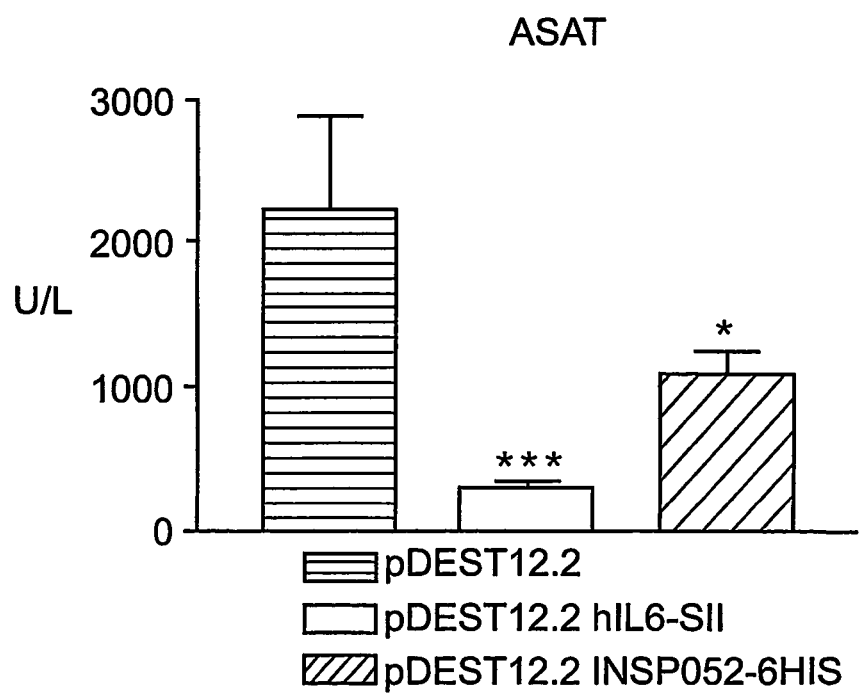
Figure 8A:
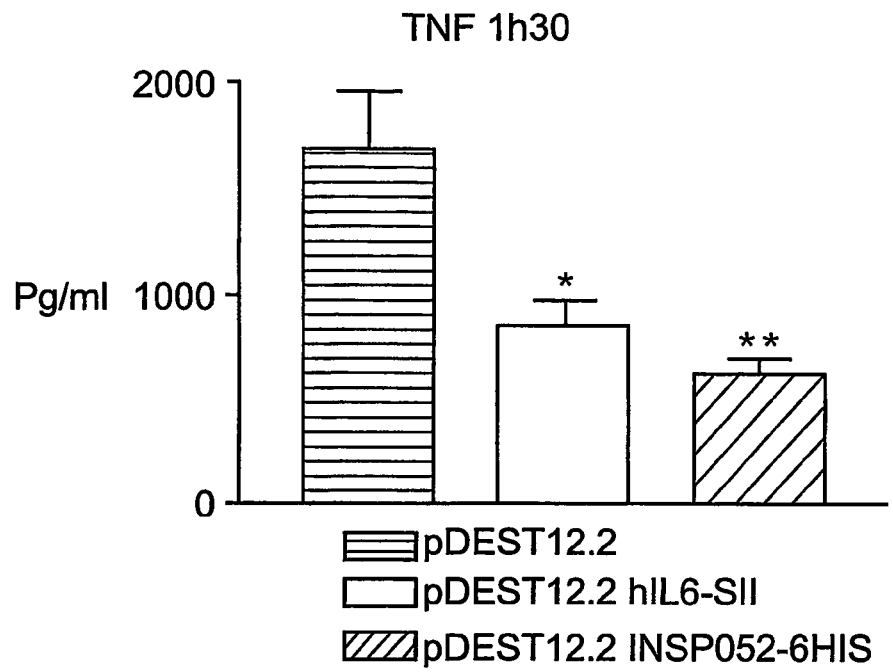
FIGS. 8A-8B: TNF-alpha and IL-6 cytokine levels in INSP052EC-6His- and hIL6-SII-electrotransferred animals (see Example 6 and FIG. 7).
Figure 8B:
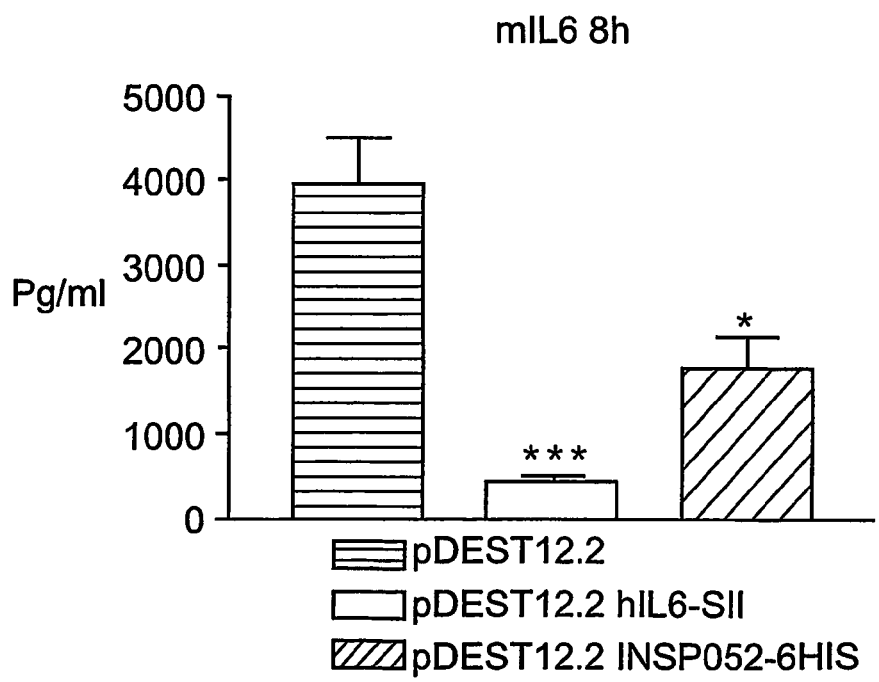

INSP052EC-6His protects from liver injury in a mouse model mimicking fulminant hepatitis after systemic delivery of the protein using electrotransfer. FIG. 7 show that INSP052EC-6His-eletrotransferred animals show a decrease in transaminase levels as compared to empty vector control animals 8 hours after the ConA challenge. In addition both TNF-alpha and IL-6 cytokine levels are significantly reduced in these animals (FIG. 8). Please note that the effect is similar, or even more important, to that obtained with the positive control vector pDEST12.2hIL-6-SII (FIGS. 7 and 8).

Figure 9A:
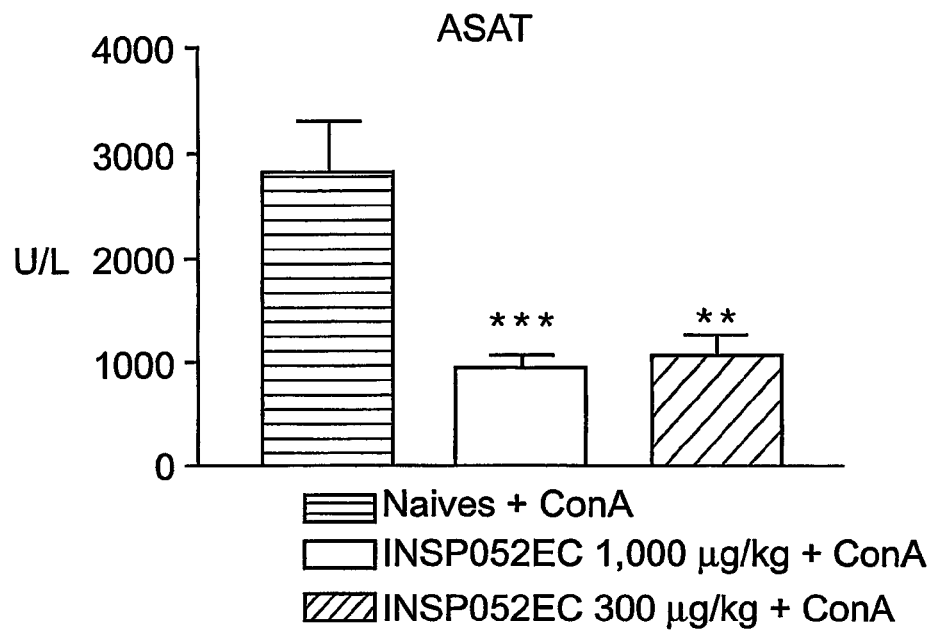
FIGS. 9A-9B: Effect of INSP052EC-6His administered in two dosages in mice then exposed to ConA. The blood levels of ASAT (A) and ALAT (B) were measured after 8 hours from ConA injection (see Example 6).
Figure 9B:
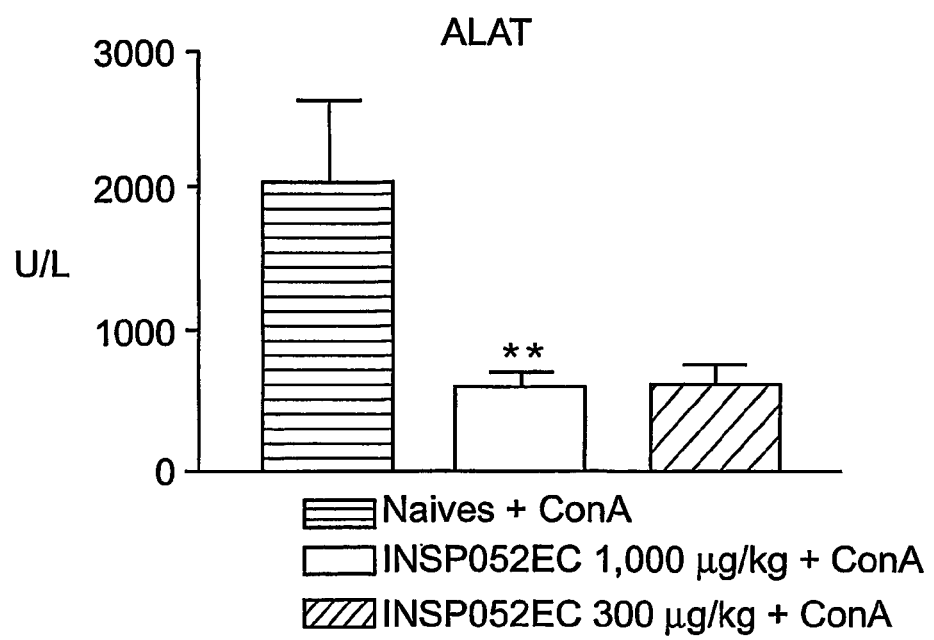

The protective effect of INSP052EC-6His was tested also by administering the purified recombinant protein before the injection of ConA. When s.c. injected, INSP052EC protein (1 mg/kg, or 0.3 mg/kg) decreased significantly ASAT and ALAT levels 8 hours after ConA injection (FIG. 9).

6.6: Conclusion

Our experiments have already show that INSP052EC downregulates the secretion and/or expression of cytokines such as TNF-alpha, IL-4 and IL-2 in vitro in the ConA stimulated hPBMC assay. In addition, the delivery of INSP052EC cDNA in an in vivo model of fulminant hepatitis decreases TNF-alpha and m-IL-6 levels in serum and had a significant effect on the reduction of transaminases measured in serum, which was confirmed by s.c. INSP052EC protein injections.

The decrease in ASAT and ALAT levels might be due to both, decreased TNF-alpha and IL-4 levels. TNF-alpha and IL-4 are important cytokines involved in the liver damage after ConA injection. In this mouse model of liver hepatitis TNF-alpha is mainly produced by hepatic macrophages, the so-called Kupfer cells, whereas IL-4 is produced by liver (natural killer T) NKT cells. Anti TNF-alpha antibodies confer protection against disease (Seino et al. 2001, Annals of surgery 234, 681-688) and inhibition of IL-4 production by NKT cells was shown to be hepato-protective in T-cell mediated hepatitis in mouse (Ajuebor et al. 2003 J. Immunology 170, 5252-9).

INSP052EC might be useful in treating auto-immune, viral or acute liver diseases as well as alcoholic liver failures. It might be also effective in other inflammatory diseases.

Example 7

Cytokine Expression Modulation Properties of INSP052EC-6His in LPS-induced Cytokine Release in Mice 7.1: Introduction The ability of INSP052EC to protect from the effects of cytokine release in vivo has been also tested by injecting either the recombinant protein or encapsulated, transiently transfected HEK293 cells expressing INSP052EC-6His in the model of LPS-induced TNF alpha and IL-6 release in mice.

Encapsulation of cells expressing a recombinant protein allows understanding of the possible therapeutic effects of a continuous administration of the protein in vivo, as shown with proteins with tumor suppressor function, for example (Visted T et al., 2003, Hum Gene Ther., 14, 1429-40).

LPS (Lipopolysaccharides) are an important component of the outer membranes of gram-negative bacteria and are the best characterised example of innate recognition that leads to a robust inflammatory response by macrophages or microglia cells via its binding to CD14 and the Toll receptor 4 (Lehnardt S et al., 2002, J Neurosci., 22, 2478-2486). LPS are widely used in literature to activate various cell types like macrophages, microglia and endothelial cells, in particular in relationship to liver diseases (Jirillo E et al., 2002, J Endotoxin Res., 8, 319-327).

7.2: Materials & Methods 7.2.1: Encapsulation of Transiently Transfected HEK293 Cells Expressing INSP052EC-6His 7.2.1.1: Cell Maintenance Human Embryonic Kidney 293 cells expressing the Epstein-Barr virus Nuclear Antigen (HEK293-EBNA, Invitrogen) were maintained in suspension in Ex-cell VPRO serum-free medium (maintenance medium, JRH, UK) supplemented with 4 mM L-Glutamine (Invitrogen) and 1 ml/L Phenol-Red-solution (0.5% w/v in water, Phenol Red: Sigma, USA) in spinner flasks (Techne, UK).

7.2.1.2: Cell transfection

At the day of transfection cells were centrifuged and re-suspended in a spinner vessel (DasGip, D) in 250 mL DMEM/F12 (1:1) medium containing 1% FBS and 4 ml/l ITS-X supplement (seeding medium, all Invitrogen) at a density of $1\times10^6$ cells/ml. Cells were transfected using the PEI method with a ratio of 2:1 PEI:DNA. In 100 mL seeding medium 500 µg of corresponding plasmid (pDEST12.2-INSP052EC) was mixed with 1 mg PEI (Polysciences, USA) and incubated for 10 minutes at room temperature. The mixture was added to the cell suspension and incubated for 90 minutes at 37° C. After the incubation the cell suspension was centrifuged (200×g, 10 minutes at 4° C.) and the cell pellet was re-suspended in 500 ml maintenance medium. Cells were incubated in a humidified atmosphere with 5% CO2 at 37° C. until encapsulation.

7.2.1.3: Cell Encapsulation

HEK293EBNA cells transfected with pDEST12.2-INSP052EC or not transfected (control cells) were encapsulated into Alginate-poly-L-Lysine-Alginate (APA) capsules using the Inotech research encapsulator (Inotech, CH). Cells were centrifuged (200×g 10 min 4° C.) and re-suspended in 2 ml washing buffer (all chemicals Inotech, CH). To this suspension a 1.5% alginate solution was slowly added to yield a final cell concentration of 2.5×10e6 cells/ml solution. The alginate-cell-suspension was taken up into a syringe. (Braun Omnifit, Braun, D), which was connected to the encapsulation machine.

The encapsulation was carried out using the following parameters:
Syringe Pump: 275 (50 ml Syringe) or 456 (20 ml Syringe)
Anode voltage: 1.16 kV
Vibration frequency: 1943 Hz
Vibration amplitude: 3
The protocol for encapsulation was the following:
Polymerisation buffer: 10 minutes (volume 250 ml)
Poly-L-Lysin: 10 minutes (volume 150 ml)
Washing buffer: 1 minute (volume 150 ml)
Washing buffer: 5 minutes (volume 150 ml)
0.03% Alginate: 5 minutes (volume 150 ml)
Washing buffer: 1 minute (volume 150 ml)
Depolymerisation buffer: 10 minutes (volume 300 ml)
Washing buffer: 1 minute (volume 150 ml)
Washing buffer: 5 minutes (volume 150 ml)
Medium (Excell-V-Pro): volume 100 ml All buffers were prepared according to the manufacturer's manual in sterile distilled water under sterile conditions. In the final step of the encapsulation, the capsules were re-suspended in 100 ml maintenance medium and transferred into a sterile spinner vessel (Dasgip, D). The capsules were incubated in a humidified atmosphere with 5% CO2 at 37 ° C. overnight or until injection into the animals.

7.2.2: LPS Induced Cytokine Release Model In Vivo

The model of LPS-induced TNF alpha and IL-6 release in mice was set up according to WO98/38179. Briefly, male C57/BL6 or C3H/HeN mice (8 weeks of age; Charles River, France) were used. In general, 10 animals per experimental group are used. Mice were maintained in standard conditions under a 12-hour light-dark cycle, provided irradiated food and water ad libitum.

LPS (O111:B4 (Sigma, Switzerland), 0.3 mg/kg) was injected s.c in mice. Ninety minutes later blood was sampled and plasma TNF alpha was determined using an ELISA kit (R&D). IL-6 levels were measured after 150 minutes using a commercial available ELISA kit (R&D Duoset ref. DY206). Dexamethasone, the reference compound, was solubilized in PBS and Dexamethasone (0.1 mg/kg, s.c.) was injected 15 minutes prior LPS.

The suspension containing the microcapsules containing HEK293 cells (control cells or cells transiently expressing INSP052EC-6His) was removed from the incubator and left several minutes in the laminar flow hood to allow the capsules to sediment. The clear supernatant was removed and the concentrated capsules were taken up carefully into a syringe. 700 µl capsules were injected slowly i.p. via a 0.7 mm needle (ref 53158.01 Polylabo, CH) per mouse. LPS injection was performed at day 3 after the injection of the capsules.

7.3: Results

The potential of INSP052EC to downregulate LPS-induced TNF alpha or IL-6 release in the blood was demonstrated in both models of INSP052EC administration.

Figure 10A:
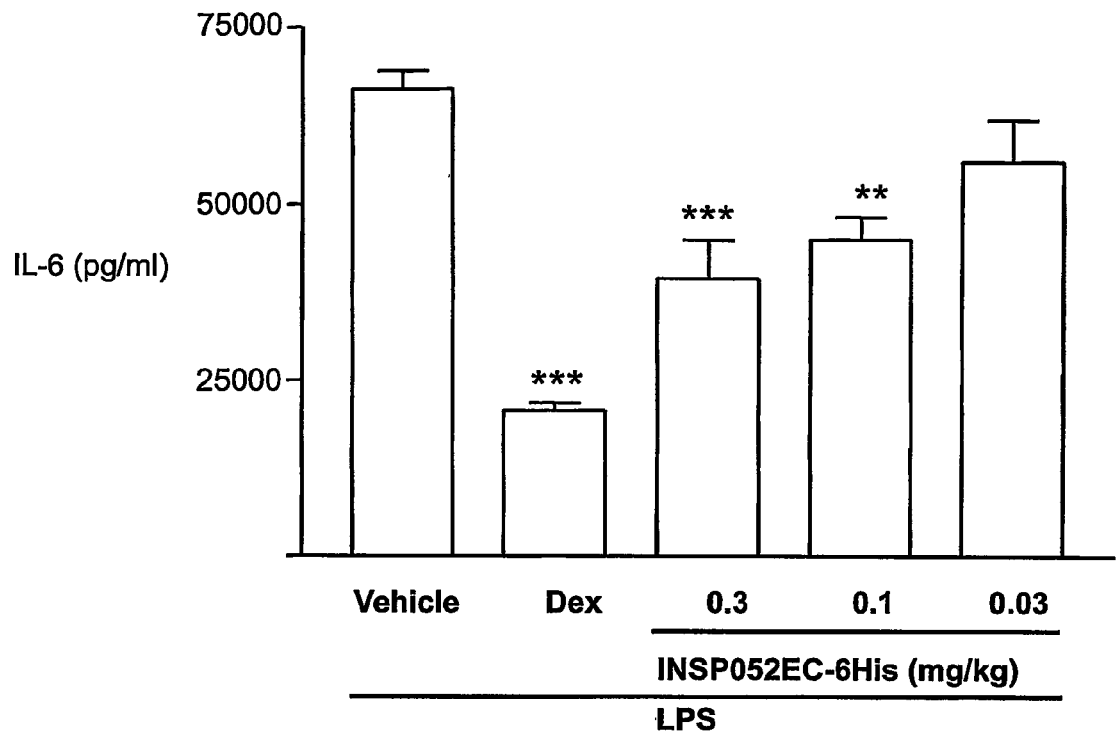
FIGS. 10A-10B: Effect of INSP052EC-6His injection prior to LPS administration on the release in the blood of IL-6 (A) or TNF alpha (B). The mice were treated with the protein at indicated concentration, with Dexamethasone (Dex; 0.1 mg/kg), or with the injection vehicle only (see Example 7). The asterisks indicate the level of statistical significance of the decrease (see FIG. 7).
Figure 10B:
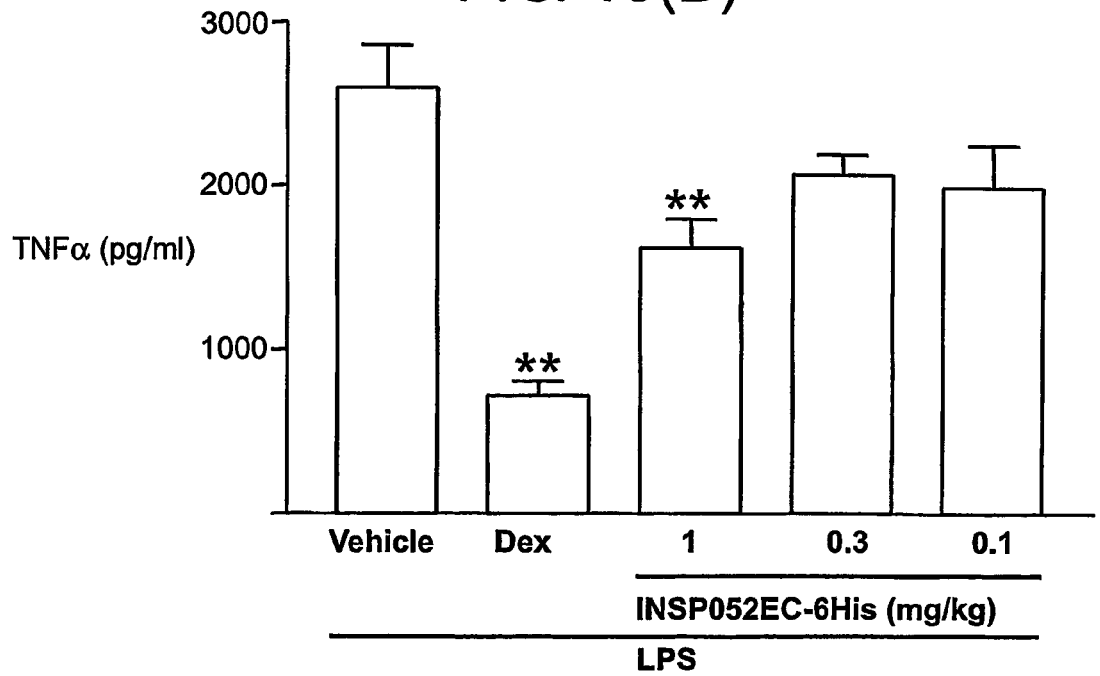

The injection of INSP052EC-6His 15 minutes prior to the LPS injection. decreases LPS-induced release of IL-6 (if INSP052EC-6His is administered at least at 0.1 mg/kg) and TNF alpha (if INSP052EC-6His is administered at least at 1 mg/kg) in a statistically significant manner, similarly to the reference compound Dexamethasone. Mice injected with the vehicle solution for injection (PBS-BSA with 0.02% glycerol) were used as negative controls (FIG. 10).

Figure 11:
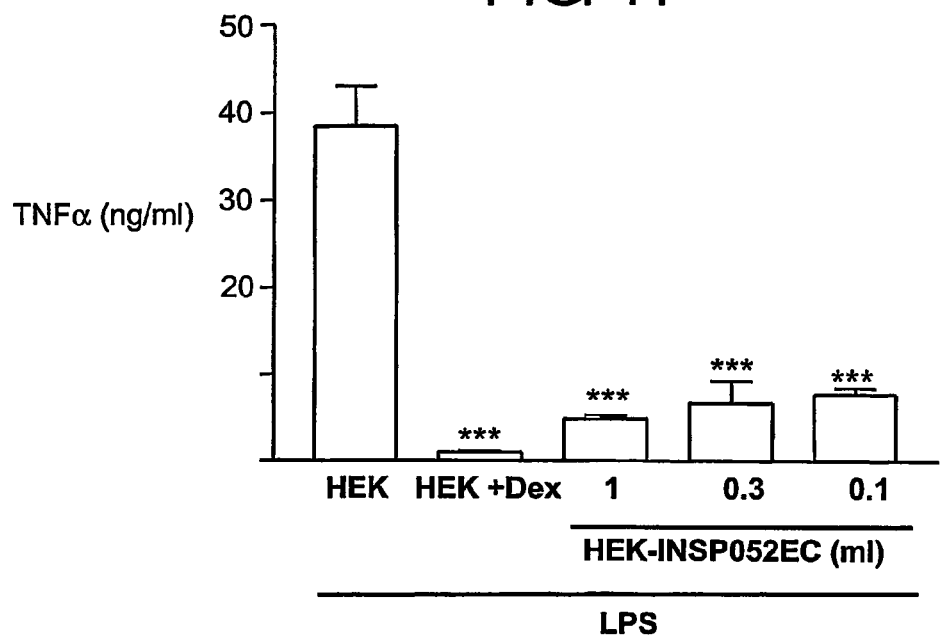
FIG. 11: Effect of HEK293 cells transiently expressing INSP052EC-6His on the LPS-induced release in the blood of TNF alpha. The mice were treated with the indicated volume of encapsulated cells expressing INSP052EC-6His, or with control cells (HEK) with or without Dexamethasone (Dex; 0.1 mg/kg) (see Example 7). The asterisks indicate the level of statistical significance of the decrease (see FIG. 7).

Similar positive effects were observed when the HEK293 cells transiently expressing INSP052EC-6His were injected in all the tested capsule volumes (FIG. 11).

Example 8

Properties of INSP052EC-6His in a model of Contact Hypersensitivity 8.1: Introduction INSP052EC was tested on hapten induced contact hypersensitivity (CHS), a murine model of inflammatory skin disease. CHS is a T cell-mediated inflammation model of the skin that represents a well established model for similar inflammations associated to diseases such allergic contact dermatitis and psoriasis, which are dermatological problems with unmet medical needs related to excessive cytokine production (Nakae S et al., 2003, Int Immunol., 15: 251-260; Gorbachev A V and Fairchild R L, 2001, Crit Rev Immunol., 21: 451-72).

8.2: Material and Methods

The hapten DNFB (2,4-dinitrofluorobenzene; Sigma Chemical Co.) was diluted in acetone/olive oil (4:1) immediately before use. Mice were sensitized with 30 µl of 0.5% DNFB solution painted to the shaved dorsal skin or left untreated. Mice were challenged five days later, i.e. CHS was elicited by applying a non-irritant dose of 10 µl of 0.2% DNFB onto both sides of the right ear and the same amount of solvent alone onto the left ear. Ear thickness was monitored at day 6 using a caliper (Mitutoya).

Ear swelling was calculated as ((T6−T5)right ear)−((T6−T5)left ear)

where T6 and T5 represent values of ear thickness at day 6 and day 5, respectively, after sensitization challenge, respectively. To assure that the observed swelling was due to DNFB specific inflammation rather than non-specific irritation, a non-sensitized but challenged group of mice was included with each experiment.

Mice were treated on Day 5 with an s.c injection of INSP052EC-6His in the indicated amount, Dexamethasone (1 mg/kg), or PBS only (control group).

8.3: Results

Figure 12:
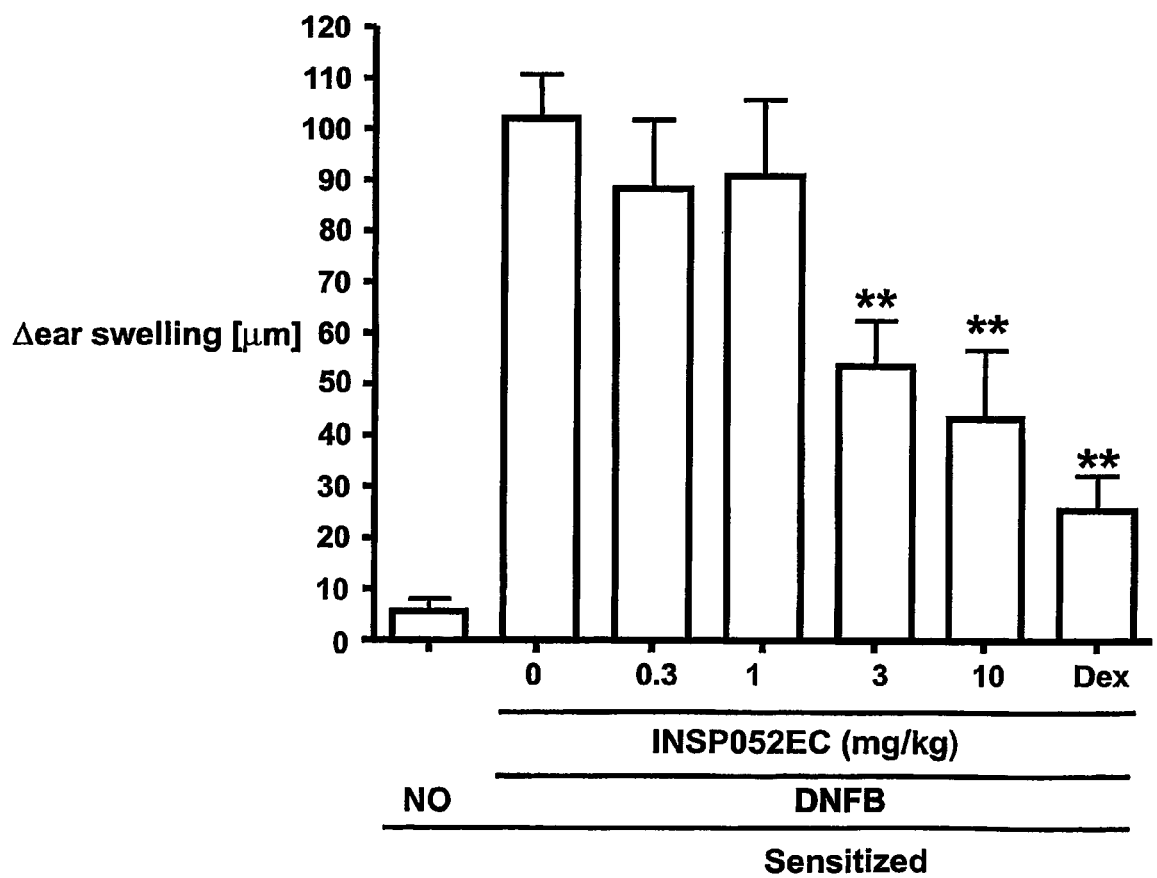
FIG. 12: Effect of INSP052EC-6His injection prior to LPS administration on the release in the blood of IL-6 (A) or TNF alpha (B). The mice were treated with the protein at indicated concentration, with Dexamethasone (Dex; 0.1 mg/kg), or with the injection vehicle only (see Example 8). The asterisks indicate the level of statistical significance of the decrease (see FIG. 7).

We show that INSP052EC reduces ear swelling in significant and dose dependent manner, suggesting a decrease in leukocyte infiltration and of the consequent inflammation (FIG. 12), demonstrating that INSP052EC can be useful in treating T cell-mediated inflammation of the skin, such as allergic contact dermatitis and psoriasis.

The examples clearly show that the isolated extracellular domain of INSP052 (INSP052EC) can be used (as such or as a variant or a fusion protein containing this protein sequence or the full length protein) for modulating cytokine activities, in particular as antagonist of cytokine secretion and/or expression, and may have a therapeutic role in diseases directly or indirectly related to both innate and adaptive immune responses.

The range of inhibiting activities shown by the tested INSP052EC-based molecule in different cell-based assays and animal models confirms that patho-physiological effects of cytokines, resulting from their excessive or inappropriately localized production can be blocked by using this molecule. The control of cellular events associated to prolonged production of proinflammatory cytokines can be obtained by INSP052EC-based molecules, which therefore can be used for antagonizing abnormal inflammatory states associated, in particular, to autoimmune and inflammatory diseases affecting various tissues and organs (e.g. liver, skin, lungs, central nervous system), providing as well a new therapeutic opportunity for oncological, neurological, cardiovascular, and infectious disorders. Additional clinical applications for INSP052EC-based molecules can be identified by using cytokine assays showing the excessive expression and/or secretion of cytokines in samples obtained by patients affected by other diseases (Wong C K and Lam C W, Adv Clin Chem. 2003, 37:1-46; Whiteside T L, Biotechniques, 2002, Oct. Suppl:4-8, 10, 12-5), then justifying the therapeutic use of a cytokine antagonist as INSP052EC-based molecules.

```
Sequence Information

Note: for amino acids encoded by exon-exon junctions, the amino acid
will be assigned to the more 5' exon.

SEQ ID NO 1: (INSP052 Nucleotide sequence exon1)
     1 ATGAAGAGAG AAAGGGGAGC CCTGTCCAGA GCCTCCAGGG CCCTGCGCCT TGCTCCTTTT

61 GTCTACCTTC TTCTGATCCA GACAG

SEQ ID NO 2: (INSP052 polypeptide sequence of Exon 1)
     1 MKRERGALSR ASRALRLAPF VYLLLIQTD SEQ ID NO 3: (INSP052 Nucleotide sequence exon2)
     1 ACCCCCTGGA GGGGGTGAAC ATCACCAGCC CCGTGCGCCT GATCCATGGC ACCGTGGGGA

61 AGTCGGCTCT GCTTTCTGTG CAGTACAGCA GTACCAGCAG CGACAGGCCT GTAGTGAAGT
```

```
                       -continued
121 GGCAGCTGAA GCGGGACAAG CCAGTGACCG TGGTGCAGTC CATTGGCACA GAGGTCATCG

181 GCACCCTGCG GCCTGACTAT CGAGACCGTA TCCGACTCTT TGAAAATGGC TCCCTGCTTC

241 TCAGCGACCT GCAGCTGGCC GATGAGGGCA CCTATGAGGT CGAGATCTCC ATCACCGACG

301 ACACCTTCAC TGGGGAGAAG ACCATCAACC TTACTGTAGA TG
```

SEQ ID NO 4: (INSP052 Protein Sequence of Exon 2)
```
  1 PLEGVNITSP VRLIHGTVGK SALLSVQYSS TSSDRPVVKW QLKRDKPVTV VQSIGTEVIG

61 TLRPDYRDRI RLFENGSLLL SDLQLADEGT YEVEISITDD TFTGEKTINL TVDV
```

SEQ ID NO 5: (INSP052 Nucleotide sequence Exon3)
```
  1 TGCCCATTTC GAGGCCACAG GTGTTGGTGG CTTCAACCAC TGTGCTGGAG CTCAGCGAGG

61 CCTTCACCTT GAACTGCTCA CATGAGAATG GCACCAAGCC CAGCTACACC TGGCTGAAGG

121 ATGGCAAGCC CCTCCTCAAT GACTCGAGAA TGCTCCTGTC CCCCGACCAA AAGGTGCTCA

181 CCATCACCCG CGTGCTCATG GAGGATGACG ACCTGTACAG CTGCATGGTG GAGAACCCCA

241 TCAGCCAGGG CCGCAGCCTG CCTGTCAAGA TCACCGTATA CA
```

SEQ ID NO 6: (INSP052 Polypeptide sequence of Exon 3)
```
  1 PISRPQVLVA STTVLELSEA FTLNCSHENG TKPSYTWLKD GKPLLNDSRM LLSPDQKVLT

61 ITRVLMEDDD LYSCMVENPI SQGRSLPVKI TVYR
```

SEQ ID NO 7: (INSP052 Nucleotide Sequence Exon 4)
```
  1 GAAGAAGCTC CCTTTACATC ATCTTGTCTA CAGGAGGCAT CTTCCTCCTT GTGACCTTGG

61 TGACAGTCTG TGCCTGCTGG AAACCCTCCA AAAG
```

SEQ ID NO 8: (INSP052 Polypeptide sequence of Exon 4)
```
  1 RSSLYIILST GGIFLLVTLV TVCACWKPSK R
```

SEQ ID NO 9: (INSP052 Nucleotide Sequence Exon 5)
```
  1 GAAACAGAAG AAGCTAGAAA AGCAAAACTC CCTGGAATAC ATGGATCAGA ATGATGACCG

61 CCTGAAACCA GAAG
```

SEQ ID NO 10: (INSP052 Polypeptide Sequence Exon 5)
```
  1 KQKKLEKQNS LEYMDQNDDR LKPEA
```

SEQ ID NO 11: (INSP052 Nucleotide Sequence Exon 6)
```
  1 CAGACACCCT CCCTCGAAGT GGTGAGCAGG AACGGAAGAA CCCCATGGCA CTCTATATCC

61 TGAAGGACAA G
```

SEQ ID NO 12: (INSP052 Polypeptide Sequence Exon 6)
```
  1 DTLPRSGEQE RKNPMALYIL KDK
```

SEQ ID NO 13: (INSP052 Nucleotide Sequence Exon 7)
```
  1 GACTCCCCGG AGACCGAGGA GAACCCGGCC CCGGAGCCTC GAAGCGCGAC GGAGCCCGGC

61 CCGCCCGGCT ACTCCGTGTC TCCCGCCGTG CCCGGCCGCT CGCCGGGGCT GCCCATCCGC

121 TCTGCCCGCC GCTACCCGCG CTCCCCAGCG CGCTCCCCAG CCACCGGCCG GACACACTCG

181 TCGCCGCCCA GGGCCCCGAG CTCGCCCGGC CGCTCGCGCA CGCCTCGCG CACACTGCGG

241 ACTGCGGGCG TGCACATAAT CCGCGAGCAA GACGAGGCCG GCCCGGTGGA GATCAGCGCC

301 TGA
```

SEQ ID NO 14: (INSP052 Polypeptide sequence for exon 7)
```
  1 DSPETEENPA PEPRSATEPG PPGYSVSPAV PGRSPGLPIR SARRYPRSPA RSPATGRTHS

61 SPPRAPSSPG RSRSASRTLR TAGVHIIREQ DEAGPVEISA
```

SEQ ID NO :15 (INSP052 Combined Nucleotide sequence exons 1, 2, 3, 4, 5, 6 and 7)
```
  1 ATGAAGAGAG AAAGGGGAGC CCTGTCCAGA GCCTCCAGGG CCCTGCGCCT TGCTCCTTTT

61 GTCTACCTTC TTCTGATCCA GACAGACCCC CTGGAGGGGG TGAACATCAC CAGCCCCGTG

121 CGCCTGATCC ATGGCACCGT GGGGAAGTCG GCTCTGCTTT CTGTGCAGTA CAGCAGTACC

181 AGCAGCGACA GGCCTGTAGT GAAGTGGCAG CTGAAGCGGG ACAAGCCAGT GACCGTGGTG
```

-continued

```
 241 CAGTCCATTG GCACAGAGGT CATCGGCACC CTGCGGCCTG ACTATCGAGA CCGTATCCGA
 301 CTCTTTGAAA ATGGCTCCCT GCTTCTCAGC GACCTGCAGC TGGCCGATGA GGGCACCTAT
 361 GAGGTCGAGA TCTCCATCAC CGACGACACC TTCACTGGGG AGAAGACCAT CAACCTTACT
 421 GTAGATGTGC CCATTTCGAG GCCACAGGTG TTGGTGGCTT CAACCACTGT GCTGGAGCTC
 481 AGCGAGGCCT TCACCTTGAA CTGCTCACAT GAGAATGGCA CCAAGCCCAG CTACACCTGG
 541 CTGAAGGATG GCAAGCCCCT CCTCAATGAC TCGAGAATGC TCCTGTCCCC CGACCAAAAG
 601 GTGCTCACCA TCACCCGCGT GCTCATGGAG GATGACGACC TGTACAGCTG CATGGTGGAG
 661 AACCCCATCA GCCAGGGCCG CAGCCTGCCT GTCAAGATCA CCGTATACAG AAGAAGCTCC
 721 CTTTACATCA TCTTGTCTAC AGGAGGCATC TTCCTCCTTG TGACCTTGGT GACAGTCTGT
 781 GCCTGCTGGA AACCCTCCAA AAGGAAACAG AAGAAGCTAG AAAAGCAAAA CTCCCTGGAA
 841 TACATGGATC AGAATGATGA CCGCCTGAAA CCAGAAGCAG ACACCCTCCC TCGAAGTGGT
 901 GAGCAGGAAC GGAAGAACCC CATGGCACTC TATATCCTGA AGGACAAGGA CTCCCCGGAG
 961 ACCGAGGAGA ACCCGGCCCC GGAGCCTCGA AGCGCGACGG AGCCCGGCCC GCCCGGCTAC
1021 TCCGTGTCTC CCGCCGTGCC CGGCCGCTCG CCGGGGCTGC CCATCCGCTC TGCCCGCCGC
1081 TACCCGCGCT CCCCAGCGCG CTCCCCAGCC ACCGGCCGGA CACACTCGTC GCCGCCCAGG
1141 GCCCCGAGCT CGCCCGGCCG CTCGCGCAGC GCCTCGCGCA CACTGCGGAC TGCGGGCGTG
1201 CACATAATCC GCGAGCAAGA CGAGGCCGGC CCGGTGGAGA TCAGCGCCTG A
```

SEQ ID NO: 16 (INSP052 Combined polypeptide sequence for exons 1, 2, 3, 4, 5, 6 and 7.)

```
  1 MKRERGALSR ASRALRLAPF VYLLLIQTDP LEGVNITSPV RLIHGTVGKS ALLSVQYSST
 61 SSDRPVVKWQ LKRDKPVTVV QSIGTEVIGT LRPDYRDRIR LFENGSLLLS DLQLADEGTY
121 EVEISITDDT FTGEKTINLT VDVPISRPQV LVASTTVLEL SEAFTLNCSH ENGTKPSYTW
181 LKDGKPLLND SRMLLSPDQK VLTITRVLME DDDLYSCMVE NPISQGRSLP VKITVYRRSS
241 LYIILSTGGI FLLVTLVTVC ACWKPSKRKQ KKLEKQNSLE YMDQNDDRLK PEADTLPRSG
301 EQERKNPMAL YILKDKDSPE TEENPAPEPR SATEPGPPGY SVSPAVPGRS PGLPIRSARR
361 YPRSPARSPA TGRTHSSPPR APSSPGRSRS ASRTLRTAGV HIIREQDEAG PVEISA
```

SEQ ID NO: 17 (INSP055 Mouse virtual cDNA)

```
  1 ATGAAGAGAG AAAGGGGAGC CCTGTCAAGA GCCTCCAGGG CTCTGCGCCT CTCTCCTTTT
 61 GTCTACCTGC TTCTCATCCA GCCAGTCCCC CTGGAGGGGG TGAACATCAC CAGCCCAGTA
121 CGTCTGATCC ACGGCACAGT GGGGAAGTCG GCCCTGCTTT CCGTGCAGTA CAGTAGCACC
181 AGCAGCGACA GCCCGTGGGT GAAGTGGCAG CTGAAGCGTG ACAAGCCAGT GACCGTGGTG
241 CAGTCTATAG GCACAGAGGT CATTGGCACT CTGCGGCCTG ACTATCGAGA CCGTATCCGG
301 CTCTTTGAAA ATGGCTCCTT GCTTCTCAGC GACCTGCAGC TGGCGGATGA GGGAACCTAT
361 GAAGTGGAGA TTTCCATCAC TGACGACACC TTCACCGGGG AGAAGACCAT CAACCTCACC
421 GTGGATGTGC CCATTTCAAG GCCGCAGGTA TTAGTGGCTT CAACCACTGT GCTGGAGCTC
481 AGTGAGGCCT TCACCCTCAA CTGCTCCCAT GAGAATGGCA CCAAGCCTAG CTACACGTGG
541 CTGAAGGATG GCAAACCCCT CCTCAATGAC TCCCGAATGC TCCTGTCCCC TGACCAAAAG
601 GTGCTCACCA TCACCCGAGT ACTCATGGAA GATGACGACC TGTACAGCTG TGTGGTGGAG
661 AACCCCATCA GCCAGGTCCG CAGCCTGCCT GTCAAGATCA CTGTGTATAG AAGAAGCTCC
721 CTCTATATCA TCTTGTCTAC AGGAGGCATC TTCCTCCTTG TGACCCTGGT GACAGTTTGT
781 GCCTGCTGGA AACCCTCAAA AAAGTCTAGG AAGAAGAGGA AGTTGGAGAA GCAAAACTCC
```

-continued

```
  841 TTGGAATACA TGGATCAGAA TGATGACCGC CTAAAATCAG AAGCAGATAC CCTACCCCGA

901 AGTGGAGAAC AGGAGCGGAA GAACCCAATG GCACTCTATA TCCTGAAGGA TAAGGATTCC

961 TCAGAGCCAG ATGAAAACCC TGCTACAGAG CCACGGAGCA CCACAGAACC CGGTCCCCCT

1021 GGCTACTCCG TGTCGCCGCC CGTGCCCGGC CGCTCTCCGG GGCTTCCCAT CCGCTCAGCC

1081 CGCCGCTACC CGCGCTCCCC AGCACGTTCC CCTGCCACTG GCCGGACGCA CACGTCGCCA

1141 CCGCGGGCCC CGAGCTCGCC AGGCCGCTCG CGCAGCTCTT CGCGCTCACT GCGGACTGCA

1201 GGCGTGCAGA GAATCCGGGA GCAGGACGAG TCAGGGCAGG TGGAGATCAG TGCCTGA
```

SEQ ID NO: 18 (INSP055 Mouse Predicted Protein)
```
    1 MKRERGALSR ASRALRLSPF VYLLLIQPVP LEGVNITSPV RLIHGTVGKS ALLSVQYSST

61 SSDKPVVKWQ LKRDKPVTVV QSIGTEVIGT LRPDYRDRIR LFENGSLLLS DLQLADEGTY

121 EVEISITDDT FTGEKTINLT VDVPISRPQV LVASTTVLEL SEAFTLNCSH ENGTKPSYTW

181 LKDGKPLLND SRMLLSPDQK VLTITRVLME DDDLYSCVVE NPISQVRSLP VKITVYRRSS

241 LYIILSTGGI FLLVTLVTVC ACWKPSKKSR KKRKLEKQNS LEYMDQNDDR LKSEADTLPR

301 SGEQERKNPM ALYILKDKDS SEPDENPATE PRSTTEPGPP GYSVSPPVPG RSPGLPIRSA

361 RRYPRSPARS PATGRTHTSP PRAPSSPGRS RSSSRSLRTA GVQRIREQDE SGQVEISA
```

SEQ ID NO: 19 (nucleic acid sequence coding for extracellular domain of INSP052)
```
    1 ATGAAGAGAG AAAGGGGAGC CCTGTCCAGA GCCTCCAGGG CCCTGCGCCT TGCTCCTTTT

61 GTCTACCTTC TTCTGATCCA GACAGACCCC CTGGAGGGGG TGAACATCAC CAGCCCCGTG

121 CGCCTGATCC ATGGCACCGT GGGGAAGTCG GCTCTGCTTT CTGTGCAGTA CAGCAGTACC

181 AGCAGCGACA GGCCTGTAGT GAAGTGGCAG CTGAAGCGGG ACAAGCCAGT GACCGTGGTG

241 CAGTCCATTG GCACAGAGGT CATCGGCACC CTGCGGCCTG ACTATCGAGA CCGTATCCGA

301 CTCTTTGAAA ATGGCTCCCT GCTTCTCAGC GACCTGCAGC TGGCCGATGA GGGCACCTAT

361 GAGGTCGAGA TCTCCATCAC CGACGACACC TTCACTGGGG AGAAGACCAT CAACCTTACT

421 GTAGATGTGC CCATTTCGAG GCCACAGGTG TTGGTGGCTT CAACCACTGT GCTGGAGCTC

481 AGCGAGGCCT TCACCTTGAA CTGCTCACAT GAGAATGGCA CCAAGCCCAG CTACACCTGG

541 CTGAAGGATG GCAAGCCCCT CCTCAATGAC TCGAGAATGC TCCTGTCCCC CGACCAAAAG

601 GTGCTCACCA TCACCCGCGT GCTCATGGAG GATGACGACC TGTACAGCTG CATGGTGGAG

661 AACCCCATCA GCCAGGGCCG CAGCCTGCCT GTCAAGATCA CCGTATACAG AAGAAGCTCC
```

SEQ ID NO: 20 (extracellular domain of INSP052)
```
    1 MKRERGALSR ASRALRLAPF VYLLLIQTDP LEGVNITSPV RLIHGTVGKS ALLSVQYSST

61 SSDRPVVKWQ LKRDKPVTVV QSIGTEVIGT LRPDYRDRIR LFENGSLLLS DLQLADEGTY

121 EVEISITDDT FTGEKTINLT VDVPISRPQV LVASTTVLEL SEAFTLNCSH ENGTKPSYTW

181 LKDGKPLLND SRMLLSPDQK VLTITRVLME DDDLYSCMVE NPISQGRSLP VKITVYRRSS
```

SEQ ID NO: 21 (nucleic acid sequence coding for the extracellular domain of mature INSP052)
```
    1 GTGAACATCA CCAGCCCCGT GCGCCTGATC CATGGCACCG TGGGGAAGTC

51 GGCTCTGCTT TCTGTGCAGT ACAGCAGTAC CAGCAGCGAC AGGCCTGTAG

101 TGAAGTGGCA GCTGAAGCGG GACAAGCCAG TGACCGTGGT GCAGTCCATT

151 GGCACAGAGG TCATCGGCAC CCTGCGGCCT GACTATCGAG ACCGTATCCG

201 ACTCTTTGAA AATGGCTCCC TGCTTCTCAG CGACCTGCAG CTGGCCGATG

251 AGGGCACCTA TGAGGTCGAG ATCTCCATCA CCGACGACAC CTTCACTGGG

301 GAGAAGACCA TCAACCTTAC TGTAGATGTG CCCATTTCGA GGCCACAGGT
```

```
351 GTTGGTGGCT TCAACCACTG TGCTGGAGCT CAGCGAGGCC TTCACCTTGA

401 ACTGCTCACA TGAGAATGGC ACCAAGCCCA GCTACACCTG GCTGAAGGAT

451 GGCAAGCCCC TCCTCAATGA CTCGAGAATG CTCCTGTCCC CCGACCAAAA

501 GGTGCTCACC ATCACCCGCG TGCTCATGGA GGATGACGAC CTGTACAGCT

551 GCATGGTGGA GAACCCCATC AGCCAGGGCC GCAGCCTGCC TGTCAAGATC

601 ACCGTATACA GAAGAAGCTC C
```

SEQ ID NO: 22 (extracellular domain of mature INSP052)
```
  1 VNITSPVRLI HGTVGKSALL SVQYSSTSSD RPVVKWQLKR DKPVTVVQSI

51 GTEVIGTLRP DYRDRIRLFE NGSLLLSDLQ LADEGTYEVE ISITDDTFTG

101 EKTINLTVDV PISRPQVLVA STTVLELSEA FTLNCSHENG TKPSYTWLKD

151 GKPLLNDSRM LLSPDQKVLT ITRVLMEDDD LYSCMVENPI SQGRSLPVKI

201 TVYRRSS
```

SEQ ID NO 23: (Nucleotide sequence encoding the mature INSP052 exon2)
```
  1 GTGAACATCA CCAGCCCCGT GCGCCTGATC CATGGCACCG TGGGGAAGTC

51 GGCTCTGCTT TCTGTGCAGT ACAGCAGTAC CAGCAGCGAC AGGCCTGTAG

101 TGAAGTGGCA GCTGAAGCGG GACAAGCCAG TGACCGTGGT GCAGTCCATT

151 GGCACAGAGG TCATCGGCAC CCTGCGGCCT GACTATCGAG ACCGTATCCG

201 ACTCTTTGAA AATGGCTCCC TGCTTCTCAG CGACCTGCAG CTGGCCGATG

251 AGGGCACCTA TGAGGTCGAG ATCTCCATCA CCGACGACAC CTTCACTGGG

301 GAGAAGACCA TCAACCTTAC TGTAGATG
```

SEQ ID NO 24: (Protein Sequence of Mature INSP052 Exon 2)
```
  1 VNITSPVRLI HGTVGKSALL SVQYSSTSSD RPVVKWQLKR DKPVTVVQSI

51 GTEVIGTLRP DYRDRIRLFE NGSLLLSDLQ LADEGTYEVE ISITDDTFTG

101 EKTINLTVDV
```

SEQ ID NO :25 (nucleotide sequence encoding the mature INSP052 polypeptide)
```
  1 GTGAACATCA CCAGCCCCGT GCGCCTGATC CATGGCACCG TGGGGAAGTC

51 GGCTCTGCTT TCTGTGCAGT ACAGCAGTAC CAGCAGCGAC AGGCCTGTAG

101 TGAAGTGGCA GCTGAAGCGG GACAAGCCAG TGACCGTGGT GCAGTCCATT

151 GGCACAGAGG TCATCGGCAC CCTGCGGCCT GACTATCGAG ACCGTATCCG

201 ACTCTTTGAA AATGGCTCCC TGCTTCTCAG CGACCTGCAG CTGGCCGATG

251 AGGGCACCTA TGAGGTCGAG ATCTCCATCA CCGACGACAC CTTCACTGGG

301 GAGAAGACCA TCAACCTTAC TGTAGATGTG CCCATTTCGA GGCCACAGGT

351 GTTGGTGGCT TCAACCACTG TGCTGGAGCT CAGCGAGGCC TTCACCTTGA

401 ACTGCTCACA TGAGAATGGC ACCAAGCCCA GCTACACCTG GCTGAAGGAT

451 GGCAAGCCCC TCCTCAATGA CTCGAGAATG CTCCTGTCCC CCGACCAAAA

501 GGTGCTCACC ATCACCCGCG TGCTCATGGA GGATGACGAC CTGTACAGCT

551 GCATGGTGGA GAACCCCATC AGCCAGGGCC GCAGCCTGCC TGTCAAGATC

601 ACCGTATACA GAAGAAGCTC CTTTACATC ATCTTGTCTA CAGGAGGCAT

651 CTTCCTCCTT GTGACCTTGG TGACAGTCTG TGCCTGCTGG AAACCCTCCA

701 AAAGGAAACA GAAGAAGCTA GAAAAGCAAA ACTCCCTGGA ATACATGGAT

751 CAGAATGATG ACCGCCTGAA ACCAGAAGCA GACACCCTCC CTCGAAGTGG
```

```
 801 TGAGCAGGAA CGGAAGAACC CCATGGCACT CTATATCCTG AAGGACAAGG

851 ACTCCCCGGA GACCGAGGAG AACCCGGCCC CGGAGCCTCG AAGCGCGACG

901 GAGCCCGGCC CGCCCGGCTA CTCCGTGTCT CCCGCCGTGC CCGGCCGCTC

951 GCCGGGGCTG CCCATCCGCT CTGCCCGCCG CTACCCGCGC TCCCCAGCGC

1001 GCTCCCCAGC CACCGGCCGG ACACACTCGT CGCCGCCCAG GGCCCCGAGC

1051 TCGCCCGGCC GCTCGCGCAG CGCCTCGCGC ACACTGCGGA CTGCGGGCGT

1101 GCACATAATC CGCGAGCAAG ACGAGGCCGG CCCGGTGGAG ATCAGCGCCT

1151 GA
```

SEQ ID NO: 26 (INSP052 mature polypeptide sequence)
```
   1 VNITSPVRLI HGTVGKSALL SVQYSSTSSD RPVVKWQLKR DKPVTVVQSI

51 GTEVIGTLRP DYRDRIRLFE NGSLLLSDLQ LADEGTYEVE ISITDDTFTG

101 EKTINLTVDV PISRPQVLVA STTVLELSEA FTLNCSHENG TKPSYTWLKD

151 GKPLLNDSRM LLSPDQKVLT ITRVLMEDDD LYSCMVENPI SQGRSLPVKI

201 TVYRRSSLYI ILSTGGIFLL VTLVTVCACW KPSKRKQKKL EKQNSLEYMD

251 QNDDRLKPEA DTLPRSGEQE RKNPMALYIL KDKDSPETEE NPAPEPRSAT

301 EPGPPGYSVS PAVPGRSPGL PIRSARRYPR SPARSPATGR THSSPPRAPS

351 SPGRSRSASR TLRTAGVHII REQDEAGPVE ISA
```

SEQ ID NO: 27 (SEQ ID NO 880)
```
   1 MKRERGALSR ASRALRLAPF VYLLLIQTDP LEGVNITSPV RLIHGTVGKS

51 ALLSVQYSST SSDRPVVKWQ LKRDKPVTVV QSIGTEVIGT LRPDYRDRIR

101 LFENGSLLLS DLQLADEGTY EVEISITDDT FTGEKTINLT VDVPISRPQV

151 LVASTTVLEL SEAFTLNCSH ENGTKPSYTW LKDGKPLLND SRMLLSPDQK

201 VLTITRVLME DDDLDSCVVE NPINQGRTLP CKITVYKKSS LSSIWLQEAF

251 SSLGPW
```

SEQ ID NO: 28 (SEQ ID NO 434)
```
   1 MKRERGALSR ASRALRLAPF VYLLLIQTDP LEGVNITSPV RLIHGTVGKS

51 ALLSVQYSST SSDRPVVKWQ LKRDKPVTVV QSIGTEVIGT LRPDYRDRIR

101 LFENGSLLLS DLQLADEGTY EVEISITDDT FTGEKTINLT VDVPISRPQV

151 LVASTTVLEL SEAFTLNCSH ENGTKPSYTW LKDGKPLLND SRMLLSPDQK

201 VLTITRVLME DDDLDSCVVE NPINQGRTLP CKITVYKKSS FYIICLKEAS

251 SSFGPW
```

SEQ ID NO: 29 (histidine-tagged, extracellular domain of mature INSP052)
```
   1 VNITSPVRLI HGTVGKSALL SVQYSSTSSD RPVVKWQLKR DKPVTVVQSI

51 GTEVIGTLRP DYRDRIRLFE NGSLLLSDLQ LADEGTYEVE ISITDDTFTG

101 EKTINLTVDV PISRPQVLVA STTVLELSEA FTLNCSHENG TKPSYTWLKD

151 GKPLLNDSRM LLSPDQKVLT ITRVLMEDDD LYSCMVENPI SQGRSLPVKI

201 TVYRRSSHHH HHH
```

SEQ ID NO: 30 (Fc fusion of the extracellular domain of mature INSP052)
```
   1 VNITSPVRLI HGTVGKSALL SVQYSSTSSD RPVVKWQLKR DKPVTVVQSI

51 GTEVIGTLRP DYRDRIRLFE NGSLLLSDLQ LADEGTYEVE ISITDDTFTG

101 EKTINLTVDV PISRPQVLVA STTVLELSEA FTLNCSHENG TKPSYTWLKD

151 GKPLLNDSRM LLSPDQKVLT ITRVLMEDDD LYSCMVENPI SQGRSLPVKI
```

-continued

```
 201 TVYRRSSEPK SCDKTHTCPP CPAPELLGGP SVFLFPPKPK DTLMISRTPE

251 VTCVVVDVSH EDPEVKFNWY VDGVEVHNAK TKPREEQYNS TYRVVSVLTV

301 LHQDWLNGKE YKCKVSNKAL PAPIEKTISK AKGQPREPQV YTLPPSREEM

351 TKNQVSLTCL VKGFYPSDIA VEWESNGQPE NNYKTTPPVL DSDGSFFLYS

401 KLTVDKSRWQ QGNVFSCSVM HEALHNHYTQ KSLSLSPGK

SEQ ID NO: 31 (INSP052Ig2)
   1 VRLIHGTVGK SALLSVQYSS TSSDRPVVKW QLKRDKPVTV VQSIGTEVIG

51 TLRPDYRDRI RLFENGSLLL SDLQLADEGT YEVEISITDD TFTGEKTINL

101 TVDVPISRPQ VLVASTTVLE LSEAFTLNCS HENGTKPSYT WLKDGKPLLN

151 DSRMLLSPDQ KVLTITRVLM EDDDLYSCMV ENPISQ
```

We claim:

1. A method of treating acute liver disease or inflammatory skin disease comprising administering to an individual having acute liver disease or inflammatory skin disease a composition comprising a pharmaceutically acceptable carrier and a polypeptide, said polypeptide:
   a) consisting of SEQ ID NO:22;
   b) consisting of SEQ ID NO:20;
   c) comprising SEQ ID NO:29; or
   d) comprising SEQ ID NO:30.

2. The method according to claim 1, wherein said polypeptide comprises SEQ ID NO: 29.

3. The method according to claim 1, wherein said polypeptide comprises SEQ ID NO: 30.

4. The method according to claim 1, wherein said polypeptide consists of SEQ ID NO: 20.

5. The method according to claim 1, wherein said polypeptide consists of SEQ ID NO: 29.

6. The method according to claim 1, wherein said polypeptide consists of SEQ ID NO: 30.

7. A method of decreasing TNF-α levels or IL-6 levels in an individual comprising the administration of a composition comprising a pharmaceutically acceptable carrier and a polypeptide, said composition being administered in an amount that reduces TNF-α levels or IL-6 levels in said individual and said polypeptide:
- a) comprising SEQ ID NO: 20;
- b) comprising SEQ ID NO: 29;
- c) comprising SEQ ID NO: 30; or
- d) comprising SEQ ID NO: 22; and
- wherein said TNF-α or IL-6 levels are determined to be reduced.

8. A method of decreasing TNF-α levels or IL-6 levels in an individual comprising the administration of a composition comprising a pharmaceutically acceptable carrier and a polypeptide, said composition being administered in an amount that reduces TNF-α levels or IL-6 levels in said individual and said polypeptide:
- a) consisting of SEQ ID NO: 20;
- b) consisting of SEQ ID NO: 27;
- c) consisting of SEQ ID NO: 28;
- d) consisting of SEQ ID NO: 29;
- e) consisting of SEQ ID NO: 30; or
- f) consisting of SEQ ID NO: 22.

* * * * *

UNITED STATES PATENT AND TRADEMARK OFFICE
CERTIFICATE OF CORRECTION

PATENT NO. : 7,803,383 B2
APPLICATION NO. : 10/579113
DATED : September 28, 2010
INVENTOR(S) : Richard Joseph Fagan et al.

It is certified that error appears in the above-identified patent and that said Letters Patent is hereby corrected as shown below:

Column 3,
Line 10, "R W Sernin" should read --R W Semin--.
Line 39, "57-68, Matsuno" should read --57-68; Matsuno--.

Column 6,
Line 54, "IL-Ira" should read --IL-1ra--.

Column 7,
Line 34, "cytoldnes" should read --cytokines--.

Column 9,
Line 52, "1NSP052" should read --INSP052--.

Column 15,
Line 45, "cytoline" should read --cytokine--.

Column 16,
Line 40, "fimgal infection" should read --fungal infection--.

Column 25,
Line 28, "(1988);." should read --(1988);--.

Column 35,
Line 7, "Immunex" should read --(Immunex--.

Column 41,
Line 36, "bacterial. toxoid" should read --bacterial toxoid--.

Signed and Sealed this
Fifteenth Day of February, 2011

David J. Kappos
*Director of the United States Patent and Trademark Office*

Column 43,
Line 27, "Proc. Nati." should read --Proc. Natl.--.

Column 44,
Line 66, "inyention" should read --invention--.

Column 45,
Line 29, "bums" should read --burns--.

Column 46,
Line 20, "HPBMC" should read --hPBMC--.
Line 28, "protein in The IC50" should read --protein in µg/ml). The IC50--.

Column 48,
Line 33, "IgGI" should read --IgG1--.

Column 53,
Line 19, "IFN-garnma" should read --IFN-gamma--.
Line 67, "25 µof" should read --25 µl of--.

Column 54,
Line 46, "CDNA" should read --cDNA--.
Line 64, "already show" should read --already shown--.

SEQUENCE LISTING

```
<160> NUMBER OF SEQ ID NOS: 32

<210> SEQ ID NO 1
<211> LENGTH: 85
<212> TYPE: DNA
<213> ORGANISM: Homo sapiens

<400> SEQUENCE: 1
atgaagagag aaaggggagc cctgtccaga gcctccaggg ccctgcgcct tgctcctttt    60
gtctaccttc ttctgatcca gacag                                         85

<210> SEQ ID NO 2
<211> LENGTH: 29
<212> TYPE: PRT
<213> ORGANISM: Homo sapiens

<400> SEQUENCE: 2

Met Lys Arg Glu Arg Gly Ala Leu Ser Arg Ala Ser Arg Ala Leu Arg
1               5                   10                  15

Leu Ala Pro Phe Val Tyr Leu Leu Leu Ile Gln Thr Asp
            20                  25

<210> SEQ ID NO 3
<211> LENGTH: 342
<212> TYPE: DNA
<213> ORGANISM: Homo sapiens

<400> SEQUENCE: 3 acccccctgga gggggtgaac atcaccagcc ccgtgcgcct gatccatggc accgtgggga   60
agtcggctct gctttctgtg cagtacagca gtaccagcag cgacaggcct gtagtgaagt   120
ggcagctgaa gcgggacaag ccagtgaccg tggtgcagtc cattggcaca gaggtcatcg   180 gcacccctgcg gcctgactat cgagaccgta tccgactctt tgaaaatggc tccctgcttc   240
tcagcgacct gcagctggcc gatgagggca cctatgaggt cgagatctcc atcaccgacg   300
acaccttcac tggggagaag accatcaacc ttactgtaga tg                     342

<210> SEQ ID NO 4
<211> LENGTH: 114
<212> TYPE: PRT
<213> ORGANISM: Homo sapiens
```

<400> SEQUENCE: 4

```
Pro Leu Glu Gly Val Asn Ile Thr Ser Pro Val Arg Leu Ile His Gly
1               5                   10                  15

Thr Val Gly Lys Ser Ala Leu Leu Ser Val Gln Tyr Ser Ser Thr Ser
            20                  25                  30

Ser Asp Arg Pro Val Val Lys Trp Gln Leu Lys Arg Asp Lys Pro Val
        35                  40                  45

Thr Val Val Gln Ser Ile Gly Thr Glu Val Ile Gly Thr Leu Arg Pro
    50                  55                  60

Asp Tyr Arg Asp Arg Ile Arg Leu Phe Glu Asn Gly Ser Leu Leu Leu
65                  70                  75                  80

Ser Asp Leu Gln Leu Ala Asp Glu Gly Thr Tyr Glu Val Glu Ile Ser
                85                  90                  95

Ile Thr Asp Asp Thr Phe Thr Gly Glu Lys Thr Ile Asn Leu Thr Val
            100                 105                 110

Asp Val
```

<210> SEQ ID NO 5
<211> LENGTH: 282
<212> TYPE: DNA
<213> ORGANISM: Homo sapiens

<400> SEQUENCE: 5

```
tgcccatttc gaggccacag gtgttggtgg cttcaaccac tgtgctggag ctcagcgagg     60
ccttcacctt gaactgctca catgagaatg gcaccaagcc cagctacacc tggctgaagg    120
atggcaagcc cctcctcaat gactcgagaa tgctcctgtc ccccgaccaa aaggtgctca    180
ccatcacccg cgtgctcatg gaggatgacg acctgtacag ctgcatggtg gagaacccca    240
tcagccaggg ccgcagcctg cctgtcaaga tcaccgtata ca                       282
```

<210> SEQ ID NO 6
<211> LENGTH: 94
<212> TYPE: PRT
<213> ORGANISM: Homo sapiens

<400> SEQUENCE: 6

```
Pro Ile Ser Arg Pro Gln Val Leu Val Ala Ser Thr Thr Val Leu Glu
1               5                   10                  15

Leu Ser Glu Ala Phe Thr Leu Asn Cys Ser His Glu Asn Gly Thr Lys
            20                  25                  30

Pro Ser Tyr Thr Trp Leu Lys Asp Gly Lys Pro Leu Leu Asn Asp Ser
        35                  40                  45

Arg Met Leu Leu Ser Pro Asp Gln Lys Val Leu Thr Ile Thr Arg Val
    50                  55                  60

Leu Met Glu Asp Asp Asp Leu Tyr Ser Cys Met Val Glu Asn Pro Ile
65                  70                  75                  80

Ser Gln Gly Arg Ser Leu Pro Val Lys Ile Thr Val Tyr Arg
                85                  90
```

<210> SEQ ID NO 7
<211> LENGTH: 94
<212> TYPE: DNA
<213> ORGANISM: Homo sapiens

<400> SEQUENCE: 7

```
gaagaagctc cctttacatc atcttgtcta caggaggcat cttcctcctt gtgaccttgg     60
```
tgacagtctg tgcctgctgg aaaccctcca aaag                                    94

<210> SEQ ID NO 8
<211> LENGTH: 31
<212> TYPE: PRT
<213> ORGANISM: Homo sapiens

<400> SEQUENCE: 8

Arg Ser Ser Leu Tyr Ile Ile Leu Ser Thr Gly Gly Ile Phe Leu Leu
1               5                   10                  15

Val Thr Leu Val Thr Val Cys Ala Cys Trp Lys Pro Ser Lys Arg
            20                  25                  30

<210> SEQ ID NO 9
<211> LENGTH: 74
<212> TYPE: DNA
<213> ORGANISM: Homo sapiens

<400> SEQUENCE: 9
gaaacagaag aagctagaaa agcaaaactc cctggaatac atggatcaga atgatgaccg      60
cctgaaacca gaag                                                         74

<210> SEQ ID NO 10
<211> LENGTH: 25
<212> TYPE: PRT
<213> ORGANISM: Homo sapiens

<400> SEQUENCE: 10

Lys Gln Lys Lys Leu Glu Lys Gln Asn Ser Leu Glu Tyr Met Asp Gln
1               5                   10                  15

Asn Asp Asp Arg Leu Lys Pro Glu Ala
            20                  25

<210> SEQ ID NO 11
<211> LENGTH: 71
<212> TYPE: DNA
<213> ORGANISM: Homo sapiens

<400> SEQUENCE: 11
cagacaccct ccctcgaagt ggtgagcagg aacggaagaa ccccatggca ctctatatcc      60
tgaaggacaa g                                                            71

<210> SEQ ID NO 12
<211> LENGTH: 23
<212> TYPE: PRT
<213> ORGANISM: Homo sapiens

<400> SEQUENCE: 12

Asp Thr Leu Pro Arg Ser Gly Glu Gln Glu Arg Lys Asn Pro Met Ala
1               5                   10                  15

Leu Tyr Ile Leu Lys Asp Lys
            20

<210> SEQ ID NO 13
<211> LENGTH: 303
<212> TYPE: DNA
<213> ORGANISM: Homo sapiens

<400> SEQUENCE: 13
gactccccgg agaccgagga gaacccggcc ccggagcctc gaagcgcgac ggagcccggc      60
ccgcccggct actccgtgtc tcccgccgtg cccggccgct cgccggggct gcccatccgc      120

```
tctgcccgcc gctacccgcg ctccccagcg cgctccccag ccaccggccg gacacactcg     180
tcgccgccca gggccccgag ctcgcccggc cgctcgcgca gcgcctcgcg cacactgcgg     240
actgcgggcg tgcacataat ccgcgagcaa gacgaggccg gcccggtgga gatcagcgcc     300
tga                                                                   303
```

<210> SEQ ID NO 14
<211> LENGTH: 100
<212> TYPE: PRT
<213> ORGANISM: Homo sapiens

<400> SEQUENCE: 14

```
Asp Ser Pro Glu Thr Glu Glu Asn Pro Ala Pro Glu Pro Arg Ser Ala
1               5                   10                  15

Thr Glu Pro Gly Pro Pro Gly Tyr Ser Val Ser Pro Ala Val Pro Gly
            20                  25                  30

Arg Ser Pro Gly Leu Pro Ile Arg Ser Ala Arg Arg Tyr Pro Arg Ser
        35                  40                  45

Pro Ala Arg Ser Pro Ala Thr Gly Arg Thr His Ser Ser Pro Pro Arg
    50                  55                  60

Ala Pro Ser Ser Pro Gly Arg Ser Arg Ser Ala Ser Arg Thr Leu Arg
65                  70                  75                  80

Thr Ala Gly Val His Ile Ile Arg Glu Gln Asp Glu Ala Gly Pro Val
                85                  90                  95

Glu Ile Ser Ala
            100
```

<210> SEQ ID NO 15
<211> LENGTH: 1251
<212> TYPE: DNA
<213> ORGANISM: Homo sapiens

<400> SEQUENCE: 15

```
atgaagagag aaaggggagc cctgtccaga gcctccaggg ccctgcgcct tgctcctttt      60
gtctaccttc ttctgatcca gacagacccc ctggaggggg tgaacatcac cagccccgtg     120
cgcctgatcc atggcaccgt ggggaagtcg gctctgcttt ctgtgcagta cagcagtacc     180
agcagcgaca ggcctgtagt gaagtggcag ctgaagcggg acaagccagt gaccgtggtg     240
cagtccattg gcacagaggt catcggcacc ctgcggcctg actatcgaga ccgtatccga     300
ctctttgaaa atggctccct gcttctcagc gacctgcagc tggccgatga gggcacctat     360
gaggtcgaga tctccatcac cgacgacacc ttcactgggg agaagaccat caaccttact     420
gtagatgtgc ccatttcgag gccacaggtg ttggtggctt caaccactgt gctggagctc     480
agcgaggcct tcaccttgaa ctgctcacat gagaatggca ccaagcccag ctacacctgg     540
ctgaaggatg gcaagcccct cctcaatgac tcgagaatgc tcctgtcccc cgaccaaaag     600
gtgctcacca tcacccgcgt gctcatggag gatgacgacc tgtacagctg catggtggag     660
aaccccatca gccagggccg cagcctgcct gtcaagatca ccgtatacag aagaagctcc     720
ctttacatca tcttgtctac aggaggcatc ttcctccttg tgaccttggt gacagtctgt     780
gcctgctgga aaccctccaa aaggaaacag aagaagctag aaaagcaaaa ctccctggaa     840
tacatggatc agaatgatga ccgcctgaaa ccagaagcag acacccctccc tcgaagtggt     900 gagcaggaac ggaagaaccc catggcactc tatatcctga aggacaagga ctccccggag     960
accgaggaga acccggcccc ggagcctcga agcgcgacgg agcccggccc gccggctac    1020
```

```
tccgtgtctc cgccgtgcc cggccgctcg ccggggctgc ccatccgctc tgcccgccgc    1080
tacccgcgct ccccagcgcg ctcccagcc accggccgga cacactcgtc gccgcccagg    1140
gccccgagct cgcccggccg ctcgcgcagc gcctcgcgca cactgcggac tgcgggcgtg    1200
cacataatcc gcgagcaaga cgaggccggc ccggtggaga tcagcgcctg a             1251
```

<210> SEQ ID NO 16
<211> LENGTH: 416
<212> TYPE: PRT
<213> ORGANISM: Homo sapiens

<400> SEQUENCE: 16

```
Met Lys Arg Glu Arg Gly Ala Leu Ser Arg Ala Ser Arg Ala Leu Arg
1               5                  10                  15

Leu Ala Pro Phe Val Tyr Leu Leu Ile Gln Thr Asp Pro Leu Glu
            20                  25                  30

Gly Val Asn Ile Thr Ser Pro Val Arg Leu Ile His Gly Thr Val Gly
        35                  40                  45

Lys Ser Ala Leu Leu Ser Val Gln Tyr Ser Ser Thr Ser Ser Asp Arg
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
        195                 200                 205

Met Glu Asp Asp Asp Leu Tyr Ser Cys Met Val Glu Asn Pro Ile Ser
    210                 215                 220

Gln Gly Arg Ser Leu Pro Val Lys Ile Thr Val Tyr Arg Arg Ser Ser
225                 230                 235                 240

Leu Tyr Ile Ile Leu Ser Thr Gly Gly Ile Phe Leu Leu Val Thr Leu
                245                 250                 255

Val Thr Val Cys Ala Cys Trp Lys Pro Ser Lys Arg Lys Gln Lys Lys
            260                 265                 270

Leu Glu Lys Gln Asn Ser Leu Glu Tyr Met Asp Gln Asn Asp Asp Arg
        275                 280                 285

Leu Lys Pro Glu Ala Asp Thr Leu Pro Arg Ser Gly Glu Gln Glu Arg
    290                 295                 300

Lys Asn Pro Met Ala Leu Tyr Ile Leu Lys Asp Lys Asp Ser Pro Glu
305                 310                 315                 320

Thr Glu Glu Asn Pro Ala Pro Gly Pro Arg Ser Ala Thr Glu Pro Gly
                325                 330                 335
```

Pro Pro Gly Tyr Ser Val Ser Pro Ala Val Pro Gly Arg Ser Pro Gly
            340                 345                 350

Leu Pro Ile Arg Ser Ala Arg Arg Tyr Pro Arg Ser Pro Ala Arg Ser
        355                 360                 365

Pro Ala Thr Gly Arg Thr His Ser Ser Pro Pro Arg Ala Pro Ser Ser
    370                 375                 380

Pro Gly Arg Ser Arg Ser Ala Ser Arg Thr Leu Arg Thr Ala Gly Val
385                 390                 395                 400

His Ile Ile Arg Glu Gln Asp Glu Ala Gly Pro Val Glu Ile Ser Ala
                405                 410                 415

<210> SEQ ID NO 17
<211> LENGTH: 1257
<212> TYPE: DNA
<213> ORGANISM: Mus musculus

<400> SEQUENCE: 17
atgaagagag aaagggggagc cctgtcaaga gcctccaggg ctctgcgcct ctctccttt      60 gtctacctgc ttctcatcca gccagtcccc ctggagggg tgaacatcac cagcccagta    120
cgtctgatcc acggcacagt ggggaagtcg gccctgcttt ccgtgcagta cagtagcacc    180
agcagcgaca gcccgtggt gaagtggcag ctgaagcgtg acaagccagt gaccgtggtg    240
cagtctatag gcacagaggt cattggcact ctgcggcctg actatcgaga ccgtatccgg    300
ctctttgaaa tggctccctt gcttctcagc gacctgcagc tggcggatga gggaaccctat    360 gaagtggaga tttccatcac tgacgacacc ttcaccgggg agaagaccat caacctcacc    420
gtggatgtgc ccatttcaag gccgcaggta ttagtggctt caaccactgt gctggagctc    480
agtgaggcct tcaccctcaa ctgctcccat gagaatggca ccaagcctag ctacacgtgg    540
ctgaaggatg gcaaaccccct cctcaatgac tcccgaatgc tcctgtcccc tgaccaaaag    600
gtgctcacca tcacccgagt actcatggaa gatgacgacc tgtacagctg tgtggtggag    660
aaccccatca gccaggtccg cagcctgcct gtcaagatca ctgtgtatag aagaagctcc    720
ctctatatca tcttgtctac aggaggcatc ttcctccttg tgaccctggt gacagtttgt    780
gcctgctgga acccctcaaa aaagtctagg aagaagagga agttggagaa gcaaaactcc    840
ttggaataca tggatcagaa tgatgaccgc ctaaaatcag aagcagatac cctaccccga    900
agtggagaac aggagcggaa gaacccaatg gcactctata tcctgaagga taaggattcc    960
tcagagccag atgaaaaccc tgctacagag ccacggagca ccacagaacc cggtcccccct    1020 ggctactccg tgtcgccgcc cgtgcccggc cgctctccgg gcttcccat ccgctcagcc    1080 cgccgctacc cgcgctcccc agcacgttcc cctgccactg gccggacgca cgtcgcca    1140 ccgcgggccc cgagctcgcc aggccgctcg cgcagctctt cgcgctcact gcggactgca    1200
ggcgtgcaga gaatccggga gcaggacgag tcagggcagg tggagatcag tgcctga    1257

<210> SEQ ID NO 18
<211> LENGTH: 418
<212> TYPE: PRT
<213> ORGANISM: Mus musculus

<400> SEQUENCE: 18

Met Lys Arg Glu Arg Gly Ala Leu Ser Arg Ala Ser Arg Ala Leu Arg
1               5                   10                  15

Leu Ser Pro Phe Val Tyr Leu Leu Leu Ile Gln Pro Val Pro Leu Glu
            20                  25                  30

-continued

```
Gly Val Asn Ile Thr Ser Pro Val Arg Leu Ile His Gly Thr Val Gly
             35                  40                  45

Lys Ser Ala Leu Leu Ser Val Gln Tyr Ser Ser Thr Ser Ser Asp Lys
 50                  55                  60

Pro Val Val Lys Trp Gln Leu Lys Arg Asp Lys Pro Val Thr Val Val
 65                  70                  75                  80

Gln Ser Ile Gly Thr Glu Val Ile Gly Thr Leu Arg Pro Asp Tyr Arg
                 85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
        195                 200                 205

Met Glu Asp Asp Asp Leu Tyr Ser Cys Val Val Glu Asn Pro Ile Ser
    210                 215                 220

Gln Val Arg Ser Leu Pro Val Lys Ile Thr Val Tyr Arg Arg Ser Ser
225                 230                 235                 240

Leu Tyr Ile Ile Leu Ser Thr Gly Gly Ile Phe Leu Leu Val Thr Leu
                245                 250                 255

Val Thr Val Cys Ala Cys Trp Lys Pro Ser Lys Ser Arg Lys Lys
            260                 265                 270

Arg Lys Leu Glu Lys Gln Asn Ser Leu Glu Tyr Met Asp Gln Asn Asp
        275                 280                 285

Asp Arg Leu Lys Ser Glu Ala Asp Thr Leu Pro Arg Ser Gly Glu Gln
    290                 295                 300

Glu Arg Lys Asn Pro Met Ala Leu Tyr Ile Leu Lys Asp Lys Asp Ser
305                 310                 315                 320

Ser Glu Pro Asp Glu Asn Pro Ala Thr Glu Pro Arg Ser Thr Thr Glu
                325                 330                 335

Pro Gly Pro Pro Gly Tyr Ser Val Ser Pro Val Pro Gly Arg Ser
            340                 345                 350

Pro Gly Leu Pro Ile Arg Ser Ala Arg Arg Tyr Pro Arg Ser Pro Ala
        355                 360                 365

Arg Ser Pro Ala Thr Gly Arg Thr His Thr Ser Pro Arg Ala Pro
    370                 375                 380

Ser Ser Pro Gly Arg Ser Arg Ser Ser Arg Ser Leu Arg Thr Ala
385                 390                 395                 400

Gly Val Gln Arg Ile Arg Glu Gln Asp Glu Ser Gly Gln Val Glu Ile
                405                 410                 415

Ser Ala

<210> SEQ ID NO 19
<211> LENGTH: 720
<212> TYPE: DNA
```

<213> ORGANISM: Homo sapiens

<400> SEQUENCE: 19

```
atgaagagag aaagggagc cctgtccaga gcctccaggg ccctgcgcct tgctcctttt    60
gtctaccttc ttctgatcca gacagacccc ctggagggg tgaacatcac cagcccgtg   120
cgcctgatcc atggcaccgt ggggaagtcg gctctgcttt ctgtgcagta cagcagtacc   180
agcagcgaca ggcctgtagt gaagtggcag ctgaagcggg acaagccagt gaccgtggtg   240
cagtccattg gcacagaggt catcggcacc ctgcggcctg actatcgaga ccgtatccga   300
ctctttgaaa atggctccct gcttctcagc gacctgcagc tggccgatga gggcacctat   360
gaggtcgaga tctccatcac cgacgacacc ttcactgggg agaagaccat caaccttact   420
gtagatgtgc ccatttcgag gccacaggtg ttggtggctt caaccactgt gctggagctc   480
agcgaggcct tcaccttgaa ctgctcacat gagaatggca ccaagcccag ctacacctgg   540
ctgaaggatg gcaagcccct cctcaatgac tcgagaatgc tcctgtcccc cgaccaaaag   600
gtgctcacca tcacccgcgt gctcatggag gatgacgacc tgtacagctg catggtggag   660
aacccccatca gccagggccg cagcctgcct gtcaagatca ccgtatacag aagaagctcc   720
```

<210> SEQ ID NO 20
<211> LENGTH: 240
<212> TYPE: PRT
<213> ORGANISM: Homo sapiens

<400> SEQUENCE: 20

```
Met Lys Arg Glu Arg Gly Ala Leu Ser Arg Ala Ser Arg Ala Leu Arg
 1               5                  10                  15

Leu Ala Pro Phe Val Tyr Leu Leu Ile Gln Thr Asp Pro Leu Glu
            20                  25                  30

Gly Val Asn Ile Thr Ser Pro Val Arg Leu Ile His Gly Thr Val Gly
        35                  40                  45

Lys Ser Ala Leu Leu Ser Val Gln Tyr Ser Ser Thr Ser Ser Asp Arg
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
        195                 200                 205

Met Glu Asp Asp Asp Leu Tyr Ser Cys Met Val Glu Asn Pro Ile Ser
    210                 215                 220

Gln Gly Arg Ser Leu Pro Val Lys Ile Thr Val Tyr Arg Arg Ser Ser
```

| | | | |
|---|---|---|---|
| 225 | 230 | 235 | 240 |

<210> SEQ ID NO 21
<211> LENGTH: 621
<212> TYPE: DNA
<213> ORGANISM: Homo sapiens

<400> SEQUENCE: 21

```
gtgaacatca ccagccccgt gcgcctgatc catggcaccg tggggaagtc ggctctgctt      60
tctgtgcagt acagcagtac cagcagcgac aggcctgtag tgaagtggca gctgaagcgg     120
gacaagccag tgaccgtggt gcagtccatt ggcacagagg tcatcggcac cctgcggcct     180
gactatcgag accgtatccg actctttgaa atggctccc tgcttctcag cgacctgcag      240
ctggccgatg agggcaccta tgaggtcgag atctccatca ccgacgacac cttcactggg     300
gagaagacca tcaaccttac tgtagatgtg cccatttcga ggccacaggt gttggtggct     360
tcaaccactg tgctggagct cagcgaggcc ttcaccttga actgctcaca tgagaatggc     420
accaagccca gctacacctg gctgaaggat ggcaagcccc tcctcaatga ctcgagaatg     480
ctcctgtccc ccgaccaaaa ggtgctcacc atcacccgcg tgctcatgga ggatgacgac     540
ctgtacagct gcatggtgga gaaccccatc agccagggcc gcagcctgcc tgtcaagatc     600
accgtataca gaagaagctc c                                               621
```

<210> SEQ ID NO 22
<211> LENGTH: 207
<212> TYPE: PRT
<213> ORGANISM: Homo sapiens

<400> SEQUENCE: 22

```
Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
            20                  25                  30

Val Val Lys Trp Gln Leu Lys Arg Asp Lys Pro Val Thr Val Val Gln
        35                  40                  45

Ser Ile Gly Thr Glu Val Ile Gly Thr Leu Arg Pro Asp Tyr Arg Asp
    50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val Pro Ile
            100                 105                 110

Ser Arg Pro Gln Val Leu Val Ala Ser Thr Thr Val Leu Glu Leu Ser
        115                 120                 125

Glu Ala Phe Thr Leu Asn Cys Ser His Glu Asn Gly Thr Lys Pro Ser
    130                 135                 140

Tyr Thr Trp Leu Lys Asp Gly Lys Pro Leu Leu Asn Asp Ser Arg Met
145                 150                 155                 160

Leu Leu Ser Pro Asp Gln Lys Val Leu Thr Ile Thr Arg Val Leu Met
                165                 170                 175

Glu Asp Asp Asp Leu Tyr Ser Cys Met Val Glu Asn Pro Ile Ser Gln
            180                 185                 190

Gly Arg Ser Leu Pro Val Lys Ile Thr Val Tyr Arg Arg Ser Ser
        195                 200                 205
```

<210> SEQ ID NO 23
<211> LENGTH: 328
<212> TYPE: DNA
<213> ORGANISM: Homo sapiens

<400> SEQUENCE: 23

```
gtgaacatca ccagccccgt gcgcctgatc catggcaccg tggggaagtc ggctctgctt      60
tctgtgcagt acagcagtac cagcagcgac aggcctgtag tgaagtggca gctgaagcgg     120
gacaagccag tgaccgtggt gcagtccatt ggcacagagg tcatcggcac cctgcggcct     180
gactatcgag accgtatccg actctttgaa aatggctccc tgcttctcag cgacctgcag     240
ctggccgatg agggcaccta tgaggtcgag atctccatca ccgacgacac cttcactggg     300
gagaagacca tcaaccttac tgtagatg                                       328
```

<210> SEQ ID NO 24
<211> LENGTH: 110
<212> TYPE: PRT
<213> ORGANISM: Homo sapiens

<400> SEQUENCE: 24

Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
            20                  25                  30

Val Val Lys Trp Gln Leu Lys Arg Asp Lys Pro Val Thr Val Val Gln
        35                  40                  45

Ser Ile Gly Thr Glu Val Ile Gly Thr Leu Arg Pro Asp Tyr Arg Asp
    50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val
            100                 105                 110

<210> SEQ ID NO 25
<211> LENGTH: 1152
<212> TYPE: DNA
<213> ORGANISM: Homo sapiens

<400> SEQUENCE: 25

```
gtgaacatca ccagccccgt gcgcctgatc catggcaccg tggggaagtc ggctctgctt      60
tctgtgcagt acagcagtac cagcagcgac aggcctgtag tgaagtggca gctgaagcgg     120
gacaagccag tgaccgtggt gcagtccatt ggcacagagg tcatcggcac cctgcggcct     180
gactatcgag accgtatccg actctttgaa aatggctccc tgcttctcag cgacctgcag     240
ctggccgatg agggcaccta tgaggtcgag atctccatca ccgacgacac cttcactggg     300
gagaagacca tcaaccttac tgtagatgtg cccatttcga ggccacaggt gttggtggct     360
tcaaccactg tgctggagct cagcgaggcc ttcaccttga actgctcaca tgagaatggc     420
accaagccca gctacacctg gctgaaggat ggcaagcccc tcctcaatga ctcgagaatg     480
ctcctgtccc ccgaccaaaa ggtgctcacc atcccccgcg tgctcatgga ggatgacgac     540
ctgtacagct gcatggtgga gaaccccatc agccagggcc gcagcctgcc tgtcaagatc     600
accgtataca agaagagctc cctttacatc atcttgtcta caggaggcat cttcctcctt     660
```

```
gtgaccttgg tgacagtctg tgcctgctgg aaaccctcca aaaggaaaca gaagaagcta    720
gaaaagcaaa actccctgga atacatggat cagaatgatg accgcctgaa accagaagca    780 gacacccctcc ctcgaagtgg tgagcaggaa cggaagaacc ccatggcact ctatatcctg   840
aaggacaagg actccccgga gaccgaggag aacccggccc cggagcctcg aagcgcgacg    900
gagcccggcc cgcccggcta ctccgtgtct cccgccgtgc ccggccgctc gcggggctg     960 cccatccgct ctgcccgccg ctacccgcgc tccccagcgc gctccccagc caccggccgg   1020
acacactcgt cgccgcccag ggccccgagc tcgcccggcc gctcgcgcag cgcctcgcgc   1080
acactgcgga ctgcgggcgt gcacataatc cgcgagcaag acgaggccgg cccggtggag   1140
atcagcgcct ga                                                       1152
```

<210> SEQ ID NO 26
<211> LENGTH: 383
<212> TYPE: PRT
<213> ORGANISM: Homo sapiens

<400> SEQUENCE: 26

```
Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
            20                  25                  30

Val Val Lys Trp Gln Leu Lys Arg Asp Lys Pro Val Thr Val Val Gln
        35                  40                  45

Ser Ile Gly Thr Glu Val Ile Gly Thr Leu Arg Pro Asp Tyr Arg Asp
    50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val Pro Ile
            100                 105                 110

Ser Arg Pro Gln Val Leu Val Ala Ser Thr Thr Val Leu Glu Leu Ser
        115                 120                 125

Glu Ala Phe Thr Leu Asn Cys Ser His Glu Asn Gly Thr Lys Pro Ser
    130                 135                 140

Tyr Thr Trp Leu Lys Asp Gly Lys Pro Leu Leu Asn Asp Ser Arg Met
145                 150                 155                 160

Leu Leu Ser Pro Asp Gln Lys Val Leu Thr Ile Thr Arg Val Leu Met
                165                 170                 175

Glu Asp Asp Asp Leu Tyr Ser Cys Met Val Glu Asn Pro Ile Ser Gln
            180                 185                 190

Gly Arg Ser Leu Pro Val Lys Ile Thr Val Tyr Arg Arg Ser Ser Leu
        195                 200                 205

Tyr Ile Ile Leu Ser Thr Gly Gly Ile Phe Leu Leu Val Thr Leu Val
    210                 215                 220

Thr Val Cys Ala Cys Trp Lys Pro Ser Lys Arg Lys Gln Lys Lys Leu
225                 230                 235                 240

Glu Lys Gln Asn Ser Leu Glu Tyr Met Asp Gln Asn Asp Asp Arg Leu
                245                 250                 255

Lys Pro Glu Ala Asp Thr Leu Pro Arg Ser Gly Glu Gln Glu Arg Lys
            260                 265                 270

Asn Pro Met Ala Leu Tyr Ile Leu Lys Asp Lys Asp Ser Pro Glu Thr
        275                 280                 285
```

```
Glu Glu Asn Pro Ala Pro Glu Pro Arg Ser Ala Thr Glu Pro Gly Pro
    290                 295                 300

Pro Gly Tyr Ser Val Ser Pro Ala Val Pro Gly Arg Ser Pro Gly Leu
305                 310                 315                 320

Pro Ile Arg Ser Ala Arg Arg Tyr Pro Arg Ser Pro Ala Arg Ser Pro
                325                 330                 335

Ala Thr Gly Arg Thr His Ser Ser Pro Pro Arg Ala Pro Ser Ser Pro
            340                 345                 350

Gly Arg Ser Arg Ser Ala Ser Arg Thr Leu Arg Thr Ala Gly Val His
        355                 360                 365

Ile Ile Arg Glu Gln Asp Glu Ala Gly Pro Val Glu Ile Ser Ala
370                 375                 380
```

<210> SEQ ID NO 27
<211> LENGTH: 256
<212> TYPE: PRT
<213> ORGANISM: Homo sapiens

<400> SEQUENCE: 27

```
Met Lys Arg Glu Arg Gly Ala Leu Ser Arg Ala Ser Arg Ala Leu Arg
1               5                   10                  15

Leu Ala Pro Phe Val Tyr Leu Leu Ile Gln Thr Asp Pro Leu Glu
                20                  25                  30

Gly Val Asn Ile Thr Ser Pro Val Arg Leu Ile His Gly Thr Val Gly
            35                  40                  45

Lys Ser Ala Leu Leu Ser Val Gln Tyr Ser Ser Thr Ser Ser Asp Arg
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
                100                 105                 110

Gln Leu Ala Asp Glu Gly Thr Tyr Glu Val Glu Ile Ser Ile Thr Asp
            115                 120                 125

Asp Thr Phe Thr Gly Glu Lys Thr Ile Asn Leu Thr Val Asp Val Pro
        130                 135                 140

Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
                180                 185                 190

Met Leu Leu Ser Pro Asp Gln Lys Val Leu Thr Ile Thr Arg Val Leu
            195                 200                 205

Met Glu Asp Asp Asp Leu Asp Ser Cys Val Val Glu Asn Pro Ile Asn
        210                 215                 220

Gln Gly Arg Thr Leu Pro Cys Lys Ile Thr Val Tyr Lys Lys Ser Ser
225                 230                 235                 240

Leu Ser Ser Ile Trp Leu Gln Glu Ala Phe Ser Ser Leu Gly Pro Trp
                245                 250                 255
```

<210> SEQ ID NO 28
<211> LENGTH: 256
<212> TYPE: PRT

<213> ORGANISM: Homo sapiens

<400> SEQUENCE: 28

```
Met Lys Arg Glu Arg Gly Ala Leu Ser Arg Ala Ser Arg Ala Leu Arg
1               5                   10                  15

Leu Ala Pro Phe Val Tyr Leu Leu Ile Gln Thr Asp Pro Leu Glu
            20                  25                  30

Gly Val Asn Ile Thr Ser Pro Val Arg Leu Ile His Gly Thr Val Gly
            35                  40                  45

Lys Ser Ala Leu Leu Ser Val Gln Tyr Ser Ser Thr Ser Ser Asp Arg
 50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
        195                 200                 205

Met Glu Asp Asp Asp Leu Asp Ser Cys Val Val Glu Asn Pro Ile Asn
    210                 215                 220

Gln Gly Arg Thr Leu Pro Cys Lys Ile Thr Val Tyr Lys Lys Ser Ser
225                 230                 235                 240

Phe Tyr Ile Ile Cys Leu Lys Glu Ala Ser Ser Ser Phe Gly Pro Trp
                245                 250                 255
```

<210> SEQ ID NO 29
<211> LENGTH: 213
<212> TYPE: PRT
<213> ORGANISM: Homo sapiens

<400> SEQUENCE: 29

```
Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
            20                  25                  30

Val Val Lys Trp Gln Leu Lys Arg Asp Lys Pro Val Thr Val Val Gln
        35                  40                  45

Ser Ile Gly Thr Glu Val Ile Gly Thr Leu Arg Pro Asp Tyr Arg Asp
    50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val Pro Ile
```

-continued

```
            100                 105                 110
Ser Arg Pro Gln Val Leu Val Ala Ser Thr Thr Val Leu Glu Leu Ser
        115                 120                 125
Glu Ala Phe Thr Leu Asn Cys Ser His Glu Asn Gly Thr Lys Pro Ser
        130                 135                 140
Tyr Thr Trp Leu Lys Asp Gly Lys Pro Leu Leu Asn Asp Ser Arg Met
145                 150                 155                 160
Leu Leu Ser Pro Asp Gln Lys Val Leu Thr Ile Thr Arg Val Leu Met
                165                 170                 175
Glu Asp Asp Leu Tyr Ser Cys Met Val Glu Asn Pro Ile Ser Gln
                180                 185                 190
Gly Arg Ser Leu Pro Val Lys Ile Thr Val Tyr Arg Arg Ser Ser His
            195                 200                 205
His His His His His
        210

<210> SEQ ID NO 30
<211> LENGTH: 439
<212> TYPE: PRT
<213> ORGANISM: Homo sapiens

<400> SEQUENCE: 30

Val Asn Ile Thr Ser Pro Val Arg Leu Ile His Gly Thr Val Gly Lys
1               5                   10                  15
Ser Ala Leu Leu Ser Val Gln Tyr Ser Ser Thr Ser Ser Asp Arg Pro
            20                  25                  30
Val Val Lys Trp Gln Leu Lys Arg Asp Lys Pro Val Thr Val Val Gln
        35                  40                  45
Ser Ile Gly Thr Glu Val Ile Gly Thr Leu Arg Pro Asp Tyr Arg Asp
    50                  55                  60
Arg Ile Arg Leu Phe Glu Asn Gly Ser Leu Leu Leu Ser Asp Leu Gln
65                  70                  75                  80
Leu Ala Asp Glu Gly Thr Tyr Glu Val Glu Ile Ser Ile Thr Asp Asp
                85                  90                  95
Thr Phe Thr Gly Glu Lys Thr Ile Asn Leu Thr Val Asp Val Pro Ile
                100                 105                 110
Ser Arg Pro Gln Val Leu Val Ala Ser Thr Thr Val Leu Glu Leu Ser
        115                 120                 125
Glu Ala Phe Thr Leu Asn Cys Ser His Glu Asn Gly Thr Lys Pro Ser
        130                 135                 140
Tyr Thr Trp Leu Lys Asp Gly Lys Pro Leu Leu Asn Asp Ser Arg Met
145                 150                 155                 160
Leu Leu Ser Pro Asp Gln Lys Val Leu Thr Ile Thr Arg Val Leu Met
                165                 170                 175
Glu Asp Asp Leu Tyr Ser Cys Met Val Glu Asn Pro Ile Ser Gln
                180                 185                 190
Gly Arg Ser Leu Pro Val Lys Ile Thr Val Tyr Arg Arg Ser Ser Glu
            195                 200                 205
Pro Lys Ser Cys Asp Lys Thr His Thr Cys Pro Pro Cys Pro Ala Pro
        210                 215                 220
Glu Leu Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
```

-continued

```
Asp Val Ser His Glu Asp Pro Glu Val Lys Phe Asn Trp Tyr Val Asp
                260                 265                 270
Gly Val Glu Val His Asn Ala Lys Thr Lys Pro Arg Glu Glu Gln Tyr
            275                 280                 285
Asn Ser Thr Tyr Arg Val Val Ser Val Leu Thr Val Leu His Gln Asp
        290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Pro Arg
                325                 330                 335
Glu Pro Gln Val Tyr Thr Leu Pro Pro Ser Arg Glu Glu Met Thr Lys
            340                 345                 350
Asn Gln Val Ser Leu Thr Cys Leu Val Lys Gly Phe Tyr Pro Ser Asp
        355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
Leu Ser Leu Ser Pro Gly Lys
            435

<210> SEQ ID NO 31
<211> LENGTH: 186
<212> TYPE: PRT
<213> ORGANISM: Homo sapiens

<400> SEQUENCE: 31

Val Arg Leu Ile His Gly Thr Val Gly Lys Ser Ala Leu Leu Ser Val
1               5                  10                  15
Gln Tyr Ser Ser Thr Ser Ser Asp Arg Pro Val Val Lys Trp Gln Leu
            20                  25                  30
Lys Arg Asp Lys Pro Val Thr Val Val Gln Ser Ile Gly Thr Glu Val
        35                  40                  45
Ile Gly Thr Leu Arg Pro Asp Tyr Arg Asp Arg Ile Arg Leu Phe Glu
    50                  55                  60
Asn Gly Ser Leu Leu Leu Ser Asp Leu Gln Leu Ala Asp Glu Gly Thr
65                  70                  75                  80
Tyr Glu Val Glu Ile Ser Ile Thr Asp Asp Thr Phe Thr Gly Glu Lys
                85                  90                  95
Thr Ile Asn Leu Thr Val Asp Val Pro Ile Ser Arg Pro Gln Val Leu
            100                 105                 110
Val Ala Ser Thr Thr Val Leu Glu Leu Ser Glu Ala Phe Thr Leu Asn
        115                 120                 125
Cys Ser His Glu Asn Gly Thr Lys Pro Ser Tyr Thr Trp Leu Lys Asp
    130                 135                 140
```

-continued

```
Gly Lys Pro Leu Leu Asn Asp Ser Arg Met Leu Leu Ser Pro Asp Gln
145                 150                 155                 160

Lys Val Leu Thr Ile Thr Arg Val Leu Met Glu Asp Asp Asp Leu Tyr
                165                 170                 175

Ser Cys Met Val Glu Asn Pro Ile Ser Gln
            180                 185

<210> SEQ ID NO 32
<211> LENGTH: 256
<212> TYPE: PRT
<213> ORGANISM: Homo sapiens

<400> SEQUENCE: 32

Met Lys Arg Glu Arg Gly Ala Leu Ser Arg Ala Ser Arg Ala Leu Arg
1               5                   10                  15

Leu Ala Pro Phe Val Tyr Leu Leu Ile Gln Thr Asp Pro Leu Glu
                20                  25                  30

Gly Val Asn Ile Thr Ser Pro Val Arg Leu Ile His Gly Thr Val Gly
                35                  40                  45

Lys Ser Ala Leu Leu Ser Val Gln Tyr Ser Ser Thr Ser Ser Asp Arg
50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
                100                 105                 110

Gln Leu Ala Asp Glu Gly Thr Tyr Glu Val Glu Ile Ser Ile Thr Asp
                115                 120                 125

Asp Thr Phe Thr Gly Glu Lys Thr Ile Asn Leu Thr Val Asp Val Pro
130                 135                 140

Ile Ser Arg Pro Gln Val Leu Gly Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
                180                 185                 190

Met Leu Leu Ser Pro Asp Gln Lys Val Leu Thr Ile Thr Arg Val Leu
                195                 200                 205

Met Glu Asp Asp Asp Leu Tyr Ser Cys Val Val Glu Asn Pro Ile Asn
                210                 215                 220

Gln Gly Arg Thr Leu Pro Cys Lys Ile Thr Glu Tyr Arg Lys Ser Ser
225                 230                 235                 240

Leu Ser Ser Ile Trp Leu Gln Glu Ala Phe Ser Ser Leu Gly Pro Trp
                245                 250                 255
```